(12) United States Patent
Chee et al.

(10) Patent No.: US 6,455,548 B2
(45) Date of Patent: Sep. 24, 2002

(54) 4-ALKYL PIPERIDINYL PYRROLIDINE MODULATORS OF CHEMOKINE RECEPTOR ACTIVITY

(75) Inventors: Jennifer Chee, Cambridge, MA (US); Jill N. Johanson, Cranford, NJ (US); Frank Kayser, San Francisco, CA (US); William H. Parsons, Belle Mead; Kathleen M. Rupprecht, Cranford, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/795,030

(22) Filed: Feb. 27, 2001

Related U.S. Application Data

(60) Provisional application No. 60/185,555, filed on Feb. 28, 2000.

(51) Int. Cl.[7] ............. A61K 31/454; C07D 409/14
(52) U.S. Cl. ............. 514/326; 546/209; 546/208
(58) Field of Search .............. 514/326; 546/209, 546/208

(56) References Cited

U.S. PATENT DOCUMENTS 6,166,037 A * 12/2000 Budhu et al. ............... 514/326

* cited by examiner

*Primary Examiner*—C. S. Aulakh
(74) *Attorney, Agent, or Firm*—Mollie M. Yang; David L. Rose; J. Eric Thies

(57) ABSTRACT

The present invention is directed to pyrrolidine compounds of the formula I:

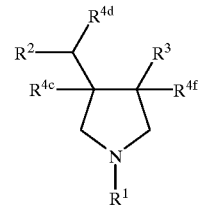

(wherein $R^1$, $R^2$, $R^3$, $R^{4c}$, $R^{4d}$, and $R^{4f}$ are defined herein) which are useful as modulators of chemokine receptor activity. In particular, these compounds are useful as modulators of the chemokine receptors CCR-3 and/or CCR-5.

8 Claims, No Drawings

4-ALKYL PIPERIDINYL PYRROLIDINE MODULATORS OF CHEMOKINE RECEPTOR ACTIVITY

CROSS REFERENCE TO RELATED APPLICATIONS

This application claims the benefit of Provisional Application Ser. No. 60/185,555, filed Feb. 28, 2000.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, Cytokine, 3, 165–183 (1991) and Murphy, Rev. Immun., 12, 593–633 (1994)). There are two classes of chemokines, C-X-C ($\alpha$) and C—C ($\beta$), depending on whether the first two cysteines are separated by a single amino acid (C-X-C) or are adjacent (C—C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., Nature, 381, 661–666 (1996)).

The chemokines bind specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al.,J. Biol. Chem., 270, 22123–22128 (1995); Beote, et al, Cell, 72, 415–425 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al.,J. Biol. Chem., 270, 16491–16494 (1995); CCR4 (or "CKR-4" or "CC-CKR-4") [MIP-1$\alpha$, RANTES, MCP-1] (Power, et al., J. Biol. Chem., 270, 19495–19500 (1995)); CCR-5 (or "CKR-5" or "CC-CKR-5") [MIP-1$\alpha$, RANTES, MIP-1$\beta$] (Sanson, et al., Biochemistry, 35, 3362–3367 (1996)); and the Duffy blood-group antigen [RANTES, MCP-1] (Chaudhun, et al.,J. Biol. Chem., 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., J. Exp. Med. 183, 2421–2426 (1996). An antagonist of the CCR3 receptor, Met-chemokine beta 7, has been proposed to be useful in ameliorating leukocyte infiltration associated with allergic inflammation (Nibbs, et al., J. Immunol., 164, 1488–1497 (2000)). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-M, or ARV.

Certain compounds have been demonstrated to inhibit the replication of HIV, including soluble CD4 protein and synthetic derivatives (Smith, et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, N. Engl. J. Med., 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., Nature, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that P3-chemokine ligands prevent HIV-1 from fusing with the cell (Dragic, et al., Nature, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., Nature, 384, 179–183 (1996); Trkola, et al., Nature, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (Nature, 382, 722–725 (1996)). Absence of CCR-5 appears to confer protection from HIV-1 infection (Nature, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (Nature Medicine, 2(11), 1240–1243 (1996)). Nevertheless, drugs targeting chemokine receptors may not be unduly compromised by the genetic diversity of HIV-1 (Zhang, et al., Nature, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to compounds of formula I:

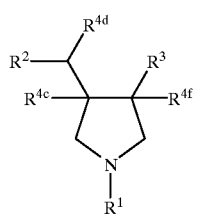

I wherein:
$R^1$ is -X-$R^8$, wherein X is selected from the group consisting of:
  (1) —$CH_2$—,
  (2) —CO—,
  (3) —$CH_2CH_2$—,
  (4) —$CH_2CH_2CH_2$—, and
  (5) —CH($C_{1-6}$ alkyl)-,
and wherein $R^8$ is selected from:
  phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:
(a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
  (i) hydroxy,
  (ii) halogen,
  (iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
    (A) phenyl, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH($C_{1-6}$ alkyl), —N($C_{1-6}$ alkyl)($C_{1-6}$ alkyl), or trifluoromethyl,
    (B) naphthyl, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH($C_{1-6}$ alkyl), —N($C_{1-6}$ alkyl)($C_{1-6}$ alkyl), or trifluoromethyl,
    (C) heterocycle, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH($C_{1-6}$ alkyl), —N($C_{1-6}$ alkyl)($C_{1-6}$ alkyl), or trifluoromethyl,
    (D) hydroxy,
    (E) —O($C_{1-6}$ alkyl),
    (F) —$CO_2$($C_{1-6}$ alkyl),
    (G) —S(O)$_n$-($C_{1-6}$ alkyl), wherein n is an integer selected from 0, 1 and 2,
    (H) halogen,
    (I) —$NH_2$,
    (J) —NH($C_{1-6}$ alkyl), and
    (K) —N($C_{1-6}$ alkyl)($C_{1-6}$ alkyl),
  (iv) —$NR^9$-$COR^{10}$,
  (v) —$NR^9$-$CO_2R^{10}$,
  (vi) —CO—$NR^9R^{10}$,
  (vii) —OCO—$NR^9R^{10}$,
  (viii) —$NR^9CO$—$NR^9R^{10}$,
  (ix) —$S(O)_2$—$NR^9R^{10}$, wherein n is an integer selected from 0, 1 and 2,
  (x) —$NR^9S(O)_2$-$R^{10}$,
  (xi) —$NR^9S(O)_2$—$NR^9R^{10}$,
  (xii) —$S(O)_n$-$R^9$,
  (xiii) —$CF_3$,
  (xiv) —$CHF_2$,
  (xv) —$CH_2F$,
  (xvi) —O-$R^9$,
  (xvii) —O($C_{1-6}$ alkyl)-O-$R^9$,
  (xviii) phenyl,
  (xix) naphthyl,
  (xx) indenyl,
  (xxi) indanyl,
  (xxii) heterocycle,
  (xxiii) —CO-phenyl,
  (xxiv) —CO-naphthyl,
  (xxv) —CO-indenyl,
  (xxvi) —CO-indanyl,
  (xxvii) —CO-heterocycle,
  (xxviii) —OCO-$R^9$, (xxix) —OCO$_2$-R$^9$, and
(xxx) —CO-R$^5$,
(b) —O—C$_{1-6}$alkyl, —O—C$_{2-6}$ alkenyl, —O—C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$,
(iv) —NR$^9$-COR$^{10}$,
(v) —NR$^9$-CO2R$^1$O,
(vi) —CO-NR$^9$R$^{10}$,
(vii) —OCO-NR$^9$R$^{10}$,
(viii) —NR$^9$CO—NR$^9$R$^{10}$,
(ix) —S(O)$_2$—NR$^9$R$^{10}$,
(x) —NR$^9$S(O)$_2$-R$^{10}$,
(xi) —NR$^9$S(O)$_2$—NR$^9$R$^{10}$,
(xii) —S(O)$_n$-R$^9$,
(xiii) —CF$_3$,
(xiv) —CHF$_2$,
(xv) —CH$_2$F,
(xvii) —O-R$^9$,
(xvii) —O(C$_{1-6}$ alkyl)-O-R$^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO-R$^9$,
(xxix) —OCO$_2$-R$^9$, and
(xxx) —CO-R$^5$,
(c) —NO$_2$,
(d) hydroxy,
(e) halogen,
(f) —NR$^9$R$^{10}$,
(g) —NR$^9$-COR$^{10}$,
(h) —NR$^9$-CO2R$^{10}$,
(i) —CO-NR$^9$R$^{10}$,
(j) —OCO-NR$^9$R$^{10}$,
(k) —NR$^9$CO—NR$^9$R$^{10}$,
(l) —S(O)$_2$—NR$^9$R$^{10}$,
(m) —NR$^9$S(O)$_2$-R$^{10}$,
(n) —NR$^9$S(O)$_2$—NR$^9$R$^{10}$,
(o) —S(O)$_n$-R$^9$,
(p) —CF$_3$,
(q) —CBF$_2$,
(r) —CH$_2$F,
(s) —OCO-R$^9$,
(t) —OCO$_2$-R$^9$, and
(u) —CO-R$^9$;
R$^2$ is:

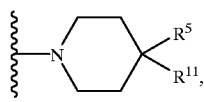

wherein R$^5$ is selected from:
(1) C$_{1-10}$alkyl or C$_{2-10}$alkenyl,
which is unsubstituted or substituted, where the substituents are independently selected from:
(a) hydroxy,
(b) C$_{1-6}$alkoxy,
(c) oxo,
(d) halogen,
(e) —OC(C$_{1-6}$ alkyl),
(f) benzyloxy,
(g) —NH$_2$,
(h) —NHCO(C$_{1-6}$ alkyl),
(i) —NHSO$_2$(C$_{1-6}$ alkyl),
(j) cyclopropyl,
(k) cyclobutyl,
(l) cyclopentyl,
(m) cyclohexyl,
(n) cycloheptyl,
(o) tetrahydropyranyl,
(p) piperidinyl, and
(q) N-(C$_{1-6}$ alkyl)piperidinyl,
(2) —C$_{0-6}$alkyl-O-C$_{1-6}$alkyl,
which is unsubstituted or substituted, where the substituents are independently selected from:
(a) hydroxy,
(b) C$_{1-6}$alkoxy,
(c) oxo,
(d) halogen,
(e) —OC(C$_{1-6}$ alkyl),
(f) —NH$_2$,
(g) —NHCO(C$_{1-6}$ alkyl),
(h) —NHSO$_2$(C$_{1-6}$ alkyl),
(i) cyclopropyl,
(j) cyclobutyl,
(k) cyclopentyl,
(l) cyclohexyl,
(m) cycloheptyl,
(n) tetrahydropyranyl,
(o) piperidinyl, and
(p) N-(C$_{1-6}$ alkyl)piperidinyl,
(3) —C$_{1-6}$alkyl-O-C$_{2-6}$alkenyl,
which is unsubstituted or substituted, where the substituents are independently selected from:
(a) hydroxy,
(b) C$_{1-6}$alkoxy,
(c) oxo,
(d) halogen,
(e) —OC(C$_{1-6}$ alkyl),
(f) —NH$_2$,
(g) —NHCO(C$_{1-6}$ alkyl),
(h) —NHSO2(C$_{1-6}$ alkyl),
(i) cyclopropyl,
(j) cyclobutyl,
(k) cyclopentyl,
(l) cyclohexyl,
(m) cycloheptyl,
(n) tetrahydropyranyl,
(o) piperidinyl, and
(p) N-(C$_{1-6}$ alkyl)piperidinyl,
and wherein R$^{11}$ is selected from:
(1) -hydrogen,
(2) —OH,
(3) —C$_{1-6}$alkyl, and
(4) -halogen;
R$^3$ is thienyl or furanyl, which may be unsubstituted or substituted, where the substituents are independently selected from:
(1) C$_{1-6}$ alkyl, which is unsubstituted or substituted, wherein the substituents are independently selected from:
(a) hydroxy, (b) halogen,
(c) —NR$^9$R$^{10}$,
(d) —NR9-COR$^{10}$,
(e) —NR$^9$-CO$_2$R$^{10}$,
(f) —CF$_3$,
(g) —CHF$_2$,
(h) —CH$_2$F,
(i) —O-R$^9$, and
(j) phenyl, (2) —O—C$_{1-6}$alkyl, unsubstituted or substituted with a substituent which is independently selected from:
(a) hydroxy,
(b) halogen,
(c) —NR$^9$R$^{10}$,
(d) —NR$^9$-COR$^{10}$,
(e) —NR$^9$-CO$^2$R$^{10}$,
(f) —CF$_3$,
(g) —CHF$_2$,
(h) —CH$_2$F,
(i) —O-R$^9$, and
(j) phenyl, (3) hydroxy,
(4) halogen,
(5) —CF$_3$,
(6) —CHF$_2$,
(7) —CH$_2$F,
(8) —0-R$^9$, and
(9) —O(C$_{1-6}$ alkyl)-O-R$^9$;

R$^{4c}$, R$^{4d}$, and R$^{4f}$ are independently selected from the group consisting of:

(1) hydrogen, and
(2) C$_{1-6}$ alkyl;

and pharmaceutically acceptable salts thereof and individual diastereomers thereof.

Preferred compounds of the present invention include those of formula Ia:

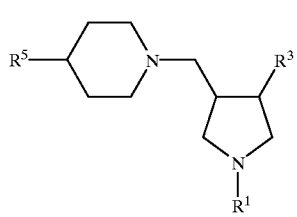

Ia wherein:

R$^1$, R$^5$ and R$^3$ are defined herein;

and pharmaceutically acceptable salts and individual diastereomers thereof.

Preferred compounds of the present invention include those of formula Ib:

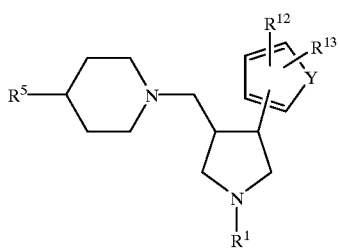

Ib wherein:
R$^1$ is -X-R$^8$, wherein X is selected from the group consisting of:
(1) —CH$_2$—,
(2) —CO—, and
(3) —CH$_2$CH$_2$—,
and wherein R$^8$ is selected from:
phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:
(a) C$_{1-6}$ alkyl, C$_{2-6}$ alkenyl, C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$, wherein R$^9$ and R$^{10}$ are independently selected from hydrogen, C$_{1-6}$ alkyl, C$_{2-6}$ alkenyl, and C$_{2-6}$ alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
(B) naphthyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
(C) heterocycle, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
(D) hydroxy,
(E) —O(C$_{1-6}$ alkyl),
(F) —CO$_2$(C$_{1-6}$ alkyl),
(G) —S(O)$_n$—(C$_{1-6}$ alkyl), wherein n is an integer selected from 0, 1 and 2,
(H) halogen,
(I) —NH$_2$,
(J) —NH(C$_{1-6}$ alkyl), and
(K) —N(C$_{1-6}$ alkyl)(C$_{1-6}$ alkyl),
(iv) —NR$^9$-COR$^{10}$,
(v) —NR$^9$-CO$_2$R$^{10}$,
(vi) —CO—NR$^9$R$^{10}$,
(vii) —OCO—NR$^9$R$^{10}$, (viii) —NR$^9$CO—NR$^9$R$^{10}$,
(ix) —S(O)$_2$-NR$^9$R$^{10}$, wherein n is an integer selected from 0, 1 and 2,
(x) —NR$^9$S(O)$_2$-R$^{10}$,
(xi) —NR$^9$S(O)$_2$-NR$^9$R$^{10}$,
(xii) —S(O)$_n$-R$^9$,
(xiii) —CF$_3$,
(xiv) —CHF$_2$,
(xv) —CH$_2$F,
(xvi) —O-R$^9$,
(xvii) —O(C$_{1-6}$ alkyl)-O-R$^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO-R$^9$,
(xxix) —OCO$_2$-R$^9$, and
(xxx) —CO-R$^9$,
(b) —O—C$_{1-6}$alkyl, —O—C$_{2-6}$ alkenyl, —O—C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$,
(iv) —NR$^9$-COR$^{10}$,
(v) —NR$^9$-CO$_2$R$^{10}$,
(vi) —CO—NR$^9$R$^{10}$,
(vii) —OCO—NR$^9$R$^{10}$,
(viii) —NR$^9$CO—NR$^9$R$^{10}$,
(ix) —S(O)$_2$—NR$^9$R$^{10}$,
(x) —NR$^9$S(O)$_2$-R$^{10}$,
(xi) —NR$^9$S(O)$_2$—NR$^9$R$^{10}$,
(xii) —S(O)$_n$-R$^9$,
(xiii) —CF$_3$,
(xiv) —CHF$_2$,
(xv) —CH$_2$F,
(xvii) —O-R$^9$,
(xvii) —O(C$_{1-6}$ alkyl)-O-R$^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO-R$^9$,
(xxix) —OCO$_2$-R$^9$, and
(xxx) —CO-R$^9$,
(c) —NO$_2$,
(d) hydroxy,
(e) halogen,
(f) —NR$^9$R$^{10}$,
(g) —NR$^9$-COR$^{10}$,
(h) —NR$^9$-CO$_2$R$^{10}$,
(i) —CO—NR$^9$R$^{10}$,
(j) —OCO—NR$^9$R$^{10}$,
(k) —NR$^9$CO—NR$^9$R$^{10}$,
(l) —S(O)$_2$—NR$^9$R$^{10}$,
(m) —NR$^9$S(O)$_2$-R$^{10}$,
(n) —NR$^9$S(O)$_2$—NR$^9$R$^{10}$,
(o) —S(O)$_n$-R$^9$,
(p) —CF$_3$,
(q) —CHF$_2$,
(r) —CH$_2$F,
(s) —OCO-R$^9$,
(t) —OCO$_2$-R$^9$, and
(u) —CO-R$^9$;
R$^5$ is selected from:
(1) C$_{1-10}$alkyl or C$_{2-10}$alkenyl,
which is unsubstituted or substituted, where the substituents are independently selected from:
(a) hydroxy,
(b) C$_{1-6}$alkoxy,
(c) halogen,
(d) —OC(C$_{1-6}$ alkyl),
(e) —NH$_2$,
(f) —NHCO(C$_{1-6}$ alkyl),
(g) —NHSO$_2$(C$_{1-6}$ alkyl),
(h) cyclopropyl,
(i) cyclobutyl,
(j) cyclopentyl,
(k) cyclohexyl,
(l) cycloheptyl,
(m) tetrahydropyranyl,
(n) piperidinyl, and
(o) N—(C$_{1-6}$ alkyl)piperidinyl,
(2) —C$_{0-6}$alkyl-O—C$_{1-6}$alkyl,
which is unsubstituted or substituted, where the substituents are independently selected from:
(a) hydroxy,
(b) C$_{1-6}$alkoxy,
(c) halogen,
(d) —OC(C$_{1-6}$ alkyl),
(e) —NH$_2$,
(f) —NHCO(C$_{1-6}$ alkyl),
(g) —NHSO$_2$(C$_{1-6}$ alkyl),
(h) cyclopropyl,
(i) cyclobutyl,
(j) cyclopentyl,
(k) cyclohexyl,
(l) cycloheptyl,
(m) tetrahydropyranyl,
(n) piperidinyl, and
(o) N-(C$_{1-6}$ alkyl)piperidinyl,
(3) —C$_{1-6}$alkyl-O—C$_{3-6}$alkenyl,
which is unsubstituted or substituted, where the substituents are independently selected from:
(a) hydroxy,
(b) C$_{1-6}$alkoxy,
(c) halogen,
(d) —OC(C1l6 alkyl),
(e) —NH$_2$,
(f) —NHCO(C$_{1-6}$ alkyl),
(g) —NHSO$_2$(C$_{1-6}$ alkyl),
(h) cyclopropyl,
(i) cyclobutyl,
(j) cyclopentyl,
(k) cyclohexyl,
(l) cycloheptyl,
(m) tetrahydropyranyl,
(n) piperidinyl, and
(o) N-(C$_{1-6}$ alkyl)piperidinyl;
R$^{12}$ and R$^{13}$ are independently selected from:

(1) hydrogen,
(2) $C_{1-6}$ alkyl, which is unsubstituted or substituted, wherein the substituents are independently selected from:
 (a) hydroxy,
 (b) halogen,
 (c) —$NR^9R^{10}$,
 (d) —$NR^9$-$COR^{10}$,
 (e) —$NR^9$-$CO_2R^{10}$,
 (f) —$CF_3$,
 (g) —$CHF_2$,
 (h) —$CH_2F$,
 (i) —O-$R^9$, and
 (j) phenyl,
(3) —O—$C_{1-6}$alkyl, unsubstituted or substituted with a substituent which is independently selected from:
 (a) hydroxy,
 (b) halogen,
 (c) —$NR^9R^{10}$,
 (d) —$NR^9$-$COR^{10}$,
 (e) —$NR^9$-$CO_2R^{10}$,
 (f) —$CF_3$,
 (g) —$CBF_2$,
 (h) —$CH_2F$,
 (i) —O-$R^9$, and
 (j) phenyl,
(4) hydroxy,
(5) halogen,
(6) —$CF_3$,
(7) —$CHF_2$,
(8) —$CH_2F$,
(9) —O-$R^9$, and
(10) —O($C_{1-6}$ alkyl)-O-$R^9$;

Y is —S— or —O—;

and pharmaceutically acceptable salts thereof and individual diastereomers thereof.

More preferred compounds of the present invention include those of formula Ic:

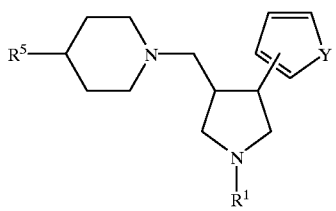

Ic wherein:

$R^1$, $R^5$ and Y are defined herein;

and pharmaceutically acceptable salts and individual diastereomers thereof.

Highly preferred compounds of the present invention include those of formula Id:

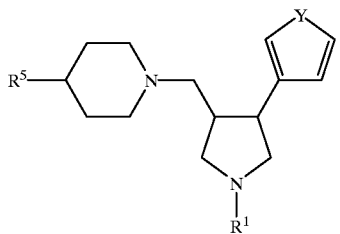

Id wherein $R^1$, $R^5$ and Y are defined herein;
and pharmaceutically acceptable salts and individual diastereomers thereof.

Highly preferred compounds of the present invention further include those of formula Id:

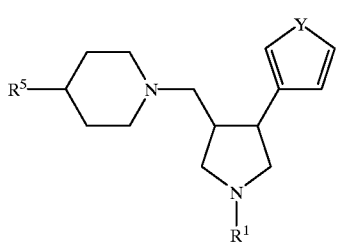

Id wherein
$R^1$ is -X-$R^8$, wherein X is selected from the group consisting of:
 (1) —$CH_2$—, and
 (2) —CO—,
and wherein $R^8$ is selected from:
 phenyl, naphthyl, indenyl, indanyl, indolyl, quinolyl, isoquinolyl, benzofuranyl, dihydrobenzofuranyl, methylenedioxybenzoyl, benzopyrazolyl, and benzotriazolyl, which may be unsubstituted or substituted, where the substituents are independently selected from:
 (a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
  (i) hydroxy,
  (ii) halogen,
  (iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
   (A) phenyl, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH($C_{1-6}$ alkyl), —N($C_{1-6}$ alkyl)($C_{1-6}$ alkyl), or trifluoromethyl,
   (B) naphthyl, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH($C_{1-6}$ alkyl), —N($C_{1-6}$ alkyl)($C_{1-6}$ alkyl), or trifluoromethyl,
   (C) heterocycle, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH($C_{1-6}$ alkyl), —N($C_{1-6}$ alkyl)($C_{1-6}$ alkyl), or trifluoromethyl,
(D) hydroxy,
(E) —O($C_{1-6}$ alkyl),
(F) —$CO_2(C_{1-6}$ alkyl),
(G) —S(O)$_n$-($C_{1-6}$ alkyl), wherein n is an integer selected from 0, 1 and 2,
(H) halogen,
(I) —$NH_2$,
(J) —NH($C_{1-6}$ alkyl), and
(K) —N($C_{1-6}$ alkyl)($C_{1-6}$ alkyl),
(iv) —$NR^9$-$COR^{10}$,
(v) —$NR^9$-$CO_2R^{10}$,
(vi) —CO—$NR^9R^{10}$,
(vii) —OCO—$NR^9R^{10}$,
(viii) —$NR^9$CO—$NR^9R^{10}$,
(ix) —$S(O)_2$-$NR^9R^{10}$, wherein n is an integer selected from 0, 1 and 2,
(x) —$NR^9S(O)_2$-$R^{10}$,
(xi) —$NR^9S(O)_2$—$NR^9R^{10}$,
(xii) —$S(O)_n$-$R^9$,
(xiii) —$CF_3$,
(xiv) —$CBF_2$,
(xv) —$CH_2F$,
(xvi) —O-$R^9$,
(xvii) —O($C_{1-6}$ alkyl)-O-$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO-$R^9$,
(xxix) —$OCO_2$-$R^9$, and
(xxx) —CO-$R^5$,
(b) —O—$C_{1-6}$alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$-$COR^{10}$,
(v) —$NR^9$-$CO_2R^{10}$,
(vi) —CO—$NR^9R^{10}$,
(vii) —OCO—$NR^9R^{10}$,
(viii) —$NR^9$CO—$NR^9R^{10}$,
(ix) —$S(O)_2$—$NR^9R^{10}$,
(x) —$NR^9S(O)_2$-$R^{10}$,
(xi) —$NR^9S(O)_2$—$NR^9R^{10}$,
(xii) —$S(O)_n$-$R^9$,
(xiii) —$CF_3$,
(xiv) —$CHF_2$,
(xv) —$CH_2F$,
(xvii) —O-$R^9$,
(xvii) —O($C_{1-6}$ alkyl)-O-$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO-$R^9$,
(xxix) —$OCO_2$-$R^9$, and
(xxx) —CO-$R^5$,
(c) —$NO_2$,
(d) hydroxy,
(e) halogen,
(f) —$NR^9R^{10}$,
(g) —$NR^9$-$COR^{10}$,
(h) —$NR^9$-$CO_2R^{10}$,
(i) —CO—$NR^9R^{10}$,
(j) —OCO—$NR^9R^{10}$,
(k) —$NR^9$CO—$NR^9R^{10}$,
(l) —$S(O)_2$—$NR^9R^{10}$,
(m) —$NR^9S(O)_2$-$R^{10}$,
(n) —$NR^9S(O)_2$—$NR^9R^{10}$,
(o) —$S(O)_n$-$R^9$,
(p) —$CF_3$,
(q) —$CHF_2$,
(r) —$CH_2F$,
(s) —OCO-$R^9$,
(t) —$OCO_2$-$R^9$, and
(u) —CO-$R^9$;
$R^5$ is selected from:
(1) $C_{1-10}$alkyl or $C_{2-10}$alkenyl,
which is unsubstituted or substituted, where the substituents are independently selected from:
(a) hydroxy,
(b) $C_{1-6}$alkoxy,
(c) halogen,
(d) —OC($C_{1-6}$ alkyl),
(e) —$NH_2$,
(f) —NHCO($C_{1-6}$ alkyl),
(g) —$NHSO_2(C_{1-6}$ alkyl),
(h) cyclopropyl,
(i) cyclobutyl,
(j) cyclopentyl,
(k) cyclohexyl,
(l) cycloheptyl,
(m) tetrahydropyranyl,
(n) piperidinyl, and
(o) N-($C_{1-6}$ alkyl)piperidinyl,
(2) —$C_{0-6}$alkyl-O—$C_{1-6}$alkyl,
which is unsubstituted or substituted, where the substituents are independently selected from:
(a) hydroxy,
(b) $C_{1-6}$alkoxy,
(c) halogen,
(d) —OC($C_{1-6}$ alkyl),
(e) —$NH_2$,
(f) —NHCO($C_{1-6}$ alkyl),
(g) —$NHSO_2(C_{1-6}$ alkyl),
(h) cyclopropyl,
(i) cyclobutyl,
(j) cyclopentyl,
(k) cyclohexyl,
(l) cycloheptyl,
(m) tetrahydropyranyl,
(n) piperidinyl, and
(o) N-($C_{1-6}$ alkyl)piperidinyl,
(3) —$C_{1-6}$alkyl-O—$C_{3-6}$alkenyl,
which is unsubstituted or substituted, where the substituents are independently selected from:

(a) hydroxy,
(b) $C_{1-6}$alkoxy,
(c) halogen,
(d) —OC($C_{1-6}$ alkyl),
(e) —NH$_2$,
(f) —NHCO($C_{1-6}$ alkyl),
(g) —NHSO$_2$($C_{1-6}$ alkyl),
(h) cyclopropyl,
(i) cyclobutyl,
(j) cyclopentyl,
(k) cyclohexyl,
(l) cycloheptyl,
(m) tetrahydropyranyl,
(n) piperidinyl, and
(o) N-($C_{1-6}$ alkyl)piperidinyl;
Y is —S— or —O—;
and pharmaceutically acceptable salts and individual diastereomers thereof.

In the present invention it is preferred that $R^1$ is -X-$R^8$, wherein X is selected from the group consisting of:
(1) —CH$_2$—, and
(2) —CO—,
and wherein $R^8$ is selected from: phenyl, naphthyl, biphenyl, indenyl, indanyl, and heterocycle,
which may be unsubstituted or substituted, where the substituents are independently selected from:
  (a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
    (i) hydroxy,
    (ii) halogen,
    (iii) —NR$^9$R$^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
      (A) phenyl, unsubstituted or substituted, wherein the substituents are independently selected from: halogen, hydroxy, $C_{1-6}$alkyl, $C_{1-6}$alkoxy, —CO$_2$($C_{1-6}$ alkyl), —NH$_2$, —NH($C_{1-6}$ alkyl), —N($C_{1-6}$ alkyl)($C_{1-6}$ alkyl), or trifluoromethyl,
      (B) naphthyl, unsubstituted or substituted, wherein the substituents are independently selected from: halogen, hydroxy, $C_{1-6}$alkyl, $C_{1-6}$alkoxy, —CO$_2$($C_{1-6}$ alkyl), —NH$_2$, —NH($C_{1-6}$ alkyl), —N($C_{1-6}$ alkyl)($C_{1-6}$ alkyl), or trifluoromethyl,
      (C) heterocycle, unsubstituted or substituted, wherein the substituents are independently selected from: halogen, hydroxy, $C_{1-6}$alkyl, $C_{1-6}$alkoxy, —CO$_2$($C_{1-6}$ alkyl), —NH$_2$, —NH($C_{1-6}$ alkyl), —N($C_{1-6}$ alkyl)($C_{1-6}$ alkyl), or trifluoromethyl,
      (D) hydroxy,
      (E) —O($C_{1-6}$ alkyl),
      (F) —CO$_2$($C_{1-6}$ alkyl),
      (G) —S(O)$_n$-($C_{1-6}$ alkyl), wherein n is an integer selected from 0, 1 and 2,
      (H) halogen,
      (I) —NH$_2$,
      (J) —NH($C_{1-6}$ alkyl), and
      (K) —N($C_{1-6}$ alkyl)($C_{1-6}$ alkyl),
    (iv) —NR$^9$-COR$^{10}$,
    (v) —NR$^9$-CO$_2$R$^{10}$,
    (vi) —CO—NR$^9$R$^{10}$,
    (vii) —OCO-NR$^9$R$^{10}$,
    (viii) —NR$^9$CO—NR$^9$R$^{10}$,
    (ix) —S(O)$_2$—NR$^9$R$^{10}$, wherein n is an integer selected from 0, 1 and 2,
    (x) —NR$^9$S(O)$_2$-R$^{10}$,
    (xi) —NR$^9$S(O)$_2$—NR$^9$R$^{10}$,
    (xii) —S(O)$_n$-R$^9$,
    (xiii) —CF$_3$,
    (xiv) —CHF$_2$,
    (xv) —CH$_2$F,
    (xvi) —O-R$^9$,
    (xvii) —O($C_{1-6}$ alkyl)-O-R$^9$,
    (xviii) phenyl,
    (xix) naphthyl,
    (xx) indenyl,
    (xxi) indanyl,
    (xxii) heterocycle,
    (xxiii) —CO-phenyl,
    (xxiv) —CO-naphthyl,
    (xxv) —CO-indenyl,
    (xxvi) —CO-indanyl,
    (xxvii) —CO-heterocycle,
    (xxviii) —OCO-R$^9$,
    (xxix) —OCO$_2$-R$^9$, and
    (xxx) —CO-R$^9$,
  (b) —O—$C_{1-6}$alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
    (i) hydroxy,
    (ii) halogen,
    (iii) —NR$^9$R$^{10}$,
    (iv) —NR$^9$-COR$^{10}$,
    (v) —NR$^9$-CO$_2$R$^{10}$,
    (vi) —CO—NR$^9$R$^{10}$,
    (vii) —OCO—NR$^9$R$^{10}$,
    (viii) —NR$^9$CO—NR$^9$R$^{10}$, (ix) —S(O)$_2$—NR$^9$R$^{10}$,
    (x) —NR$^9$S(O)$_2$-R$^{10}$,
    (xi) —NR$^9$S(O)$_2$—NR$^9$R$^{10}$,
    (xii) —S(O)$_n$-R$^9$,
    (xiii) —CF$_3$,
    (xiv) —CHF$_2$,
    (xv) —CH$_2$F,
    (xvii) —O-R$^9$,
    (xvii) —O($C_{1-6}$ alkyl)-O-R$^9$,
    (xviii) phenyl,
    (xix) naphthyl,
    (xx) indenyl,
    (xxi) indanyl,
    (xxii) heterocycle,
    (xxiii) —CO-phenyl,
    (xxiv) —CO-naphthyl,
    (xxv) —CO-indenyl,
    (xxvi) —CO-indanyl,
    (xxvii) —CO-heterocycle,
    (xxviii) —OCO-R$^9$,
    (xxix) —OCO$_2$-R$^9$, and
    (xxx) —CO-R$^9$,
  (c) —NO$_2$,
  (d) hydroxy,
  (e) halogen,
  (f) —NR$^9$R$^{10}$,
  (g) —NR$^9$-COR$^{10}$,
  (h) —NR$^9$-CO$_2$R$^{10}$,
  (i) —CO—NR$^9$R$^{10}$,
  (j) —OCO—NR$^9$R$^{10}$,
  (k) —NR$^9$CO—NR$^9$R$^{10}$, (l) —S(O)$_2$—NR$^9$R$^{10}$,
(m) —NR$^9$S(O)$_2$-R$^{10}$,
(n) —NR$^9$S(O)$_2$—NR$^9$R$^{10}$,
(o) —S(O)$_n$-R$^9$,
(p) —CF$_3$,
(q) —CHF$_2$,
(r) —CH$_2$F,
(s) —OCO-R$^9$,
(t) —OCO$_2$-R$^9$, and
(u) —CO-R$^9$.

In the present invention it is even more preferred that R$^1$ is -X-R$^8$, wherein X is selected from the group consisting of:
(1) —CH$_2$—, and
(2) —CO—, and wherein R$^8$ is selected from:
phenyl, naphthyl, indenyl, indanyl, indolyl, quinolyl, isoquinolyl, benzofuranyl, dihydrobenzofuranyl, methylenedioxybenzoyl, benzopyrazolyl, and benzotriazolyl, which may be unsubstituted or substituted, where the substituents are independently selected from:
  (a) C$_{1-6}$ alkyl, C$_{2-6}$ alkenyl, C$_{2-6}$ alkynyl, wherein the alkyl, alkenyl, or alkynyl is unsubstituted or substituted, wherein the substituents are independently selected from:
    (i) hydroxy,
    (ii) halogen,
    (iii) —NR$^9$R$^{10}$, wherein R$^9$ and R$^{10}$ are independently selected from hydrogen, C$_{1-6}$ alkyl, C$_{2-6}$ alkenyl, and C$_{2-6}$ alkynyl, wherein the alkyl, alkenyl, or alkynyl is unsubstituted or substituted, wherein the substituents are independently selected from:
      (A) phenyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
      (B) naphthyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
      (C) heterocycle, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
      (D) hydroxy,
      (E) —O(C$_{1-6}$ alkyl),
      (F) —CO$_2$(C$_{1-6}$ alkyl),
      (G) —S(O)$_n$-(C$_{1-6}$ alkyl), wherein n is an integer selected from 0, 1 and 2,
      (H) halogen,
      (I) —NH$_2$,
      (J) —NH(C$_{1-6}$ alkyl), and
      (K) —N(C$_{1-6}$ alkyl)(C$_{1-6}$ alkyl),
    (v) —NR$^9$-COR$^{10}$,
    (vi) —NR$^9$-CO$_2$R$^{10}$,
    (vii) —CO—NR$^9$R$^{10}$,
    (viii) —OCO—NR$^9$R$^{10}$,
    (ix) —NR$^9$CO—NR$^9$R$^{10}$,
    (x) —S(O)$_2$—NR$^9$R$^{10}$, wherein n is an integer selected from 0, 1 and 2,
    (xi) —NR$^9$S(O)$_2$-R$^{10}$,
    (xii) —NR$^9$S(O)$_2$—NR$^9$R$^{10}$,
    (xiii) —S(O)$_n$-R$^9$,
    (xiv) —CF$_3$,
    (xv) —CBF$_2$,
    (xvi) —CH$_2$F,
    (xvii) —O-R$^9$,
    (xviii) —O(C$_{1-6}$ alkyl)-O-R$^9$,
    (xix) phenyl,
    (xx) naphthyl,
    (xxi) indenyl,
    (xxii) indanyl,
    (xxiii) heterocycle,
    (xxiv) —CO-phenyl,
    (xxv) —CO-naphthyl,
    (xxvi) —CO-indenyl,
    (xxvii) —CO-indanyl,
    (xxviii) —CO-heterocycle,
    (xxix) —OCO-R$^9$,
    (xxx) —OCO$_2$-R$^9$, and
    (xxxi) —CO-R$^9$,
  (b) —O—C$_{1-6}$alkyl, —O—C$_{2-6}$ alkenyl, —O—C$_{2-6}$ alkynyl, wherein the alkyl, alkenyl, or alkynyl is unsubstituted or substituted, wherein the substituents are independently selected from:
    (i) hydroxy,
    (ii) halogen,
    (iii) —NR$^9$R$^{10}$,
    (iv) —NR$^9$-COR$^{10}$,
    (v) —NR$^9$-CO$_2$R$^{10}$,
    (vi) —CO—NR$^9$R$^{10}$,
    (vii) —OCO—NR$^9$R$^{10}$,
    (viii) —NR$^9$CO—NR$^9$R$^{10}$,
    (ix) —S(O)$_2$—NR$^9$R$^{10}$,
    (x) —NR$^9$S(O)$_2$-R$^{10}$,
    (xi) —NR$^9$S(O)$_2$—NR$^9$R$^{10}$,
    (xii) —S(O)$_n$-R$^9$,
    (xiii) —CF$_3$,
    (xiv) —CHF$_2$,
    (xv) —CH$_2$F,
    (xvii) —O-R$^9$,
    (xvii) —O(C$_{1-6}$ alkyl)-O-R$^9$,
    (xviii) phenyl,
    (xix) naphthyl,
    (xx) indenyl,
    (xxi) indanyl,
    (xxii) heterocycle,
    (xxiii) —CO-phenyl,
    (xxiv) —CO-naphthyl,
    (xxv) —CO-indenyl,
    (xxvi) —CO-indanyl,
    (xxvii) —CO-heterocycle,
    (xxviii) —OCO-R$^9$,
    (xxix) —OCO$_2$-R$^9$, and
    (xxx) —CO-R$^9$,
  (c) —NO$_2$,
  (d) hydroxy,
  (e) halogen,
  (f) —NR$^9$R$^{10}$,
  (g) —NR$^9$-COR$^{10}$,
  (h) —NR$^9$-CO$_2$R$^{10}$,
  (i) —CO—NR$^9$R$^{10}$,
  (j) —OCO—NR$^9$R$^{10}$,
  (k) —NR$^9$CO—NR$^9$R$^{10}$,
  (l) —S(O)$_2$—NR$^9$R$^{10}$,
  (m) —NR$^9$S(O)$_2$-R$^{10}$,
  (n) —NR$^9$S(O)$_2$—NR$^9$R$^{10}$,
  (o) —S(O)$_n$-R$^9$, (p) —CF$_3$,
(q) —CHF$_2$,
(r) —CH$_2$F,
(s) —OCO-R$^9$,
(t) —OCO$_2$-R$^9$, and
(u) —CO-R$^9$.

In the present invention it is highly preferred that R$^1$ is selected from the group consisting of:
(1) —CH$_2$-phenyl,
(2) —CO-phenyl,
(3) —CH$_2$-(2,4-dichlorophenyl),
(4) —CO-(2,4-dichlorophenyl),
(5) —CH$_2$-(2-naphthyl),
(6) —CO-(1-naphthyl),
(7) —CH$_2$-indolyl, and
(8) —CO-indolyl.

In the present invention it is more highly preferred that R$^1$ is selected from the group consisting of:
(1) —CH$_2$-phenyl,
(2) —CO-phenyl,
(3) —CH$_2$-(2,4-dichlorophenyl),
(4) —CH$_2$-(7-indolyl), and
(5) —CO-(7-indolyl).

In the present invention it is more highly preferred that R$^1$ is selected from the group consisting of:
(1) —CH$_2$-phenyl, and
(2) —CH$_2$-(2,4-dichlorophenyl).

In the present invention it is preferred that R$^2$ is:

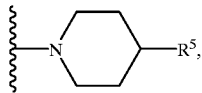

wherein R$^5$ is selected from:
(1) C$_{1-10}$alkyl or C$_{2-10}$alkenyl,
which is unsubstituted or substituted, where the substituents are independently selected from:
(a) hydroxy,
(b) C$_{1-6}$alkoxy,
(c) halogen,
(d) —OC(C$_{1-6}$ alkyl),
(e) —NH$_2$,
(f) —NHCO(C$_{1-6}$ alkyl),
(g) —NHSO$_2$(C$_{16}$ alkyl),
(h) cyclopropyl,
(i) cyclobutyl,
(j) cyclopentyl,
(k) cyclohexyl,
(l) cycloheptyl,
(m) tetrahydropyranyl,
(n) piperidinyl, and
(o) N-(C$_{1-6}$ alkyl)piperidinyl,
(2) —C$_{0-6}$alkyl-O—C$_{1-6}$alkyl,
where the alkyls are independently unsubstituted or substituted, where the substituents are independently selected from:
(a) hydroxy,
(b) C$_{1-6}$alkoxy,
(c) halogen,
(d) —OC(C$_{1-6}$ alkyl),
(e) —NH$_2$,
(f) —NHCO(C$_{1-6}$ alkyl),
(g) —NHSO$_2$(C$_{1-6}$ alkyl),
(h) cyclopropyl,
(i) cyclobutyl,
(j) cyclopentyl,
(k) cyclohexyl,
(l) cycloheptyl,
(m) tetrahydropyranyl,
(n) piperidinyl, and
(o) N-(C$_{1-6}$ alkyl)piperidinyl,
(3) —C$_{1-6}$alkyl-O—C3-6alkenyl,
which is unsubstituted or substituted, where the substituents are independently selected from:
(a) hydroxy,
(b) C$_{1-6}$alkoxy,
(c) halogen,
(d) —OC(C$_{1-6}$ alkyl),
(e) —NH$_2$,
(f) —NHCO(C$_{1-6}$ alkyl),
(g) —NHSO$_2$(C$_{1-6}$ alkyl),
(h) cyclopropyl,
(i) cyclobutyl,
(l) cyclopentyl,
(k) cyclohexyl,
(l) cycloheptyl,
(m) tetrahydropyranyl,
(n) piperidinyl, and
(o) N-(C$_{1-6}$ alkyl)piperidinyl.

In the present invention it is preferred that R$^5$ is selected from:
C$_{1-8}$alkyl, —C$_{0-3}$alkyl-O—C$_{1-6}$alkyl, and —C$_{1-3}$alkyl-O—C$_{3-4}$alkenyl,
which are independently unsubstituted or substituted, where the substituents are independently selected from:
(a) hydroxy,
(b) C$_{1-6}$alkoxy,
(c) —OC(C$_{1-6}$ alkyl),
(d) —NH$_2$,
(e) —NHCO(C$_{1-6}$ alkyl),
(f) —NHSO$_2$(C$_{1-6}$ alkyl),
(g) cyclopropyl,
(h) cyclobutyl,
(i) cyclopentyl,
(j)cyclohexyl,
(k) cycloheptyl,
(l) tetrahydropyranyl,
(m) piperidinyl, and
(n) N-(C$_{1-6}$ alkyl)piperidinyl.

In the present invention it is more preferred that R$^5$ is C$_{1-8}$alkyl,
which is unsubstituted or substituted, where the substituents are independently selected from:
(a) hydroxy,
(b) C$_{1-3}$alkoxy,
(c) —O—C$_{1-3}$alkyl-O—C$_{1-3}$alkyl,
(d) —O—C$_{1-3}$alkyl-hydroxy,
(e) —O—C$_{1-3}$alkyl-cyclopropyl,
(f) —O—C$_{1-3}$alkyl-cyclobutyl,
(g) —O—C$_{3-4}$alkenyl
(h) —OC(C$_{1-6}$ alkyl),
(i) —NH$_2$,
(j) —NHCO(C$_{1-6}$ alkyl),
(k) —NHSO$_2$(C$_{1-6}$ alkyl),
(l) cyclobutyl,
(m) cyclopentyl,
(n) cyclohexyl,
(o) cycloheptyl, (p) tetrahydropyranyl,
(q) piperidinyl, and
(r) N-($C_{1-6}$ alkyl)piperidinyl.

In the present invention it is preferred that $R^3$ is thienyl or furanyl,
which may be unsubstituted or substituted, where the substituents are independently selected from:
(1) $C_{1-6}$ alkyl, which is unsubstituted or substituted, wherein the substituents are independently selected from:
(a) hydroxy,
(b) halogen,
(c) —$NH_2$,
(d) —$NHR^9$,
(e) —$NR^9R^{10}$, wherein $R^9$ and $R^{10}$ are independently selected from $C_{1-6}$ alkyl, wherein the alkyl is unsubstituted or substituted, wherein the substituents are independently selected from:
(A) halogen,
(B) phenyl, and
(C) —$CO_2(C_{1-6}$ alkyl),
(f) —$NR^9$-$COR^{10}$,
(g) —$NR^9$-$CO_2R^{10}$,
(h) —$CF_3$,
(i) —$CHF_2$,
(j) —$CH_2F$,
(k) —O-$R^9$, and
(l) phenyl,
(2) —O—$C_{1-6}$alkyl, unsubstituted or substituted with a substituent which is independently selected from:
(a) hydroxy,
(b) halogen,
(c) —$NH_2$,
(d) —$NHR^9$,
(e) —$NR^9R^{10}$,
(f) —$NR^9$-$COR^{10}$,
(g) —$NR^9$-$CO_2R^{10}$,
(h) —$CF_3$,
(i) —$CBF_2$,
(j) —$CH_2F$,
(k) —O-$R^9$, and
(l) phenyl,
(3) hydroxy,
(4) halogen,
(5) —$CF_3$,
(6) —$CHF_2$,
(7) —$CH_2F$,
(8) —O-$R^9$, and
(9) —O($C_{1-6}$ alkyl)-O-$R^9$.

In the present invention it is more preferred that $R^3$ is thienyl or furanyl, which may be unsubstituted or substituted, where the substituents are independently selected from:
$C_{1-6}$ alkyl, which is unsubstituted or substituted, wherein the substituents are independently selected from:
(a) hydroxy,
(b) —O($C_{1-6}$ alkyl), and
(c) —$CO_2(C_{1-6}$ alkyl).

In the present invention it is highly preferred that $R^3$ is unsubstituted thienyl or furanyl.

In the present invention it is most preferred that $R^3$ be 3-thienyl. The compounds wherein $R^3$ is 3-thienyl have unexpected properties with respect to compounds wherein $R^3$ is 2-thienyl In the present invention it is preferred that $R^{4c}$, $R^{4d}$, and $R^{4h}$ are independently selected from the group consisting of:

(1) hydrogen, and
(2) $C_{1-6}$ alkyl.

In the present invention it is more preferred that $R^{4c}$, and $R^{4h}$ are each hydrogen and that $R^{4d}$ is selected from the group consisting of hydrogen, and —$CH_3$ In the present invention it is most preferred that $R^{4c}$, $R^{4d}$, and $R^{4h}$ are each hydrogen.

The compounds of the instant invention have at least two asymmetric centers at the ring junction of the substitutents bearing $R^2$ and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the most preferred compounds of this invention are of the trans orientation, i.e. as depicted:

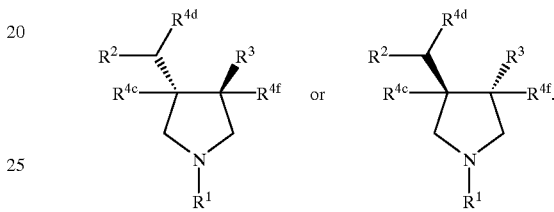

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include the following groups: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, Exemplifying the invention is the use of the compounds disclosed in the Examples and herein.

Specific compounds within the present invention include a compound which selected from the group consisting of:
1-(2,4-Dichlorobenzyl)-3-(S)-(4-pentylpiperidinylmethyl)-4-(S)-(3-thienyl)-pyrrolidine;
1-(2,4-Dichlorobenzyl)-3-(S)-(4-(butyloxy) piperidinylmethyl)-4-(S)-(3-thienyl)-pyrrolidine;
1-(2,4-Dichlorobenzyl)-3-(S)-(4-(hydroxymethyl) piperidinylmethyl)-4-(S)-(3-thienyl)pyrrolidine;
1-(2,4-Dichlorobenzyl)-3-(S)-(4-(methoxymethyl) piperindinylmethyl)-4-(S)-(3-thienyl)pyrrolidine;
1-(2,4-Dichlorobenzyl)-3-(S)-(4-(ethoxymethyl) piperidinylmethyl)-4-(S)-(3-thienyl)pyrrolidine;
1-(2,4-Dichlorobenzyl)-3-(S)-(4-(propoxymethyl) piperidinylmethyl)-4-(S)-(3-thienyl)pyrrolidine;
1-(2,4-Dichlorobenzyl)-3-(S)-(4-(allyloxymethyl) pipelidinylmethyl)-4-(S)-(3-thienyl)pyrrolidine;
1-(2,4-Dichlorobenzyl)-3-(S)-(4-(isopropoxymethyl) piperidinylmethyl)-4-(S)-(3-thienyl)pyrrolidine;
1-(2,4-Dichlorobenzyl)-3-(S)-(4-(cyclopropylmethyloxymethyl)piperidinylmethyl)-4-(S)-(3-thienyl)pyrrolidine;
1-(2,4-Dichlorobenzyl)-3-(S)-(4-(cyclobutylmethyloxymethyl)piperidinylmethyl)-4-(S)-(3-thienyl)pyrrolidine;
1-(2,4-dichlorobenzyl)-3-(S)-(4-(methoxyethyloxymethyl) piperidinylmethyl)-4-(S)-(3-thienyl)pyrrolidine;
1-(2,4-Dichlorobenzyl)-3-(S)-(4-(3-hydroxypropyloxymethyl)piperidinylmethyl)-4-(S)-(3-thienyl)pyrrolidine;
1-(2,4-Dichlorobenzyl)-3-(S)-(4-(3-methoxypropyloxymethyl) piperidinylmethyl)-4-(S)-(3-thienyl)pyrrolidine;
1-(2,4-Dichlorobenzyl)-3-(S)-(4-(3-aminopropyloxymethyl)piperidinylmethyl)-4-(S)-(3-thienyl)pyrrolidine;
1-(2,4-Dichlorobenzyl)-3-(S)-(4-(3-(acetylamino) propyloxymethyl) piperidinylmethyl)-4-(S)-(3-thienyl) pyrrolidine;
1-(2,4-Dichlorobenzyl)-3-(S)-(4-(3-(methylsulfonylamino) propyloxymethyl) piperidinylmethyl)-4-(S)-(3-thienyl) pyrrolidine;
1-(2,4-Dichlorobenzyl)-3-(S)-(4-(hydroxyethyl) piperidinylmethyl)-4-(S)-(3-thienyl)pyrrolidine;
1-(2,4-Dichlorobenzyl)-3-(S)-(4-(methoxyethyl) piperidinylmethyl)-4-(S)-(3-thienyl)pyrrolidine;
1-(2,4-Dichlorobenzyl)-3-(S)-(4-(2-(RS)-hydroxypropyl) piperidinylmethyl)-4-(S)-(3-thienyl)pyrrolidine;
1-(2,4-Dichlorobenzyl)-3-(S)-(4-(2-(RS)-hydroxybutyl) piperidinylmethyl)-4-(S)-(3-thienyl)pyrrolidine;
1-(2,4-Dichlorobenzyl)-3-(S)-(4-(2-(RS)-hydroxypentyl) piperidinylmethyl)-4-(S)-(3-thienyl)pyrrolidine;
1-(2,4-Dichlorobenzyl)-3-(S)-(4-(2-(RS)-hydroxy-3-methylbutyl)piperidinylmethyl)-4-(S)-(3-thienyl) pyrrolidine;
1-(2,4-Dichlorobenzyl)-3-(S)-(4-(2-(RS)-hydroxyhexyl) piperidinylmethyl)-4-(S)-(3-thienyl)pyrrolidine;
1-(2,4-Dichlorobenzyl)-3-(S)-(4-(2-(RS)-hydroxy-4-pentyl) piperidinylmethyl)-4-(S)-(3-thienyl)pyrrolidine;
1-(2,4-Dichlorobenzyl)-3-(S)-(4-(2-(RS)-hydroxypent-4-enyl)piperidinylmethyl)-4-(S)-(3-thienyl)pyrrolidine;
1-(2,4-Dichlorobenzyl)-3-(S)-(4-(2-(RS)-hydroxy-3,3-dimethylbutyl)piperidinylmethyl)-4-(S)-(3-thienyl) pyrrolidine;
1-(2,4-Dichlorobenzyl)-3-(S)-(4-(2-(RS)-methoxybutyl) piperidinylmethyl)-4-(S)-(3-thienyl)pyrrolidine;
1-(2,4-Dichlorobenzyl)-3-(S)-(4-(2-(RS)-methoxypentyl) piperidinylmethyl)-4-(S)-(3-thienyl)pyrrolidine;
1-(2,4-Dichlorobenzyl)-3-(S)-(4-(2-(RS)-methoxy-3-methylbutyl)piperidinylmethyl)-4-(S)-(3-thienyl) pyrrolidine;
1-(2,4-Dichlorobenzyl)-3-(S)-(4-(2-(RS)-methoxyhexyl) piperidinylmethyl)-4-(S)-(3-thienyl)pyrrolidine;
1-(2,4-Dichlorobenzyl)-3-(S)-(4-(2-(RS)-methoxy-4-methylpentyl)piperidinylmethyl)-4-(S)-(3-thienyl) pyrrolidine;
1-(2,4-Dichlorobenzyl)-3-(S)-(4-(2-(RS)-methoxypent-4-enyl)piperidinylmethyl)-4-(S)-(3-thienyl)pyrrolidine;
1-(2,4-Dichlorobenzyl)-3-(S)-(4-(2-ketobutyl) piperidinylmethyl)-4-(S)-(3-thienyl)pyrrolidine;
1-(2,4-Dichlorobenzyl)-3-(S)-(4-(2-ketopentyl) piperidinylmethyl)-4-(S)-(3-thienyl)pyrrolidine;
1-(2,4-Dichlorobenzyl)-3-(S)-(4-(2-(RS)-hydroxy-2-methylpentyl)piperidinylmethyl)-4-(S)-(3-thienyl) pyrrolidine;
1-(2,4-Dichlorobenzyl)-3-(S)-(4-(2-(RS)-methoxy-2-methylpentyl)piperidinylmethyl)-4-(S)-(3-thienyl) pyrrolidine;
1-(2,4-Dichlorobenzyl)-3-(S)-(4-(2-hydroxy-2-propylpentyl)piperidinylmethyl)-4-(S)-(3-thienyl) pyrrolidine;
1-(2,4-Dichlorobenzyl)-3-(S)-(4-(2-methoxy-2-propylpentyl)piperidinylmethyl)-4-(S)-(3-thienyl) pyrrolidine;
1-(2,4-Dichlorobenzyl)-3-(S)-(4-(2-hydroxy-2-methyl-1-propyl)piperidinylmethyl)-4-(S)-(3-thienyl)pyrrolidine;
1-(2,4-Dichlorobenzyl)-3-(S)-(4-(2-methoxy-2-methyl-1-propyl)piperidinylmethyl)-4-(S)-(3-thienyl)pyrrolidine;
1-(2,4-Dichlorobenzyl)-3-(S)-(4-(2-methoxy-1-propyl) piperidinylmethyl)-4-(S)-(3-thienyl)pyrrolidine;
1-(2,4-Dichlorobenzyl)-3-(S)-(4-(2-allyloxy-2-methyl-1-propyl)piperidinylmethyl)-4-(S)-(3-thienyl)pyrrolidine;
1-(2,4-Dichlorobenzyl)-3-(S)-(4-(2-n-propyloxy-2-methyl-1-propyl)piperidinyl-methyl)-4-(S)-(3-thienyl)pyrrolidine;
1-(2,4-Dichlorobenzyl)-3-(S)-(4-(2-hydroxy-2-ethyl-1-butyl)piperidinylmethyl)-4-(S)-(3-thienyl)pyrrolidine;
1-(2,4-Dichlorobenzyl)-3-(S)-(4-(2-methoxy-2-ethyl-1-butyl)piperidinylmethyl)-4-(S)-(3-thienyl)pyrrolidine;
1-(2,4-Dichlorobenzyl)-3-(S)-(4-(2-ethoxy-2-methyl-1-propyl)piperidinylmethyl)-4-(S)-(3-thienyl)pyrrolidine;
1-(2,4-Dichlorobenzyl)-3-(S)-(4-(2-allyloxy-1-propyl) piperidinylmethyl)-4-(S)-(3-thienyl)pyrrolidine;
1-(2,4-Dichlorobenzyl)-3-(S)-(4-(2-ethoxy-1-propyl) piperidinylmethyl)-4-(S)-(3-thienyl)pyrrolidine;
1-(2,4-Dichlorobenzyl)-3-(S)-(4-(2-(3-hydroxy-1-propyl) oxy-2-methyl-1-propyl)piperidinylmethyl)-4-(S)-(3-thienyl)pyrrolidine;
1-(2,4-Dichlorobenzyl)-3-(S)-(4-(2-(3-hydroxy-1-propyl) oxy-1-propyl)piperidinylmethyl)-4-(S)-(3-thienyl) pyrrolidine;
1-(2,4-Dichlorobenzyl)-3-(S)-(4-(2-cyclopentyl-2-hydroxyethyl) piperidinylmethyl)-4-(S)-(3-thienyl) pyrrolidine;
1-(2,4-Dichlorobenzyl)-3-(S)-(4-(2-cyclohexyl-2-hydroxyethyl) piperidinylmethyl)-4-(S)-(3-thienyl) pyrrolidine;
1-(2,4-Dichlorobenzyl)-3-(S)-(4-(2-cyclobutyl-2-hydroxyethyl) piperidinylmethyl)-4-(S)-(3-thienyl) pyrrolidine;
1-(2,4-Dichlorobenzyl)-3-(S)-(4-(2-cycloheptyl-2-hydroxyethyl) piperidinylmethyl)-4-(S)-(3-thienyl) pyrrolidine;
1-(2,4-Dichlorobenzyl)-3-(S)-(4-(2-(4-tetrahydropyranyl)-2-hydroxyethyl) piperidinylmethyl)-4-(S)-(3-thienyl) pyrrolidine;

1-(2,4-Dichlorobenzyl)-3-(S)-(4-(2-(N-methyl-4-piperidinyl) -2-hydroxyethyl) piperidinylmethyl)-4-(S)-(3-thienyl)pyrrolidine;
1-(2,4-Dichlorobenzyl)-3-(S)-(4-(2-cyclopentyl-2-methoxyethyl) piperidinylmethyl)-4-(S)-(3-thienyl) pyrrolidine;
1-(2,4-Dichlorobenzyl)-3-(S)-(4-(2-cyclopentyl-2-allyloxyethyl) piperidinylmethyl)-4-(S)-(3-thienyl) pyrrolidine;
1-(2,4-Dichlorobenzyl)-3-(S)-(4-(2-cyclobutyl-2-methoxyethyl) piperidinylmethyl)-4-(S)-(3-thienyl) pyrrolidine;
1-(2,4-Dichlorobenzyl)-3-(S)-(4-(2-cyclobutyl-2-allyloxyethyl) piperidinylmethyl)-4-(S)-(3-thienyl) pyrrolidine;
1-(2,4-Dichlorobenzyl)-3-(S)-(4-(2-cyclobutyl-2-benzyloxyethyl)piperidinylmethyl)-4-(S)-(3-thienyl) pyrrolidine;
1-(2,4-Dichlorobenzyl)-3-(S)-(4-(2-cyclohexyl-2-methoxyethyl) piperidinylmethyl)-4-(S)-(3-thienyl) pyrrolidine;
1-(2,4-Dichlorobenzyl)-3-(S)-(4-(2-cyclohexyl-2-allyloxyethyl) piperidinylmethyl)-4-(S)-(3-thienyl) pyrrolidine;
1-(2,4-Dichlorobenzyl)-3-(S)-(4-(2-cyclohexyl-2-benzyloxyethyl) piperidinylmethyl)-4-(S)-(3-thienyl) pyrrolidine;
1-(2,4-Dichlorobenzyl)-3-(S)-(4-(2-(4-tetrahydropyranyl)-2-methoxyethyl) piperidinylmethyl)-4-(S)-(3-thienyl) pyrrolidine;
1-(2,4-Dichlorobenzyl)-3-(S)-(4-(2-(4-tetrahydropyranyl)-2-allyloxyethyl) piperidinylmethyl)-4-(S)-(3-thienyl) pyrrolidine;
1-(2,4-Dichlorobenzyl)-3-(S)-(4-(2-(4-tetrahydropyranyl)-2-benzyloxyethyl) piperidinylmethyl)-4-(S)-(3-thienyl) pyrrolidine;
and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing spiro-substituted azacycles as modulators of chemokine receptor activity. In particular, these compounds are useful as modulators of the chemokine receptors, including CCR-3 and/or CCR-5.

The utility of the compounds in accordance with the present invention as modulators of chemokine receptor activity may be demonstrated by methodology known in the art, such as the assay for CCR-5 binding as disclosed by Van Riper, et al., *J. Exp. Med.*, 177, 851-856 (1993), and the assay for CCR-3 binding as disclosed by Daugherty, et al., *J. Exp. Med.*, 183, 2349-2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a $CCR^3$ transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887-4892 (1991).

In particular, the compounds of the following examples had activity in binding to the CCR-3 or the CCR-5 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata,* Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-3 and/or CCR-5. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-3 and/or CCR-5. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-3 or CCR-5, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H$_2$-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxyephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelio- ration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (Hi-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), oc-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |

-continued

| Drug Name | Manufacturer | Indication |
|---|---|---|
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (−) 6-Chloro-4(S)-cyclopropyl-ethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz, DMP-266 | DuPont-Merck Pharmaceuticals | HIV infection, AIDS, ARC (non-nucleoside reverse transcriptase inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphono-formate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony | Schering-Plough | AIDS, combination w/AZT |

-continued

| Drug Name | Manufacturer | Indication |
|---|---|---|
| Stimulating Factor | | |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/ sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

-continued

| Drug Name | Manufacturer | Indication |
|---|---|---|
| OTHER | | |
| Daunorubicin | NeXstar, Sequus Ortho Pharm. Corp. | Karposi's sarcoma |
| Recombinant Human Erythropoietin | | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of IV protease and/or a non-nucleoside inhibitor of HIV reverse transcriptase. An optional fourth component, in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2 (R)-phenylmethyl-4-(S)-hydroxy-5-(1-(4-(2-benzo[b]furanylmethyl)-2(S)-N'(t-butylcarboxamido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2 (S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3, 1-benzoxazin-2-one, and, optionally, AZT and/or 3TC and/or ddI and/or ddC; (2) indinavir, and any of AZT and/or ddI and/or ddC.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over, a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

Several methods for preparing the compounds of this invention are illustrated in the following Schemes and Examples.

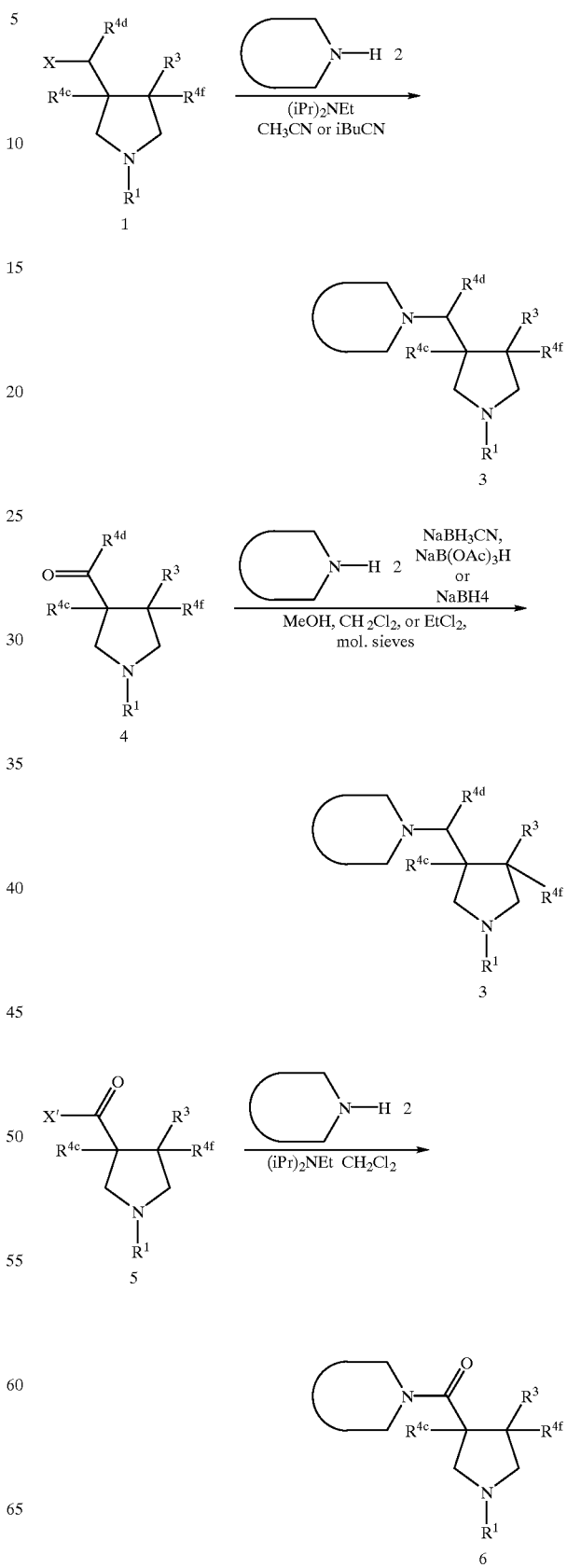

-continued

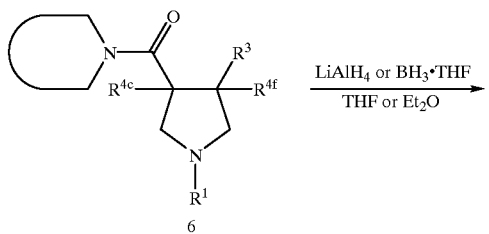
6

LiAlH₄ or BH₃·THF
THF or Et₂O

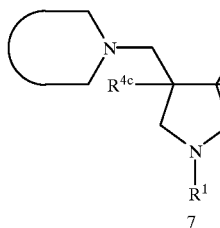
7

In one protocol, the compounds of the present invention are prepared by alkylating heterocycle 1 (wherein X is a leaving group such as, for example, bromide, iodide, methanesulfonate, p-toluenesulfonate, trifluoromethanesulfonate) with cyclic amine 2 under appropriate conditions to provide compound 3. Cyclic amine 2 is available commercially or can be prepared using the methods given below.

Alternatively, heterocycle 4, bearing a carbonyl group, can be combined with the cyclic amine 2 and the intermediate imine or iminium species is reduced to tertiary amine 3 under homogenous conditions (e.g. using sodium cyanoborohydride, sodium borohydride, or sodium triacetoxyborohydride) or in the presence of hydrogen and a heterogeneous catalyst (e.g. palladium on carbon or Raney nickel).

In an alternative embodiment of the present invention, heterocycle 5, bearing an activated acyl side chain (wherein X', for example, is a chloride or bromide atom, or is a hydroxybenzotriazole residue from activation of the corresponding carboxylic acid with HOBt in the presence of a suitable carbodiimide) is allowed to react with cyclic amine 2 to provide the corresponding tertiary amide 6. Compound 6 can then be treated with a suitable reducing agent (e.g. diborane; borane in THF; borane dimethylsulfide, or lithium aluminum hydride) to provide the desired product 7.

SCHEME 2

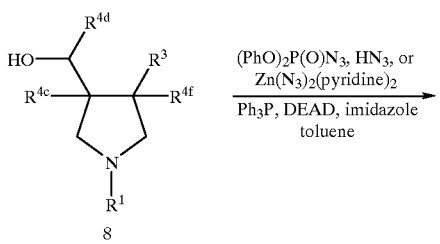
8

(PhO)₂P(O)N₃, HN₃, or
Zn(N₃)₂(pyridine)₂
―――――――――――――
Ph₃P, DEAD, imidazole
toluene -continued

9

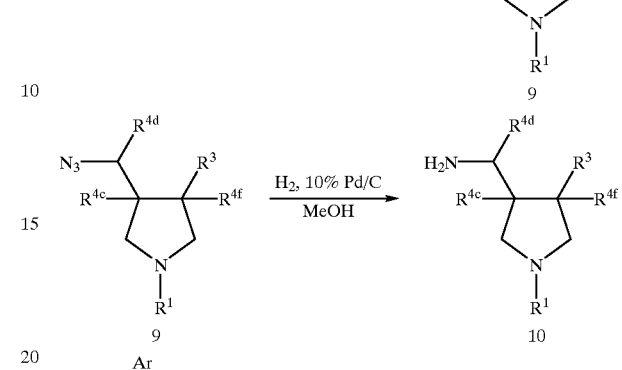

H₂, 10% Pd/C
―――――――
MeOH

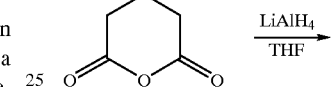
10

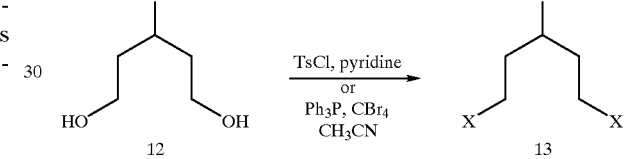

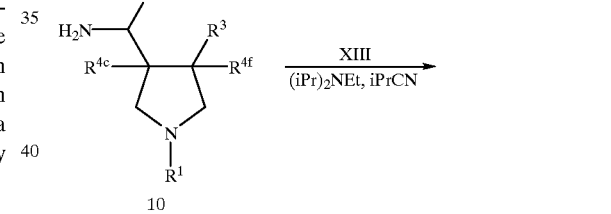

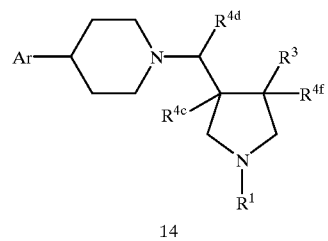
14

An alternative preparation of the target compounds is carried out as shown in Scheme 2. Treatment of alcohol 8 with zinc azide bis(pyridine) complex in the presence of triphenylphosphine and diethyl azodicarboxylate, or with diphenylphosphoryl azide, or with hydrazoic acid, provides azide 9. Reduction of 9, for example, with hydrogen and palladium on carbon, affords primary amine 10. This amine can be doubly alkylated with a bis-electrophile such as 13 under basic conditions, to provide the compound 14. Bis-electrophiles can be prepared from substituted glutaric anhydride derivatives such as 11 by reduction to diol 12 followed by double activation, using, for example, p-toluenesulfonyl chloride in pyridine, or tiriphenylphosphine carbon tetrabromide in acetonitrile, to provide 13 (where X=Br or OTs).

SCHEME 3

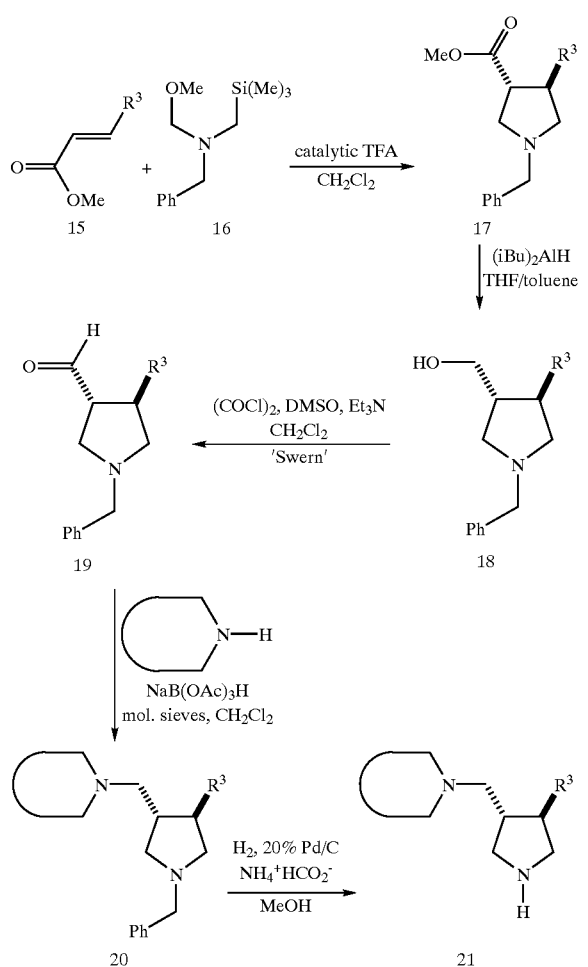

SCHEME 4

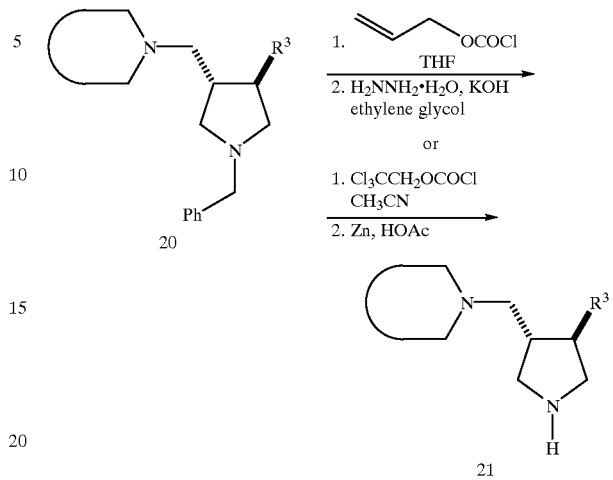

In cases when certain substituents are labile to hydrogenolysis conditions, alternative methods to remove the benzyl group of compound 20 are described in Scheme 4. Compound 20 may be converted to the allyloxycarbamate derivative by stirring with allylchloroformate at rt in a solvent such as TBF (T. Shono, Y. Matsumura, J. Org. Chem., 1984, 48, 300) Subsequent reaction with hydrazine hydrate and KOH in ethylene glycol at elevated temperatures provides the amine 21. Compound 20 may also be converted to its 2,2,2,-trichloroethyloxy-carbamate derivative by stirring with 2,2,2-trichloroethylchloroformate in a solvent such as acetonitrile (V. H. Rawal, R. J. Jones, J. Org. Chem., 1987, 52, 19). This derivative is then converted to amine 21 by reaction with zinc powder in acetic acid a slightly elevated temperatures such as at 40° C.

The preparation of compounds within the scope of the instant invention which bear a 1,3,4-trisubstituted pyrrolidine framework is detailed in Scheme 3. Treatment of a trans-cinnamic ester such as 15 with N-benzyl-N-methoxymethyl-N-(trimethylsilyl)-methylamine (16) in the presence of a catalytic amount of an acid such as TFA, titanium tetrafluoride lithium fluoride or cesium fluoride according to the procedure of Padwa et al (J. Org. Chem. 1987, 52, 235) preferentially affords the 3,4-trans pyrrolidine 17. Executing this sequence starting from the cis-cinnamic ester results in preferential formation of the 3,4-cis pyrrolidine. Reduction of ester 17 with diisobutylaluminum hydride, lithium aluminium hydride, or sodium bis(2-methoxyethoxy)aluminum hydride, provides the primary alcohol 18. Oxidation of 18 to the aldehyde 19 can be carried out under numerous conditions, such as with the Swern reaction, with DMSO and oxalyl chloride at low temperature, followed by triethylamine, or with various chromium trioxide-based reagents (see March J. "Advanced Organic Chemistry", 4th ed., John Wiley & Sons, New York, pp. 1167-1171 (1992)). Reductive amination with cyclic amine 2 provides diamine 20. Alternatively, The N-benzyl group is cleaved in a hydrogen atmosphere in the presence of 10% palladium on carbon or with Pearlmans' catalyst [Pd(OH)$_2$/C] to provide the secondary amine 21.

SCHEME 5

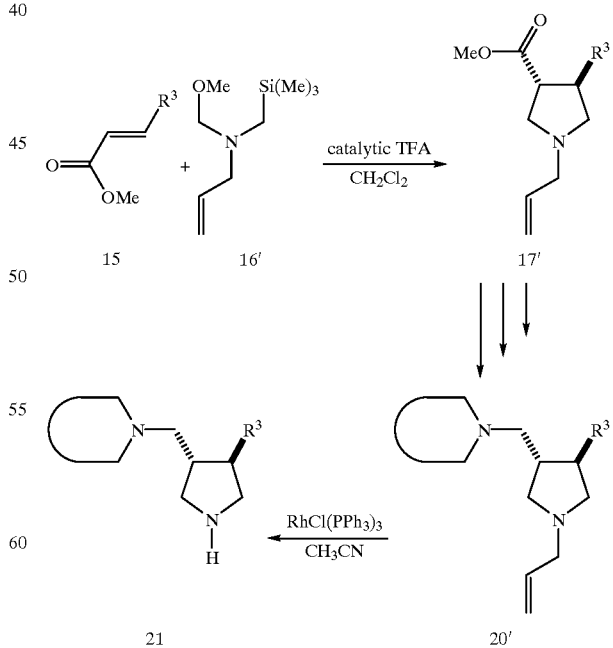

Scheme 5 describes a modification of Scheme 3 when substituents are not compatible with hydrogenolysis of the benzyl group of compound 20. In this variation, treatment of a trans-cinnamic ester 15 with N-allyl-N-methoxymethyl-N-(trimethylsilyl)-methylamine (16') according to procedures described in Scheme 3 provides N-allylpyrrolidine derivative 17'. The reagent N-allyl-N-methoxymethyl-N-(trimethylsilyl)-methylamine is prepared after procedures described by Padwa et al (*J. Org. Chem.* 1985, 50, 4006 and *J. Org. Chem.* 1987, 52, 235) Subsequent elaboration as described in Scheme 3 gives compound 20'. The allyl group is removed by stirring compound 20' with a catalytic amount of Wilkinson's catalyst [RhCI(PPh$_3$)$_3$] in a solvent such as acetonitrile as described by Laguzza et. al. (Tetrahedron Letters 1981, 22, 1483). Alternatively, Pd(0) catalysts can be utilized as described by Lemaire-Audoire et. al. (Tetrahedron Letters 1995, 36, 1267).

SCHEME 7

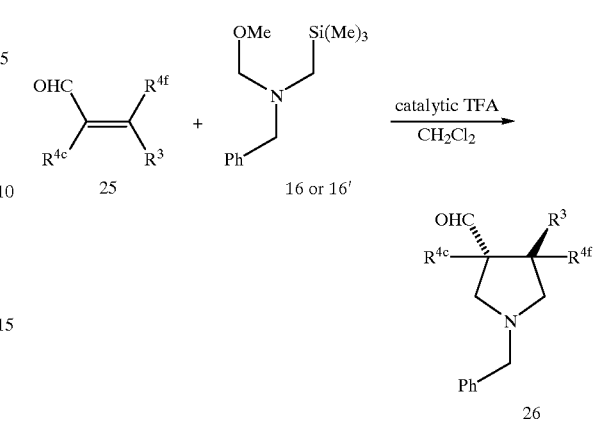

Compounds possessing geminal substituents on positions 3 or 4 (or on both C3 and C4) of the pyrrolidine ring are prepared by the method shown in Scheme 7. Cycloaddition of unsaturated aldehyde 25 with reagent 16 or 16' as described in Schemes 3 or 5 provides pyrrolidine aldehyde 26. Further elaboration of 26 can be achieved as described in the previous Schemes.

SCHEME 6

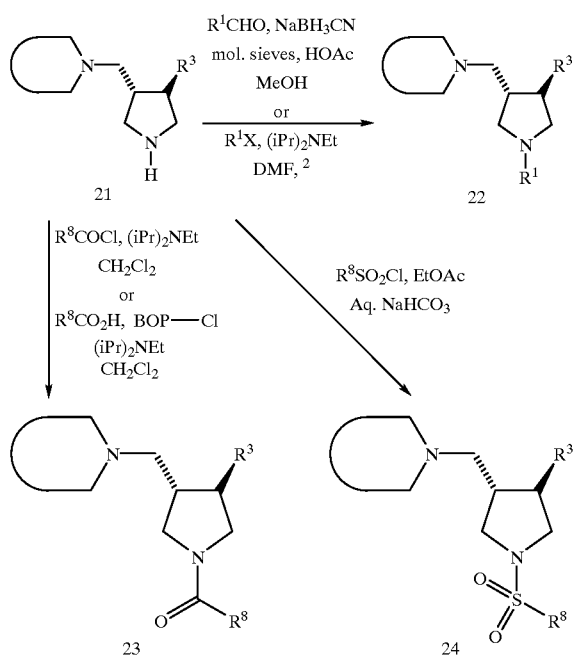

SCHEME 8

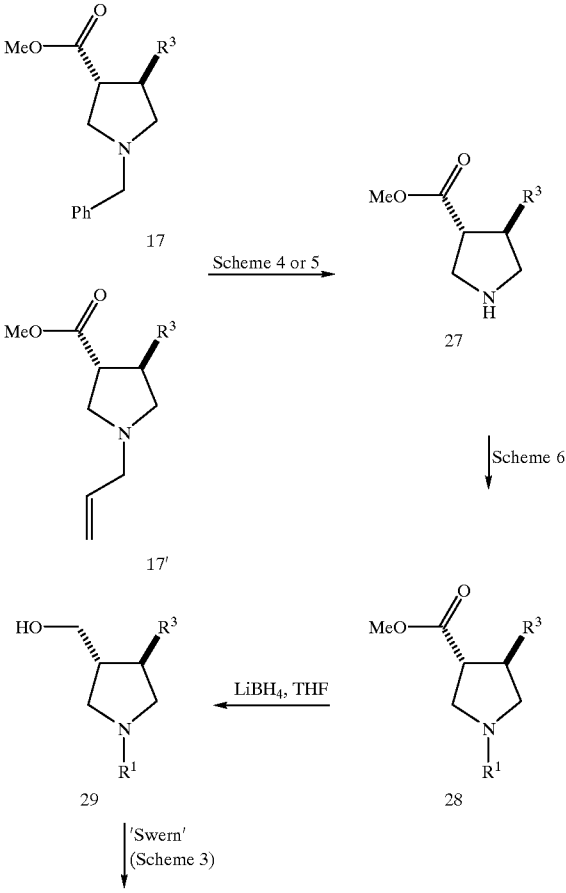

The unsubstituted pyrrolidine 21 may be further functionalized as shown in Scheme 6. Reductive amination with suitable aldehydes under standard conditions provides the tertiary amine 22. The pyrrolidine nitrogen may be alkylated with a suitable halide, methanesulfonate, p-toluenesulfonate, etc. carried out under standard conditions to provide N-alkylated pyrrolidine 22. Alternatively, compound 22 is acylated with, for example, acid chlorides or bromides, or activated esters utilizing a variety of the standard coupling conditions to give amide 23. For example, reaction of compound 22 and a carboxylic acid with BOP-Cl and triethylamine in a solvent such as methylene chloride is a commonly used procedure. The sulfonamide 24 is prepared under standard conditions by exposing 21 to an alkyl or aryl sulfonyl chloride in the presence of a suitable base to neutralize the formed hydrogen chloride.

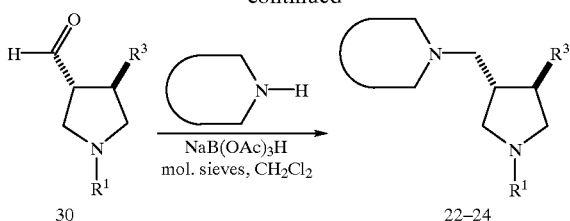

An alternative approach to the synthesis of chemokine modulators is described in Example 8. Ester derivatives 17 (Scheme 3) or 17' (Scheme 5) are first debenzylated or deallylated by procedures described in Schemes 3, 4 or 5 to give secondary amine derivative 27. Compound 27 can then be elaborated as described in Scheme 6 to provide compound 28. The ester group of 28 can be selectively reduced with a reagent such as lithium borohydride in THF to give the alcohol 29 which is then converted to aldehyde 30 under Swern conditions as described in Scheme 3. Aldehyde 39 is then converted to derivative 22 (or 23 or 24) by reductive amination (Scheme 3).

SCHEME 9

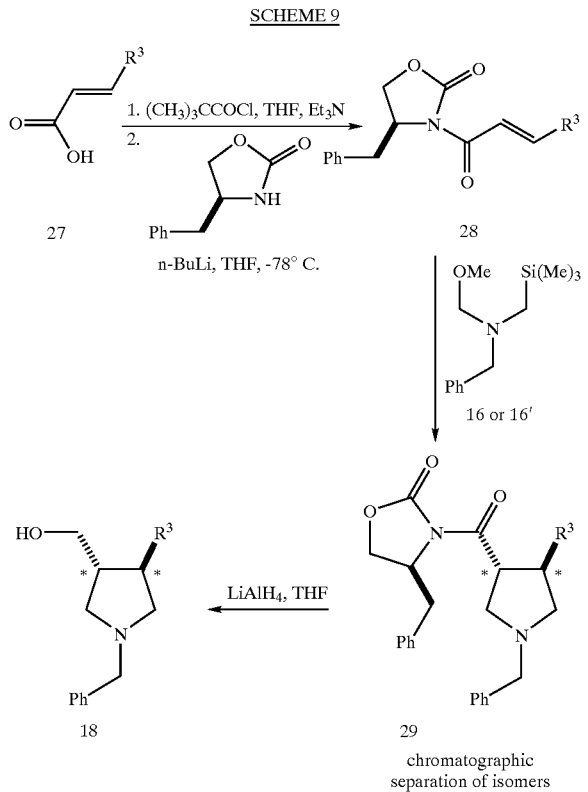

The preparation of optically active compounds described in Scheme 9 follows procedures described by Ma et.al., (*Tetrahedron: Assymmetry* 1997, 8, 883). Reaction of a trans-acrylic acid with oxalyl chloride or pivaloyl chloride and triethylamine in THF provide the mixed anhydride intermediate. This is then treated with the lithium salt of an appropriate chiral auxiliary such as (S)-benzyl-2-oxazolidinone in THF at reduced temperatures, such as −78° C. to give amide 28. This acrylamide is then reacted with N-benzyl-N-methoxymethyl-N-(trimethylsilyl)-methylamine (16) or N-allyl-N-methoxymethyl-N-(trimethylsilyl)-methylamine (16') as described in Schemes 3 and 5, respectively, to give pyrrolidine intermediate 29 or the corresponding N-allyl derivative. Modest diastereoselectivity is achieved in these cyclizations as shown by Ma et al. However, the separate optically active isomers may be easily obtained by simple chromatography on silica gel. Reaction of the selected diastereomer 29 with LiAlH$_4$ in THF at 0° C. provides the optically active version of compound 18 which is further elaborated as described in the previous Schemes The various piperidine derivatives, when not commercially available, are prepared as described in the following Schemes.

SCHEME 10

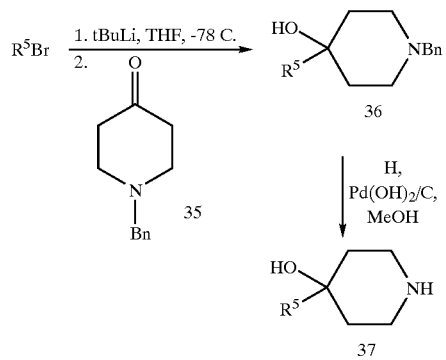

A method of preparing 4-alkyl-4-hydroxypiperidine derivatives is described in Scheme 10. A suitable 3-alkyl halide 34 in TBF at −78° C. is reacted with a base such as t-butyl lithium. This is then reacted with a protected 4-piperidone derivative such as N-benzyl-4-piperidone 35 to give the arylpropylpiperidine derivative 36. Other nucleophile reagents such as Grignard reagents (R$^5$MgX) may also be utilized. Deprotection by hydrogenation with Pd(OH)$_2$/C (Pearlman's catalyst) gives piperidine derivative 37 which can be reacted with compound 19 as described in Scheme 3.

SCHEME 11

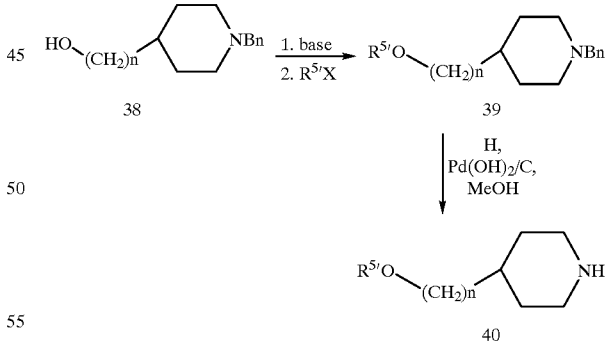

A method of preparing 4-alkyloxyalyylpiperidine derivatives is described in Scheme 11. An hydroxyalkylpiperidine derivative 38 is reacted with a base such as but not limited to sodium hydride in a such such as DMF. This alkoxide is then treated with an electrophile R$^{5'}$X wherein X is a leaving group such as bromide, iodide, chloride, methanesulfonate, p-toluenesulfonate, trifluoromethanesulfonate to give ether 39. Varians on his Williamson reaction are reviewed in March J. "Advanced Organic Chemistry", 4th ed., John Wiley & Sons, New York, pp. 354, 386 (1992). If the proecting group on the piperidine nitrogen is benzyl as is the case with 39, it is removed by hydrogenation or as described in Reaction Schemes 3 and 4 to give the corresponding piperidine derivative 40. An alternate protecting group such as the t-butoxycarboyl (BOC) group is removed with trifluoro acetic acid.

SCHEME 12

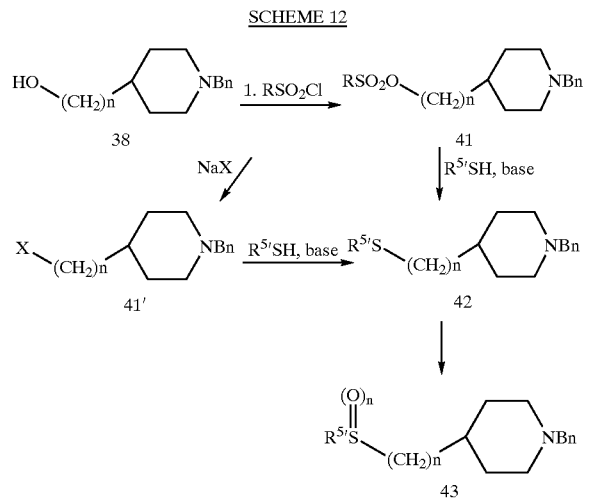

Thioether derivatives are prepared under Williamson-type conditions (see March J. "Advanced Organic Chemistry", 4th ed., John Wiley & Sons, New York, pp. 407 (1992)). Compound 38 is converted to an electrophile by converting the hydroxy group to a leaving group such as compound 41 (methanesulfonate, p-toluenesulfonate, trifluoromethanesulfonate) or 41' (bromide, iodide). Then compound 41 or 41' is reacted with a thiolate anion prepared from an alkyl thiol and an appropriate base. Thioether 42 can be converted to sulfoxide or sulfone derivatives 43 as described in March J. "Advanced Organic Chemistry", 4th ed., John Wiley & Sons, New York, pp. 1201 (1992).

SCHEME 13

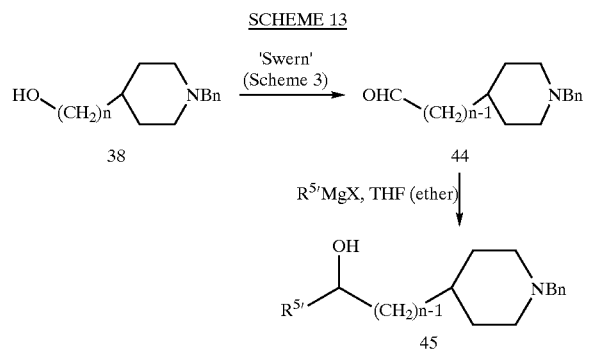

In Scheme 13, the preparation of 4-(3-alkyl-2-hydroxyalkyl) piperidines is described. Compound 38 is converted to aldehyde 44 by the Swern-type conditions (Reaction Scheme 3). Reaction of compound 44 with Grignard reagents or other related nucleophiles gives hydroxy derivative 45. Compound 45 is then deprotected.

SCHEME 14

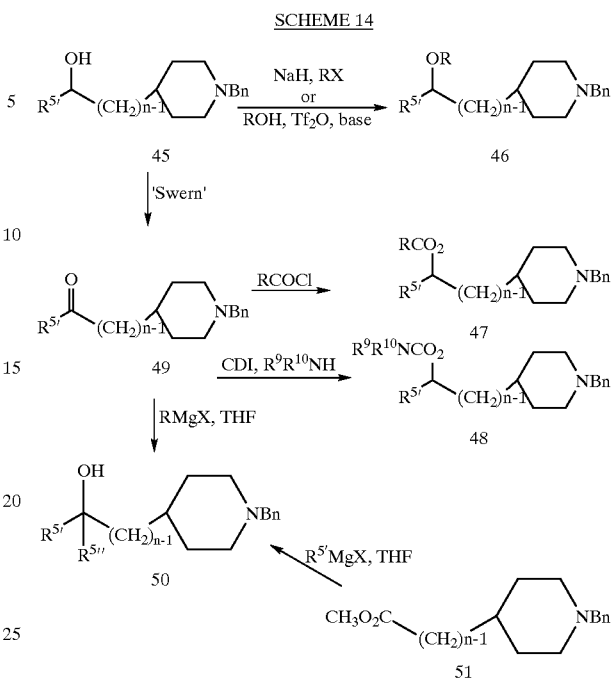

Compound 45 can be further derivatized as depicted in Scheme 14. Ether derivatives 46 can be prepared by reaction of 45 with an alkylhalide, methanesulfoate, tosylate or triflate in the presence of a base such as sodium hydride in an aprotic inert solvent such as TBF. Alternatively, an excess of silver oxide ($Ag_2O$) is used in place of the base. In an example, reaction of an alcohol with trifluoromethane sulfonic anhydride ($Tf_2O$, triflic anhydride) in dichloromethane at reduced temperature, preferably −78° C. gives the pre-formed triflate. To this solution is added compound 4, the reaction mixture is warmed to room temperature and stirring is continued until reaction is complete.

Esters (compound 47) can be prepared by reaction of a pre-formed carboxylic acid chloride with compound 45 in a basic solvent such as pyridine or triethylamine. The acid chlorides, when not purchased, are prepared by stirring the carboxylic acids in reagents such as oxalyl chloride or thionyl chloride. C4 sulfonate, derivatives are prepared in a similar manner by reaction with sulfonyl chlorides.

C4 carbamate and carbonate derivatives (compound 48) are prepared by first reacting compound 45 with carbonyldiimidazole (CDI) to obtain the imidazolecarbonyl intermediate which is then reacted with an amine ($R^9R^{10}NH$) or an alcohol to give the corresponding carbonate or carbamate derivatives.

Compound 45 can be oxidized to the corresponding ketone 50 by any number of standard conditions including the Swern reaction conditions. It can then be reacted with Grignard reagents or related nucleophiles (as in Scheme 14) to give the tertiary hydroxy derivative 50. This alcohol can then be further modified as described in this scheme. Symmetrically substituted secondary alcohol derivatives of compound 50 can be obtained by reacting an ester derivative 51 with excess Grignard reagent.

SCHEME 15

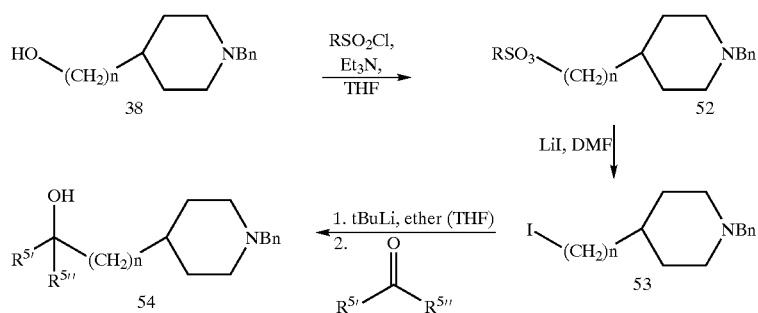

An alternate preparation of secondary alcohols such as compound 50 (Scheme 14) is demonstrated in Scheme 15. Alcohol 38 is converted to a methanesulfoate, tosylate or triflate 52 according to procedures described in earlier Schemes. Compound 52 is then converted to iodide 53 by reaction with Lithium iodide in a solvent such as THF or DMF usually at elevated temperatures. Reaction with iodide 53 with t-butyl lithium in a solvent such as ether or THF at low temperatures (−78° C.) gives the carbanion which, inturn, is reacted with a ketone or aldehyde ($R^{5'}COR^{5''}$) to give alcohol 54.

In some cases the order of carrying out the foregoing reaction schemes may be varied to facilitate the reaction or to avoid unwanted reaction products. The following examples are provided for the purpose of further illustration only and are not intended to be limitations on the disclosed invention.

EXAMPLE 1

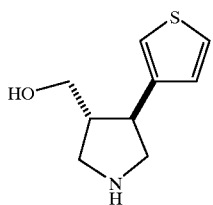

3-(SR)-Hydroxymethyl-4-(RS)-(3-thienyl)pyrrolidine

Step 1: N-Allyl-N-(trimethylsilylmethyl)amine

To 118 mL (1.57 mol) of allylamine warmed at 40° C. in an inert atmosphere was very slowly added 100 mL (0.72 mol) of chloromethyl trimethylsilane (approximate rate of 1 mL/min). The reaction mixture was slowly warmed to 70° C. and stirred for 24 h. The reaction mixture was cooled to 0° C. and to it was added water to break up the gel and then 300 mL of 2N NaOH solution. The reaction mixture was extracted with ether. The combined organic fractions were washed with 500 mL of sat'd NaCl solution, dried over $Na_2SO_4$, filtered and the filtrate was concentrated. The residue was purified by distillation (bp 80-84° C. at 100 torr) to give 75 g of the title compound.

Step 2. N-Allyl-N-(methoxymethyl)-N-trimethylsilylmethyl)amine

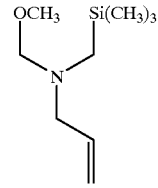

To 75 g (0.57 mol) of N-allyl-N-(trimethylsilylmethyl) amine at 0° C. was slowly added 67 mL (0.88 mol) of aqueous formaldehyde (37% w/w). After stirring for 5 min, 65 mL (1.6 mol) of methanol was added followed by the addition of 94 g (0.68 mol) of $K_2CO_3$. The reaction mixture was warmed to rt and stirred for 12 h. The reaction mixture was partitioned between 300 mL of water and 300 mL of ether. The organic fraction was washed with water and sat. NaCl solution. The combined aqueous fractions were extracted with ether. The combined organic fractions were dried over $Na_2SO_4$, filtered and the filtrate was concentrated to give 89 g of the title compound which was used without further purification.

Step 3: Methyl-3-(3-thienyl)acrylate

To a solution of 5.1 g (33 mmol) of 3-(3-thienyl)acrylic (Aldrich) in 75 mL of methanol at rt was slowly added 4.8 mL (66 mmol) of thionyl chloride and the reaction mixture was stirred at reflux for 2.5 h. The reaction mixture was concentrated, redissolved in methylene chloride ($CH_2Cl_2$), washed with $NaHCO_3$, dried over $MgSO_4$, filtered though a pad of silica and evaporated to give 6.7 g of the title compound as a off-white solid which was used without further purification. $^1H$ NMR ($CDCl_3$) δ 7.69 (d, 1H, J=16.0 Hz), 7.51 (d, 1H, J=2.8 Hz), 7.35 (d of d, 1H, J=5.2, 2.9 Hz), 7.31 (d, 1H, J=5.1 Hz), 6.28 (d, 1H, J=15.8 Hz), 3.81 (s, 3H).

Step 4. 1-Allyl-3-(SR)-carbomethoxy-4-(RS)-(3-thienyl) pyrrolidine

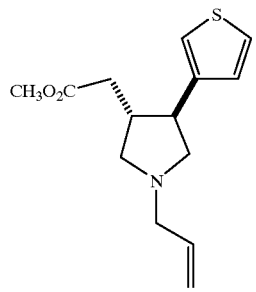

To a solution of 5 g (29.7 mmol) of methyl-3-(3-thienyl) acrylate, 11.3 g (60.3 mmol) of N-allyl-N-(methoxymethyl)-N-trimethyl silylmethyl)amine in 50 mL of CH₂Cl₂ at 0° C. was added 0.3 mL of trifluoroacetic acid and the reaction mixture was stirred for 4 h while warming to rt. The reaction mixture was diluted with sat'd NaHCO₃ and extracted twice with 100 mL of ether. The combined organic fractions were washed with sat'd NaHCO₃ and NaCl solutions, dried over Na₂SO₄, filtered and the filtrate was concentrated. The residue was purified by chomatography (silica, EtOAc:hexanes, 1:3) to give 7.3 g of the title compound.

Step 5. 1-Allyl-3-(SR)-hydroxymethyl-4-(RS)-(3-thienyl) pyrrolidine

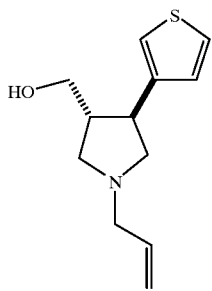

To a solution of 6.1 g (24.5 mmol) of 1-allyl-3-(SR)-carbomethoxy-4-(RS)-(3-thienyl)pyrrolidine in 50 mL of TMF at 0° C. was added 49 mL (49 mmol) of a 1 M solution of lithium aluminum hydride in THF and the reaction was stirred at rt for 12 h. To the reaction mixture was then added 5 mL of water and 5 mL of 2N NaOH. The reaction mixture was extracted with ethyl acetate and the combined organic fractions were washed with sat'd NaCl solution, dried over Na₂SO₄, filtered and the filtrate was concentrated to give the title compound which was used without further purification. Mass spectrum (ESI) m/e=274 (M+1).

Step 6. 3-(SR)-hydroxymethyl-4-(RS)-(3-thienyl) pyrrolidine

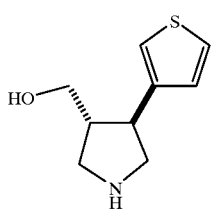

A mixture of 3.5 g (15.7 mmol) of 1-allyl-3-(SR)-hydroxymethyl-4-(RS)-(3-thienyl)pyrrolidine and 400 mg (0.43 mmol) of Wilkinson's catalyst [Rh(PPh₃)₃Cl] in 200 mL of an 85% solution of CH₃CN and water was heated to 90° C. and stirred for 3 h. The reaction mixture was cooled to rt and concentrated to give the title compound which was used without further purification.

EXAMPLE 2

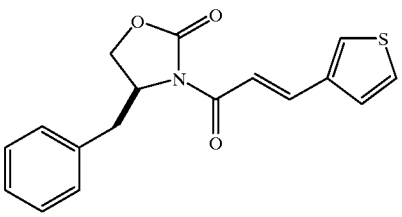

3-(R)-Hydroxymethyl-4-(S)-(3-thienyl)pyrrolidine

Step 1. N-trans-3-(3-Thienyl)acryloyl-4-(S)-benzyl-2-oxazolidinone

To a solution of 5 g (34 mmol) of 3-(3-thienyl)acrylic acid and 5.5 mL (39.7 mmol) of triethylamine in 160 mL of TEF at 0° C. was added 6.15 g (34.7 mmol) of pivaloyl chloride. The reaction mixture was allowed to warm to rt and was stirred for 2 h, then was cooled to −78° C.

Meanwhile, to a solution of 6.15 g (34.7 mmol) of (S)-benzyl-2-oxazolidinone in 60 mL of THF at −78° C. under nitrogen, was added 2.48 mL of nbutyllithium (1.6M, 39.7 mmol) and the solution was stirred for 30 min at −78° C. This was added via cannula to the first solution. After addition was complete, the solution was allowed to warm to room temperature for 2 h.

The reaction was quenched by addition of saturated aqueous NH₄Cl and the mixture was extracted with ethyl acetate. The organic layer was washed with brine, dried over MgSO₄, and filtered. The solution was concentrated and the residue was crystalized from hexanes to afford 8.43 g the title compound; 1H NMR (CDCl3) δ 7.92 (d, 1H, J=15.5 Hz), 7.76 (d, 1H, J=15.5 Hz), 7.62 (d, 1H, J=1.9 Hz), 4.79–4.83 (m, 1H)₄.₂₀₋₄.₂₇ (m, 3H), 3.38 (d of d, 1H, J=13.5, 3.2 Hz), 2.87 (d of d, 1H, J=13.3, 9.4 Hz); Mass spectrum (ESI) m/e=435 (M+1).

Step 2. (S)-N-(1-Allyl-4-(S)-(3-thienyl)-3-(R)-pyrrolidinylcarbonyl)-4-benzyl-2-oxazolidinone and (S)-N-(1-Allyl-4-(R)-(3-thienyl)-3-(S)-pyrrolidinylcarbonyl)-4-benzyl-2-oxazolidinone

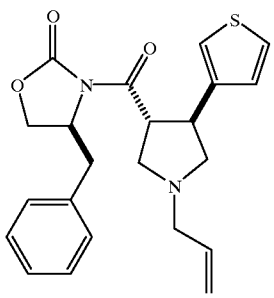

To a solution of 226 g (0.72 mol) of N-trans-3-(3thienyl) acryloyl-4-(S)-benzyl-2-oxazolidinone (Step 1) in 2.5 L of CH$_2$Cl$_2$ at −8° C. was added 202 g (1.08 mol) of N-allyl-N-(methoxymethyl)-N-trimethylsilylmethyl)amine. Then 8 mL (107 mmol) of trifluoroacetic acid was added and the solution was stirred at rt for 23 h. The solution was poured into 1.5 L of saturated NaHCO$_3$ solution, the mixture was stirred vigorously for 15 min, and the layers were separated. The aqueous layer was washed with CH$_2$Cl$_2$ and the combined organic fractions were washed with brine, dried over MgSO$_4$, filtered, and the filtrate was concentrated. the residue was purified by chromatography (silica, ethyl acetate:hexanes, 1:4) to afford the title compound (S)-N-[(1-allyl)-4-(S)-(3-thienyl)-3-(R)-pyrrolidinylcarbonyl]-4-benzyl-2-oxazolidinone. Mass spectrum (ESI) m/e=274 (M+1).

Futher elution afforded the title compound (S)-N-[(1-allyl)-4-(R)-(3-thienyl)-3-(S)-pyrrolidinylcarbonyl]-4-benzyl-2-oxazolidinone; (ESI) m/e=274 (M+1).

Step 3. 1-Allyl-3-(R)-hydroxymethyl-4-(S)-(3-thienyl) pyrrolidine

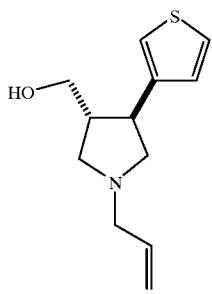

To a solution of 136 g (343 mmol) of (S)-N-[(1-allyl)-4-(S)-(3-thienyl)-3-(R) pyrrolidinylcarbonyl)]-4-benzyl-2-oxazolidinone (Step 2) in 1.5 L of THF at 10° C. was added 690 mL (690 mmol) of a solution of LiAlH$_4$ (1.0 M in THF). The solution was stirred at room temperature for 18 h, then was quenched by addition of 90 mL of a sat'd Na$_2$SO$_4$ solution. The solids were filtered and washed with ether. The filtrate and washings were combined, dried over Na$_2$SO$_4$, filtered, and the filtrate concentrated. The residue was purified by chromatography (silica, acetone:hexanes, 1:6, then 3% methanol in CH$_2$Cl$_2$) to afford the title compound. Mass spectrum (ESI) m/e=224 (M+1); [a]D=+29.9 (c.=1.50, CHCl$_3$).

Step 4. 3-(R)-Hydroxymethyl-4-(S)-(3-thienyl)pyrrolidine

The title compound was prepared from 1-allyl-3-(R)-hydroxymethyl-4-(S)-(3-thienyl)pyrrolidine as described in Example 1, Step 6.

EXAMPLE 3

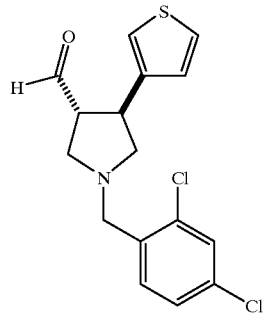

1-(2,4-Dichlorobenzyl)-3-(R)-formyl-4-(S)-(3-thienyl) pyrrolidine

Step 1. 1-(2,4-Dichlorobenzyl)-3-(R)-hydroxymethyl-4-(S)-(3-thienyl) pyrrolidine To a solution of 2.4 g (13.1 mmol) of 3-(R)-hydroxymethyl-4-(S)-(3-thienyl)pyrrolidine, 6.8 mL (39 mmol) of diisopropylethylamine, and 4.1 g (23.4 mmol) of 2,4-dichlorobenzaldehyde (Aldrich) in 60 mL of CH$_2$Cl$_2$ at rt was added 5.5 g (26 mmol) of sodium triacetoxyborohydride in several small portions and the reaction mixture was stirred at rt for 3 h. To the reaction was added 50 mL of sat'd NaHCO3 solution and the mixture was extracted with CH$_2$Cl$_2$. The combined organic fractions were washed with sat'd NaCl solution, dried over MgSO$_4$, filtered and the filtrate was concentrated. The residue was purified by chromatography (silica, hexanes:acetone, 4:1) to give the title compound. Mass Spectrum (ESI) m/e=342 (M+1 $^{35}$Cl, $^{35}$Cl), 344 (M+1 $^{35}$Cl, $^{37}$Cl), and 346 (M+1 $^{37}$Cl, $^{37}$Cl). $^1$H-NMR (CDCl$_3$, 500 MHz): 7.38 (m, 2H), 7.30 (m, 1H), 7.23 (m, 1H), 7.03 (m, 2H), 3.65–3.77 (m, 3H), 3.34 (m, 1H), 3.21 (t, J=8.5 Hz, 1H), 2.82 (m, 2H), 2.70 (m, 1H), 2.52 (t, J=8 Hz, 1H), 2.38 (m, 1H). $^{13}$C-NMR (CDCl$_3$, 125 MHz): 145.0, 134.7, 134.6, 133.3, 131.3, 129.3, 127.0, 126.9, 126.0, 119.8, 66.2, 61.7, 57.8, 56.1, 48.0, 41.7.). [α]D=+3.0 (c=1.75, CHCl$_3$).

Step 2. 3-(R)-Formyl-4-(S)-(3-thienyl)pyrrolidine

To a solution of 0.31 mL (3.6 mmol) of oxalyl chloride in 20 mL of CH$_2$Cl$_2$ at −78° C. was added 0.51 mL (7.2 mmol) of DMSO and the reaction mixture was stirred. After 10 min., a solution of 0.49 g (1.8 mmol) of 1-(2,4-dichlorobenzyl)-3-(R)-hydroxymethyl-4-(S)-(3-thienyl) pyrrolidine in 20 mL of CH$_2$Cl$_2$ was then added. After stirring for 10 min. at −78° C., the reaction was allowed to warm to rt. The reaction mixture was poured into ether and extracted twice with sat'd NaHCO$_3$ solution and once with sat'd NaCl solution. The organic fraction was dried over Na$_2$SO$_4$, filtered and the filtrate was concentrated to give 0.49 g of the title compound. Mass Spectrum (ESI) m/e=340 (M+1 $^{35}$Cl, $^{35}$Cl), 342 (M+1 $^{35}$Cl, $^{37}$Cl), and 344 (M+1 $^{37}$Cl, $^{37}$Cl).

EXAMPLE 4

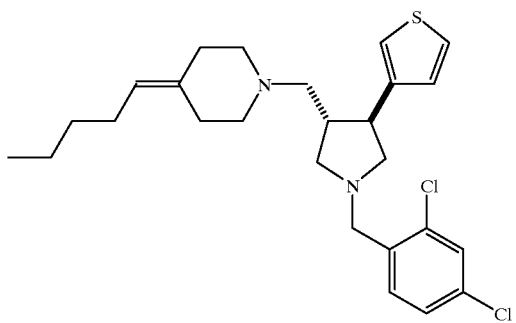

1-(2,4-Dichlorobenzyl)-3-(S)-(4-pentyliden-1-ylpiperidinylmethyl)-4-(S)-(3-thienyl)pyrrolidine
Preparation of 4-pentyliden-1-ylpiperidine
Step 1. 1-t-Butoxycarbonyl-4-pentyliden-1-ylpiperidine To a solution of 6.2 g (15 mmol) of n-pentylphosphonium bromide in 30 mL of DMF was added 0.43 g (15 mmol) of NaH (80% dispersion in mineral oil). The reaction mixture was warmed at 40° C. and stirred for 30 min, whereupon was then added a solution of 2 g (10 mmol) of 1-t-butoxycarbonyl-4-piperidone in 15 mL of DMF and the mixture was heated at 40° C. for 12 h. To the reaction mixture was then added 200 mL of a sat'd aqueous NH4Cl solution and the mixture was extracted with ether. The combined organic fractions were washed with sat'd NaCl solution, dried over $MgSO_4$, filtered and the filtrate was concentrated. The residue was purified by chromatography (silica, hexanes:ethyl acetate, 9:1) to give the title compound. $^1$H NMR ($CDCl_3$) δ 5.22 (t, J=7.2 Hz, 1H).

Step 2. 4-Pentyliden-1-ylpiperidine

To a solution of 0.500 g (1.97 mmol) of 1-t-butoxycarbonyl-4-pentylidenepiperidine in 8 mL of $CH_2Cl_2$ at rt was added 2 mL of trifluoromethanesulfonic acid and the mixture was stirred for 3 h. To the reaction mixture was added 20 mL of sat'd $K_2CO_3$ solution and it was extracted with $CH_2Cl_2$. The combined organic layers were dried over $MgSO_4$, filtered and the filtrate was concentrated to give the title compound which was used without further purification.

Step 3. 1-(2,4-Dichlorobenzyl)-3-(S)-(4-pentylidenepiperidinylmethyl)-4-(S)-(3-thienyl)pyrrolidine To a solution of 0.235 g (0.69 mmol) of 3-(R)-formyl-4-(S)-(3-thienyl)pyrrolidine, 0.3 mL (1.7 mmol) of diisopropylethylamine, and 0.127 g (0.83 mmol) of 4-pentyliden-1-ylpiperidine in 3 mL of $CH_2Cl_2$ at rt was added 0.295 g (1.4 mmol) of sodium triacetoxyborohydride in several small portions and the reaction mixture was stirred at rt for 3 h. To the reaction was added 5 mL of sat'd $NaHCO_3$ solution and the mixture was extracted with $CH_2Cl_2$. The combined organic fractions were washed with sat'd NaCl solution, dried over $MgSO_4$, filtered and the filtrate was concentrated. The residue was purified by chromatography (silica, hexanes:ethyl acetate, 4:1) to give the title compound. $^1$H NMR ($CDCl_3$) δ 5.11 (t, J=7 Hz, 1H). Mass Spectrum (ESI) m/e=477 (M+1 $^{35}$Cl, $^{35}$Cl), 479 (M+1 $^{35}$Cl, $^{37}$Cl), and 481 (M+1 $^{37}$Cl, $^{37}$Cl). $[α]_D$=+15.1 (c=2.4, $CHCl_3$).

The following Examples 5 to 9 were prepared from 3-(R)-formyl-4-(S)-(3-thienyl)pyrrolidine and the corresponding piperidine derivative according to procedures described in Example 4. When not commercially available, the preparation of the piperidine intermediates is described.

EXAMPLE 5

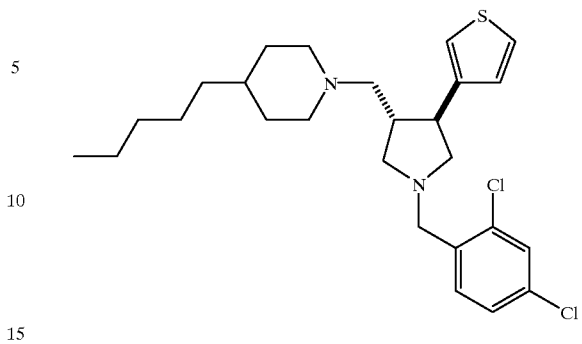

1-(2,4-Dichlorobenzyl)-3-(S)-(4-pentylpiperidinylmethyl)-4-(S)-(3-thienyl)pyrrolidine Mass Spectrum (ESI) m/e=479 (M+1 $^{35}$Cl, $^{35}$Cl), 481 (M+1 $^{35}$Cl, $^{37}$Cl), and 483 (M+1 $^{37}$Cl, $^{37}$Cl). $[α]_D$=+13.8 (c=1.15, $CHCl_3$).

Preparation of 4-Pentylpiperidine

A mixture of 0.507 g (2.0 mmol) of 1-t-butoxycarbonyl-4-pentyliden-1-ylpiperidine (Example 4) and 0.125 g of 10% Pd/C in 25 mL of methanol was hydrogenated at 50 psi for 15 h. The reaction mixture was then filtered through a pad of celite and the filtrate was concentrated. The residue was purified by chromatography (silica, hexanes:ethyl acetate, 9:1) to give 1-t-butoxycarbonyl-4-pentylpiperidine. Removal of the BOC protecting group was achieved as described in Example 4, Step 2 to give the title compound.

EXAMPLE 6

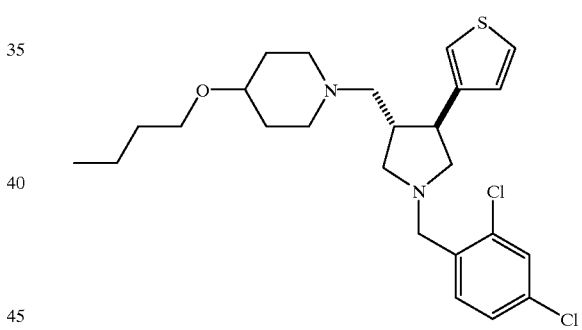

1-(2,4-Dichlorobenzyl)-3-(S)-(4-(butyloxy)piperidinylmethyl)-4-(S)-(3-thienyl) pyrrolidine Mass Spectrum (ESI) m/e=481 (M+1 $^{35}$Cl, $^{35}$Cl), 483 (M+1 $^{35}$Cl, $^{37}$Cl), and 485 (M+1 $^{37}$Cl, $^{37}$Cl). $[α]_D$=+9.76 (c=2.3, $CHCl_3$).

Preparation of 4-(Butyloxy)piperidine
Step 1. 1-t-Butoxycarbonyl-4-hydroxypiperidine To a solution of 10 g (50 mmol) of 1-t-butoxycarbonyl-4-piperidone (Aldrich) in 10 mL of THF at −78° C. was added 75 mL (75 mmol) of a 1 M solution of diisobutylaluminum hydride in toluene. The reaction mixture was allowed to warm to −20° C. and stirred for 3 h. After this time it was poured into 500 mL of sat'd solution of potassium sodium tartrate tetrahydrate (Rochelle salt), the mixture was stirred vigorously for 20 min, and the layers were separated. The aqueous layer was washed with ethyl acetate and the combined organic fractions were washed with brine, dried over $MgSO_4$, filtered, and the filtrate was concentrated to give the title compound which was used without further purification.

Step 2. 4-(Butyloxy)piperidine

To a solution of 1 g (5 mmol) of 1-t-butoxycarbonyl-4-hydroxypiperidine and 2.8 g (15 mmol) of 1-iodobutane in 5 mL of DMP was added 330 mg (11 mmol) of NaH (80% dispersion in mineral oil) and the mixture was heated to 40° C. After 5 h, 20 mL of $H_2O$ was added to the reaction mixture and it was extracted with ethyl acetate. The combined organic fractions were washed with sat'd NaCl solution, dried over $MgSO_4$, filtered and the filtrate was concentrated. The residue was purified by chromatography (silica, hexanes:ethyl acetate=4:1) to give 1-t-butoxycarbonyl-4-(butoxy)piperidine. Removal of the BOC protecting group was achieved as described in Example 4, Step 2 to give the title compound.

EXAMPLE 8

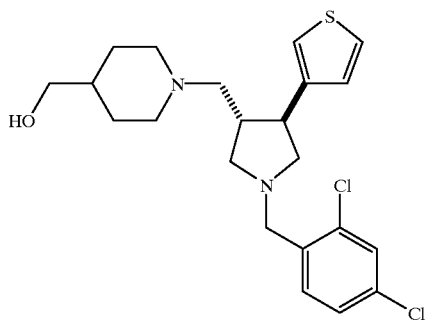

1-(2,4-Dichlorobenzyl)-3-(S)-(4-(hydroxymethyl)piperidinylmethyl)-4-(S)-(3-thienyl)pyrrolidine Mass Spectrum (ESI) m/e=439 (M+1 $^{35}Cl$, $^{35}Cl$), 441 (M+1 $^{35}Cl$, $^{37}Cl$), and 443 (M+1 $^{37}Cl$, $^{37}Cl$). $[\alpha]_D$=+0.14 (c=2.1, $CHCl_3$).

Preparation of 4-Hydroxymethylpiperidine

To a suspension of 28.2 g (696.6 mmol) of $LiAlH_4$ in 800 mL of THF at rt was carefully added 30 g (232.2 mmol) of 4-carboxypiperidine (isonipecotic acid, Aldrich) and the reaction mixture was stirred at rt for 24 h. To the reaction mixture was slowly added 30 mL of $H_2O$ over a period of 2 h, followed by 30 mL of a 15% NaOH solution and 30 mL of $H_2O$. The mixture was diluted with ether, filtered, and the solids were triturated several times with ethyl acetate. The combined organic fractions were concentrated to give the title compound.

EXAMPLE 9

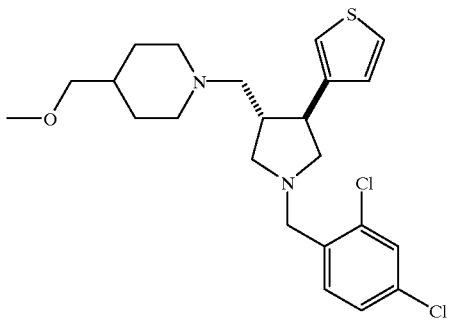

1-(2,4-Dichlorobenzyl)-3-(S)-(4-(methoxymethyl)piperidinylmethyl)-4-(S)-(3-thienyl)pyrrolidine Mass Spectrum (ESI) m/e=453 (M+1 $^{35}Cl$, $^{35}Cl$), 455 (M+1 $3^5Cl$, 37Cl), and 457 (M+1 $^{37}Cl$, $^{37}Cl$). $^1$H NMR (500 MHz, $CDCl_3$) δ 7.46 (d, J=8 Hz, 1H), 7.36 (d, J=2 Hz, 1H), 7.21-7.25 (m, 2H), 7.07 (m, 1H), 7.02 (m, 1H), 3.72 (s, 2H), 3.32 (s, 3H), 3.20 (d, J=6.5 Hz, 2H), 3.11 (m, 1H), 2.97 (t, J=8.3 Hz, 1H) 2.90 (m, 2H), 2.74 (m, 1H), 2.69 (dd, J1=9 Hz, J2=7 Hz, 1H), 2.53 (m, 1H), 2.40 (m, 3H), 1.87 (m, 2H), 1.64 (m, 2H), 1.54 (m, 1H), 1.21 (m, 2H). $[\alpha]_D$=+11.9 (c=2.1, $CHCl_3$).

Preparation of 4-(Methoxymethyl)piperidine

Step 1. 1-t-Butoxycarbonyl-4-hydroxymethylpiperidine

To a stirred mixture of 22.2 g (193 mmol) of 4-hydroxymethylpiperidine (Example 8) in 100 mL of $CH_2Cl_2$ and 75 mL of a 15% aqueous solution of NaOH was added a solution of 63 g (289 mmol) of $Boc_2O$ in 50 ml of $CH_2Cl_2$ over a period of 2 h. After stirring for 30 min, the organic layer of the reaction mixture was washed with 15% aqueous NaOH solution and sat'd NaCl solution, dried over $MgSO_4$, filtered and the filtrate was concentrated. The residue was purified by chromatography (silica, hexanes:ethyl acetate=19:1, then 4:1) to give the title compound.

Step 2. 1-t-Butoxycarbonyl-4-methoxymethylpiperidine

To a solution of 0.1 g (0.46 mmol) of 1-t-butoxycarbonyl-4-hydroxymethylpiperidine and 0.1 mL (1.6 mmol) of iodomethane in 2.5 mL of DMF was added 0.022 g (0.92 mmol) of NaH (80% dispersion in mineral oil). After 2 h, 10 mL of $H_2O$ was added to the reaction mixture and it was extracted with ether. The combined organic fractions were washed with sat'd NaCl solution, dried over $MgSO_4$, filtered and the filtrate was concentrated. The residue was purified by chromatography (silica, hexanes:ethyl acetate=4:1) to give the title compound.

Step 3. 4-Methoxymethylpiperidine

To a solution of 0.093 g (0.4 mmol) of 1-t-butoxycarbonyl-4-methoxyymethylpiperidine in 4 mL of $CH_2Cl_2$ at rt was added 1 mL of trifluoromethanesulfonic acid and the mixture was stirred for 2 h. 20 mL of sat'd $K_2CO_3$ solution was added to the reaction mixture and it was extracted with $CH_2Cl_2$. The combined organic layers were dried over $MgSO_4$, filtered and the filtrate was concentrated to give the title compound which was used without further purification.

The following Examples 10 to 16 were prepared from 3-(R)-formyl-4-(S)-(3-thienyl)pyrrolidine and the corresponding piperidine derivative according to procedures described in Example 4. The piperidine intermediates were prepared according to procedures described in Example 9.

EXAMPLE 10

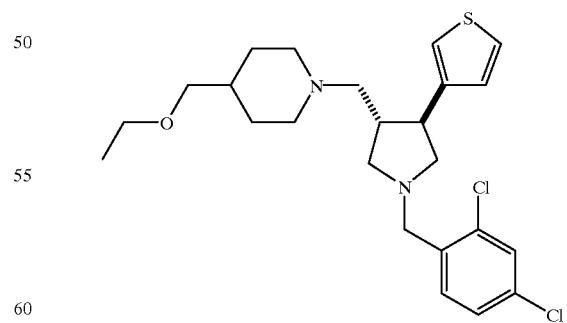

1-(2,4-Dichlorobenzyl)-3-(S)-(4-(ethoxymethyl)piperidinylmethyl)-4-(S)-(3-thienyl)pyrrolidine Mass Spectrum (ESI) m/e=467 (M+1 $^{35}Cl$, $^{35}Cl$), 469 (M+e 35Cl, $^{37}Cl$), and 471 (M+1 $^{37}Cl$, $^{37}Cl$). $[\alpha]_D$=+13.9 (c=1.2, $CHCl_3$).

EXAMPLE 11

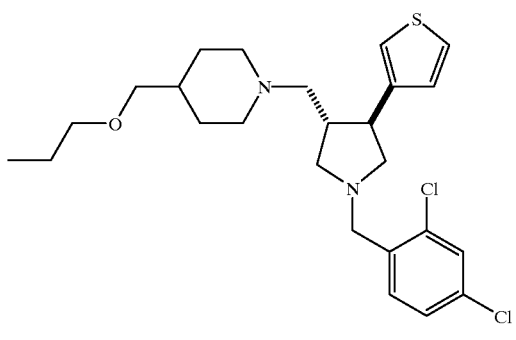

1-(2,4-Dichlorobenzyl)-3-(S)-(4-(propoxymethyl) piperidinylmethyl)-4-(S)-(3-thienyl)pyrrolidine Mass Spectrum (ESI) m/e=481 (M+1 $^{35}$Cl, $^{35}$Cl), 483 (M+1 $^{35}$Cl, $^{37}$Cl), and 485 (M+1 $^{37}$Cl, $^{37}$Cl). [α]$_D$=+9.4 (c=0.9, CHCl$_3$).

EXAMPLE 12

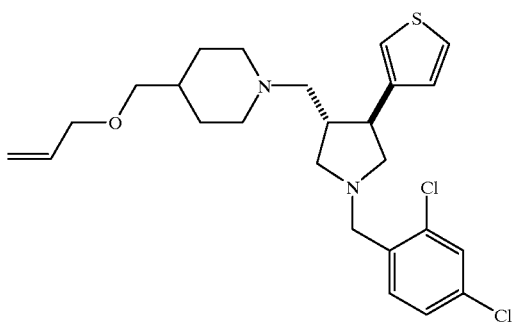

1-(2,4-Dichlorobenzyl)-3-(S)-(4-(allyloxymethyl) piperidinylmethyl)-4-(S)-(3-thienyl)pyrrolidine Mass Spectrum (ESI) m/e=479 (M+1 $^{35}$Cl $^{35}$Cl), 481 (M+1 35Cl, $^{37}$Cl), and 483 (M+1 $^{37}$Cl, $^{37}$Cl). $^1$H NMR (500 MHz, CDCl$_3$) δ 5.91 (m, 1H), 5.28 (dm, J=17 Hz, 1H), 5.17 (dm, J=10.5 Hz, 1H). [α]$_D$=+15.3 (c=1.35, CHCl$_3$).

EXAMPLE 13

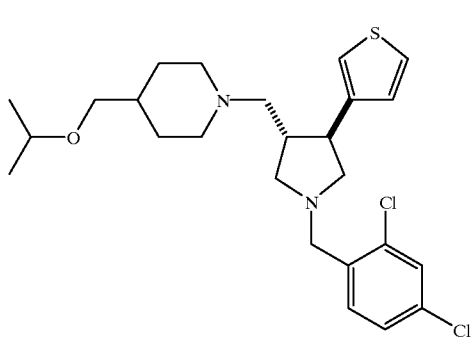

1-(2,4-Dichlorobenzyl)-3-(S)-(4-(isopropoxymethyl) piperidinylmethyl)-4-(S)-(3-thienyl)pyrrolidine Mass Spectrum (ESI) m/e=481 (M+1 $^{35}$Cl, $^{35}$Cl), 483 (M+1 35Cl, $^{37}$Cl), and 485 (M+1 $^{37}$Cl, $^{37}$Cl). [α]$_D$=+11.3 (c=2.5, CHCl$_3$).

EXAMPLE 14

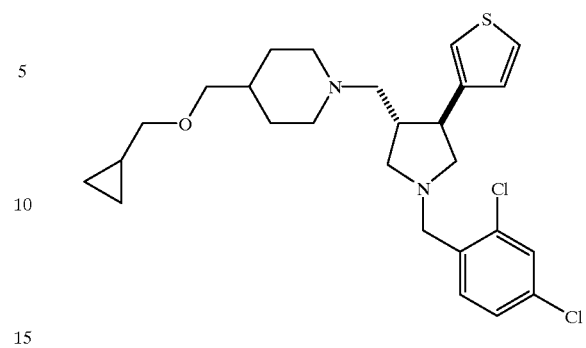

1-(2,4-Dichlorobenzyl)-3-(S)-(4-(cyclopropylmethyloxymethyl)piperidinylmethyl)-4-(S)-(3-thienyl)pyrrolidine Mass Spectrum (ESI m/e=493 (M+1 $^{35}$Cl, $^{35}$Cl), 495 (M+1 $^{35}$Cl, $^{37}$Cl), and 497 (M+1 $^{37}$Cl, $^{37}$Cl). $^1$H NMR (500 MHz, CDCl$_3$) δ 7.46 (d, J=8 Hz, 1H), 7.37 (d, J=2 Hz, 1H), 7.22–7.26 (m, 2H), 7.08 (m, 1H), 7.03 (m, 1H), 3.73 (s, 2H),), 3.25 (m, 2H), 3.11 (m, 1H), 2.97 (t, J=8.3 Hz, 1H) 2.90 (m, 2H), 2.74 (m, 1H), 2.69 (dd, J1=9 Hz, J2=7 Hz, 1H), 2.53 (m, 1H), 2.40 (m, 3H), 1.87 (m, 2H), 1.68 (m, 2H), 1.57 (m, 1H), 1.20 (m, 2H), 1.06 (m, 1H), 0.53 (m, 2H), 0.20 (m, 2H). [α$_D$=+16.5 (c=2.95, CHCl$_3$).

EXAMPLE 15

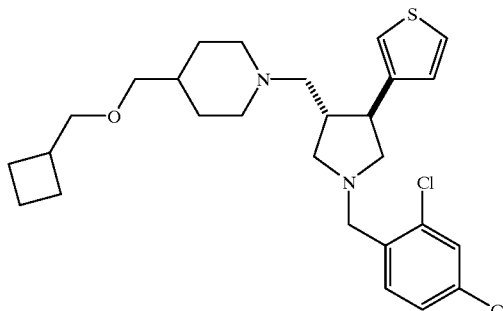

1-(2,4-Dichlorobenzyl)-3-(S)-(4-(cyclobutylmethyloxymethyl)piperidinylmethyl)-4-(S)-(3-thienyl)pyrrolidine Mass Spectrum (ESI) m/e=507 (M+1 $^{35}$Cl, $^{35}$Cl), 509 (M+1 $^{35}$Cl, $^{37}$Cl), and 511 (M+1 $^{37}$Cl, $^{37}$Cl). $^1$H NMR (500 MHz, CDCl$_3$) δ 7.47 (d, J=8 Hz, 1H), 7.37 (d, J=2 Hz, 1H), 7.22–7.26 (m, 2H), 7.08 (m, 1H), 7.03 (m, 1H), 3.74 (s, 2H), 3.4 (d, J=7 Hz, 2H), 3.25 (d, J=6.5 Hz, 2H), 3.13 (m, 1H), 2.98 (t, J=8.3 Hz, 1H) 2.90 (m, 2H), 2.75 (m, 1H), 2.70 (dd, J1=9 Hz, J2=7 Hz, 1H), 2.53-2.60 (m, 2H), 2.42 (m, 3H), 2.07 (m, 2H), 1.89 (m, 4H), 1.63–1.78 (m, 4H), 1.56 (m, 1H), 1.20 (m, 2H). [α]$_D$=+13.0 (c=2.75, CHCl$_3$).

EXAMPLE 16

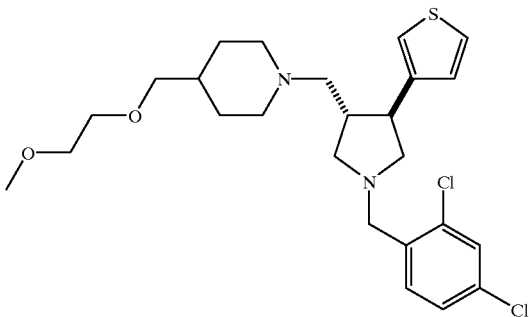

1-(2,4-dichlorobenzyl)-3-(S)-(4-(methoxyethyloxymethyl) piperidinylmethyl)-4-(S)-(3-thienyl)pyrrolidine
Mass Spectrum (ESI) m/e=497 (M+1 $^{35}$Cl, $^{35}$Cl), 499 (M+1 $^{35}$Cl, $^{37}$Cl), and 501 (M+1 $^{37}$Cl, $^{37}$Cl). [α]$_D$=+11.3 (c=0.9, CHCl$_3$).

The following Examples 17 to 26 were prepared from 3-(R)-formyl-4-(S)-(3-thienyl)pyrrolidine and the corresponding piperidine derivative according to procedures described in Example 4. When not commercially available, the preparation of the piperidine intermediates is described.

EXAMPLE 17

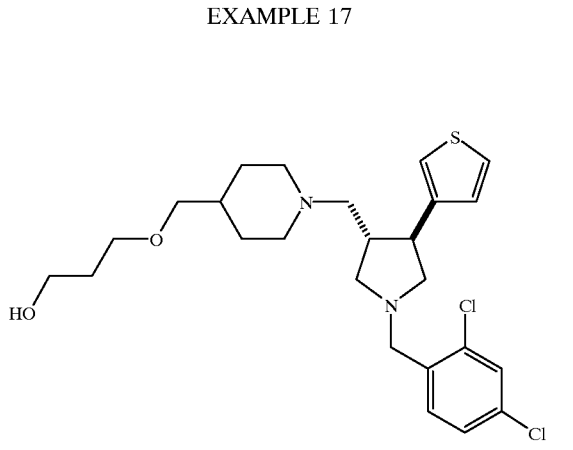

1-(2,4-Dichlorobenzyl)-3-(S)-(4-(3-hydroxypropyloxymethyl)piperidinylmethyl)-4-(S)-(3-thienyl)pyrrolidine Mass Spectrum (ESI) m/e=497 (M+1 $^{35}$Cl, $^{35}$Cl), 499 (m+1 $^{35}$Cl, $^{37}$Cl), and 501 (M+1 $^{37}$Cl, $^{37}$Cl). [α]$_D$=+13.2 (c=1.5, CHCl$_3$).

Preparation of 4-(3-hydroxypropyloxymethyl)piperidine

Step 1. 1-Bromo-3-(triisopropylsilyloxy)propane

A solution of 5.0 g (36 mmol) of 3-bromopropanol, 1.04 g (54 mmol) of chlorotriisopropylsilane, and 7.1 g (104 mmol) of imidazole in 50 mL of CH$_2$Cl$_2$ was stirred for 3 d. To the reaction mixture was added 100 mL of H$_2$O and the mixture was extracted with CH$_2$Cl$_2$. The combined organic layers were dried over MgSO$_4$, filtered and the filtrate was concentrated. The residue was purified by chromatography (silica, hexanes:ethyl acetate=19:1) to give the title compound.

Step 2. 1-t-Butoxycarbonyl-4-(3-triisopropylsilyloxypropyloxymethyl) piperidine

To a solution of 0.5 g (2.3 mmol) of 1-t-butoxycarbonyl-4-hydroxymethylpiperidine and 1.4 g (4.6 mmol) of 1-bromo-3-(triisopropylsilyloxy)propane in 3 mL of DMF was added 0.12 g (4.1 mmol) of NaH (60% dispersion in mineral oil) and the reaction mixture was stirred at rt for 16 h. To the reaction mixture was added 10 mL of H$_2$O and it was extracted with ether. The combined organic fractions were washed with sat'd NaCl solution, dried over MgSO$_4$, filtered and the filtrate was concentrated. The residue was purified by chromatography (silica, hexanes:ethyl acetate= 19:1) to give the title compound.

Step 3. 1-t-Butoxycarbonyl-4-(3-hydroxypropyloxymethyl) piperidine

To a solution of 0.53 g (1.2 mmol) of 1-t-butoxycarbonyl-4-(3-triisopropylsilyloxymethyl) piperidine in 0.5 mL of THF was added 2 mL of a 1M solution of tetrabutylammonium fluoride in THF and the mixture was stirred at rt. After 1 h, 10 mL of sat'd NaHCO$_3$ solution was added to the reaction mixture and it was extracted with CH$_2$Cl$_2$. The combined organic fractions were washed with sat'd NaCl solution, dried over MgSO$_4$, filtered and the filtrate was concentrated to the title compound.

Step 4. 4-(3-Hydroxypropyloxymethyl)piperidine

Removal of the BOC protecting group was achieved as described in Example 4, Step 2 to give the title compound.

EXAMPLE 18

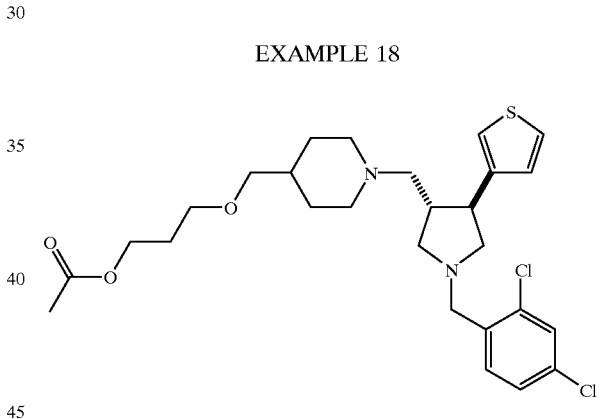

1-(2,4-Dichlorobenzyl)-3-(S)-(4-(3-acetoxypropyloxymethyl) piperidinylmethyl)-4-(S)-(3-thienyl)pyrrolidine A solution of 0.02 g (0.04 mmol) of 1-(2,4-dichlorobenzyl)-3-(S)-(4-(3-hydroxypropyloxymethyl) piperidinylmethyl)-4-(S)-(3-thienyl)pyrrolidine (Example 17), 0.25 mL (0.12 mmol) of acetic anhydride, 0.25 mL (0.3 mmol) of pyridine and a catalytic amount of DMAP in 0.5 mL of CH$_2$Cl$_2$ was stirred at rt for 2 h. TO the reaction mixture was added 10 mL of sat'd Na$_2$CO$_3$ solution and it was extracted with CH$_2$Cl$_2$. The combined organic layers were dried over MgSO$_4$, filtered and the filtrate was concentrated. The residue was purified by chromatography (silica, hexanes:ethyl acetate, 1:1) to give the title compound. Mass Spectrum (ESI) m/e=539 (M+1 $^{35}$Cl, $^{35}$Cl), 541 (M+1 $^{35}$Cl, $^{37}$Cl), and 543 (M+1 $^{37}$Cl, $^{37}$Cl).

EXAMPLE 19

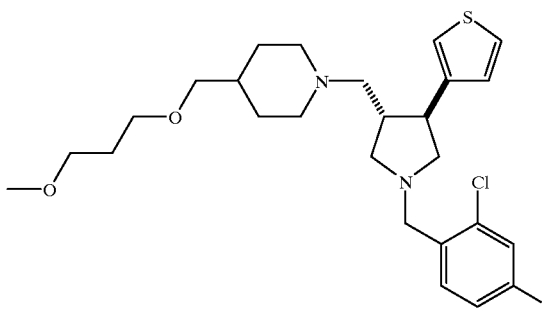

1-(2,4-Dichlorobenzyl)-3-(S)-(4-(3-methoxypropyloxymethyl) piperidinylmethyl)-4-(S)-(3-thienyl)pyrrolidine Mass Spectrum (ESI) m/e=511 (M+1 $^{35}$Cl, $^{35}$Cl), 513 (M+1 $^{35}$Cl, $^{37}$Cl), and 515 (M+1 $^{37}$Cl, $^{37}$Cl). $[\alpha]_D$=+13.5 (c=1.3, CHCl$_3$).

Preparation of 4-(3-methoxypropyloxymethyl)piperidine

The title compound was prepared from 1-t-butoxycarbonyl-4-(3-hydroxypropyloxymethyl)piperidine (Example 17) by procedures described in Example 9.

EXAMPLE 20

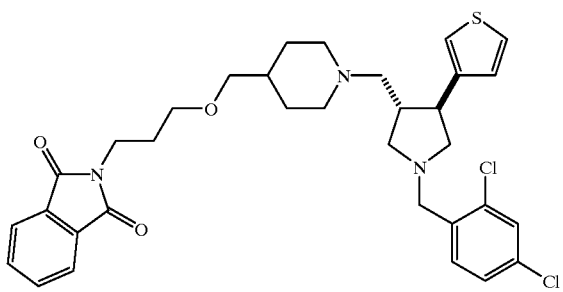

1-(2,4-Dichlorobenzyl)-3-(S)-(4-(3-phthalimidopropyloxymethyl)piperidinylmethyl)-4-(S)-(3-thienyl)pyrrolidine Mass Spectrum (ESI) m/e=626 (M+1 $^{35}$Cl, 35Cl), 628 (M+1 $^{35}$Cl, $^{37}$Cl), and 630 (M+1 $^{37}$Cl, $^{37}$Cl). $^1$H NMR (500 MHz, CDCl$_3$) δ 7.81 (m, 2H), 7.68 (m, 2H), 7.44 (d, J=8.5 Hz, 1H), 7.34 (d, J=2 Hz, 1H), 7.20-7.24 (m, 2H), 7.05 (m, 1H), 7.00 (m, 1H), 4.11 (q, J=7 Hz, 2H), 3.78 (t, J=6.8 Hz, 1H), 3.70 (s, 2H), 3.44 (t, J=6.8 Hz, 1H), 3.16 (d, J=6.5 Hz, 2H), 3.08 (m, 1H), 2.95 (t, J=8.3 Hz, 1H) 2.90 (m, 2H), 2.79 (m, 1H), 2.66 (dd, J1=9 Hz, J2=7 Hz, 1H), 2.50 (m, 1H), 2.32–2.40 (m, 3H), 1.93 (m, 2H), 1.76 (m, 2H), 1.54 (m, 1H), 1.38 (m, 2H), 1.11 (m, 2H).

Preparation of 4-(3-phthalimidopropyloxymethyl)piperidine

To a solution of 0.344 g (1.26 mmol) of 1-t-butoxycarbonyl-4-(3-hydroxypropyloxymethyl)piperidine (Example 17, Step 3), 0.926 g (6.3 mmol) of phthalimide, and 0.661 g (2.52 mmol) of triphenylphosphine in 10 mL of THF at 0° C. was added dropwise 0.4 mL of diethylazodicarboxylate (DEAD). The reaction mixture was allowed to warm to rt and was stirred for 36 h. To the reaction mixture was added 20 mL of ether and it was filtered through a thin pad of celite. The filtrate was washed with sat'd NaHCO$_3$ solution and sat'd NaCl solution, dried over MgSO$_4$, filtered and the filtrate was concentrated. The residue was purified by chromatography (silica, hexanes:ethyl acetate, 2:1) to give 1-t-butoxycarbonyl-4-(3-phthalimidopropyloxymethyl)piperidine. Removal of the BOC protecting group was achieved as described in Example 4, Step 2 to give the title compound.

EXAMPLE 21

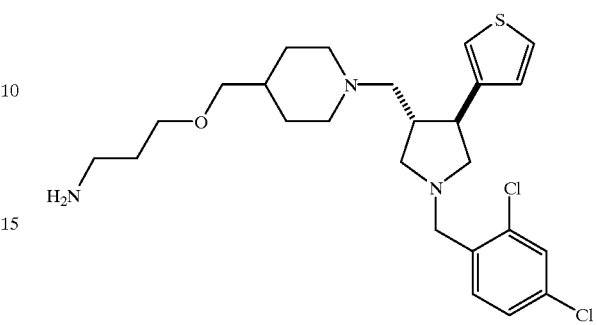

1-(2,4-Dichlorobenzyl)-3-(S)-(4-(3-aminopropyloxymethyl)piperidinylmethyl)-4-(S)-(3-thienyl)pyrrolidine A solution of 0.2 g (0.32 mmol) of 1-(2,4-dichlorobenzyl)-3-(S)-(4-(3-phthalimidopropyloxymethyl) piperidinylmethyl)-4-(S)-(3-thienyl)pyrrolidine (Example 20) and 0.2 mL (6.4 mmol) of hydrazine in 2 mL of ethanol was heated at 60° C. for 5 h. To the reaction mixture was added 20 mL of 10% H$_2$SO$_4$ and the mixture was extracted three times with ethyl acetate. The aqueous layer was brought to pH=12 by addition of 15% NaOH and extracted with ethyl acetate. The combined organic layers were dried over MgSO$_4$, filtered and the filtrate was concentrated to give the title compound. Mass Spectrum (ESI) m/e=496 (M+1 $^{35}$Cl, $^{35}$Cl), 498 (M+1 $^{35}$Cl, $^{37}$Cl), and 500 (M+1 $^{37}$Cl, $^{37}$Cl). $[\alpha]_D$=+14.9 (c=0.875, CHCl$_3$).

EXAMPLE 22

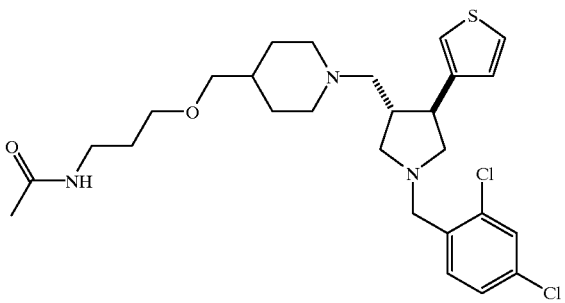

1-(2,4-Dichlorobenzyl)-3-(S)-(4-(3-(acetylamino)propyloxymethyl) piperidinylmethyl)-4-(S)-(3-thienyl) pyrrolidine A solution of 0.03 g (0.06 mmol) of 1-(2,4-dichlorobenzyl)-3-(S)-(4-(3-aminopropyloxymethyl) piperidinylmethyl)-4-(S)-(3-thienyl)pyrrolidine, 0.02 mL (0.12 mmol) of acetic anhydride, 0.025 mL (0.3 mmol) of pyridine and a catalytic amount of DMAP in 0.5 mL of CH$_2$Cl$_2$ was stirred at rt for 18 h. The reaction mixture was concentrated and the residue was purified by chromatography (silica, CH$_2$Cl$_2$:methanol, 9:1) to give the title compound. Mass Spectrum (ESI) m/e=538 (M+1 $^{35}$Cl, $^{35}$Cl), 540 (M+1 $^{35}$Cl, $^{37}$Cl), and 542 (M+1 $^{37}$Cl, $^{37}$Cl).

EXAMPLE 23

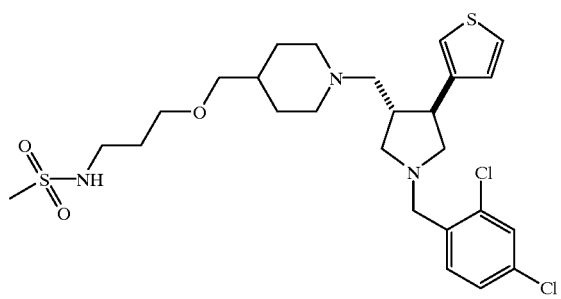

1-(2,4-Dichlorobenzyl)-3-(S)-(4-(3-(methylsulfonylamino)propyloxymethyl) piperidinylmethyl)-4-(S)-(3-thienyl) pyrrolidine A solution of 0.030 g (0.06 mmol) of 1-(2,4-dichlorobenzyl)-3-(S)-(4-(3-aminopropyloxymethyl) piperidinylmethyl)-4-(S)-(3-thienyl)pyrrolidine, 0.02 mL (0.24 mmol) of methanesulfonyl chloride, and 0.03 mL (0.15 mmol) of diisopropylethyl amine in 0.5 mL of $CH_2Cl_2$ was stirred at rt for 18 h. The reaction mixture was concentrated and the residue was purified by chromatography (silica, $CH_2Cl_{2:methanol}$, 95:5) to givethe title compound. Mass Spectrum (ESI) m/e=574 (M+1 $^{35}Cl$, $^{35}Cl$), 576 (M+1 $^{35}Cl$, $^{37}Cl$), and 578 (M+1 $^{37}Cl$, $^{37}Cl$). $[a]_D$=+11.0 (c=0.815, $CHCl_3$).

EXAMPLE 24

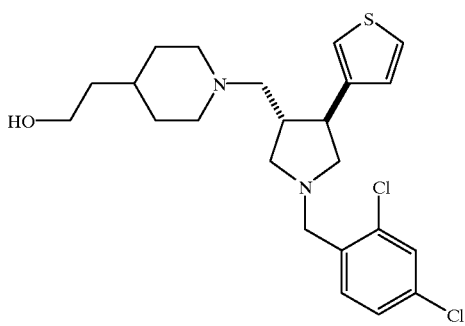

1-(2,4-Dichlorobenzyl)-3-(S)-(4-(hydroxyethyl) piperidinylmethyl)-4-(S)-(3-thienyl)pyrrolidine Mass Spectrum (ESI) m/e=453 (M+1 $^{35}Cl$, $^{35}Cl$), 455 (M+1 $^{35}Cl$, $^{37}Cl$), and 457 (M+1 $^{37}Cl$, $^{37}Cl$). $[\alpha]_D$=+13.4 (c=2.11, $CHCl_3$).

The preparation of 1-t-butoxycarbonyl-4-(hydroxyethyl) piperidine is described in Example 25.

EXAMPLE 25

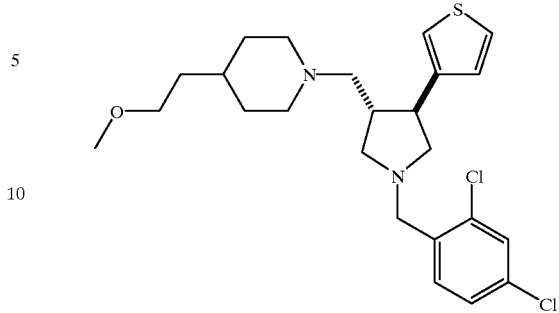

1-(2,4-Dichlorobenzyl)-3-(S)-(4-(methoxyethyl) piperidinylmethyl)-4-(S)-(3-thienyl)pyrrolidine
Mass Spectrum (ESI) m/e=467 (M+1 $^{35}Cl$, $^{35}Cl$), 469 (M+1 $^{35}Cl$, $^{37}Cl$), and 471 (M+1 $^{37}Cl$, $^{37}Cl$). $^1H$ NMR ($CDCl_3$) δ 7.46 (d, J=8 Hz, 1H), 7.37 (d, J=2 Hz, 1H), 7.22–7.27 (m, 2H), 7.08 (m, 1H), 7.03 (m, 1H), 3.73 (s, 2H), 3.41 (t, J=6.5 Hz,, 2H), 3.33 (s, 3H), 3.10 (m, 1H), 2.98 (t, J=8.3 Hz, 1H), 2.93 (m, 1H), 2.85 (m, 1H), 2.73 (m, 1H), 2.69 (dd, J1=9 Hz, J2=7 Hz, 1H), 2.53 (m, 1H), 2.40 (m, 3H), 1.86 (m, 2H), 1.62 (m, 2H), 1.50 (q, J=6.7 Hz, 2H), 1.35 (m, 1H), 1.20 (m, 2H). $[\alpha]_D$=+12.1 (c=1.24, $CHCl_3$).
Preparation of 4-(Methoxyethyl)piperidine
Step 1. 1-t-Butoxycarbonyl-4-(methoxycarbonylmethylene) piperidene 8.4 g (74.9 mmol) of potassium t-butoxide were suspended in 200 mL of THF. To this mixture at rt was slowly added a solution of 13.7 g (75.4 mmol) of trimethylphosphonoacetate in 20 mL of THF. After stirring for 30 min, a solution of 10 g (50.2 mmol) of 1-t-butoxycarbonyl-4-piperidone in 50 mL of THF was added and the mixture was heated to 60° C. for 3.5 h. To the reaction mixture was added 250 mL of a sat'd aqueous $NH_4Cl$ solution and the mixture was extracted with ethyl acetate. The combined organic fractions were washed with sat'd NaCl solution, dried over $MgSO_4$, filtered and the filtrate was concentrated. Chromatography on silica eluting with hexane:ethyl acetate=4:1 gave the title compound.
Step 2. 1-t-Butoxycarbonyl-4-(methoxycarbonylmethyl) piperidine A mixture of 10 g (39 mmol) of 1-t-butoxycarbonyl-4-(methoxycarbonylmethylene)piperidene and 0.5 g of palladium, 10 wt. % on activated carbon in 80 mL of methanol was hydrogenated at 50 psi for 24 h. The reaction mixture was filtered through a pad of silica gel eluting with hexanes :ethyl acetate=4:1 and concentrated to give the title compound. $^1H$ NMR ($CDCl_3$) δ 4.02 (m, 2H), 3.62 (s, 3H), 2.67 (m, 2H), 2.20 (d, J=7.5 Hz, 2H), 1.88 (m, 1H), 1.64 (m, 2H), 1.40 (s, 9H), 1.11 (m, 2H).
Step 3. 1-t-Butoxycarbonyl-4-(hydroxyethyl)piperidine To a solution of 5 g (696.6 mmol) of $LiAlH_4$ in 800 mL of THF at rt was carefully added 30 g (232.2 mmol) of 1-t-butoxycarbonyl-4-(methoxycarbonyl methyl)piperidine and the reaction mixture was stirred at rt for 24 h. To the reaction mixture was slowly added 30 mL of $H_2O$ over a period of 2 h, followed by 30 mL of a 15% NaOH solution and 30 mL of $H_2O$. The mixture was diluted with ether, filtered, and the solids were triturated several times with ethyl acetate. The combined organic fractions were concentrated to give the title compound.
Step 4. 1-t-Butoxycarbonyl-4-(methoxyethyl)piperidine To a solution of 825 mg (3.6 mmol) of 1-t-butoxycarbonyl-4-hydroxyethylpiperidine in 2.5 mL of DMF was added 0.21 g (7.2 mmol) of NaH (80% dispersion in mineral oil) in 3 portions over a period of 30 min. After 16 h 10 mL of H$_2$O was added to the reaction mixture and it was extracted with ethyl acetate. The combined organic fractions were washed with sat'd NaCl solution, dried over MgSO$_4$, filtered and the filtrate was concentrated. The residue was purified by chromatography (silica, hexanes:ethyl acetate=4:1) to give the title compound.
Step 5. 4-(Methoxyethyl)piperidine Removal of the BOC protecting group was achieved as described in Example 4, Step 2 to give the title compound.

EXAMPLE 26

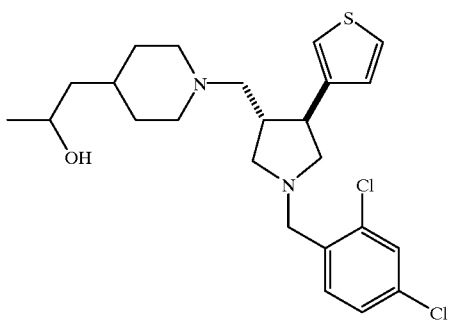

1-(2,4-Dichlorobenzyl)-3-(S)-(4-(2-(RS)-hydroxypropyl)piperidinylmethyl)-4-(S)-(3-thienyl)pyrrolidine
Preparation of 4-(2-(RS)-Hydroxypropyl)piperidine
Step 1. 1-t-Butyloxycarbonyl-4-(2-oxoethyl)piperidine To a solution of 4.8 mL (55 mmol) of oxalyl chloride in 60 mL of CH$_2$Cl$_2$ at −78° C. was added dropwise a solution of 5.8 mL (81.7 mmol) of DMSO in 20 mL of CH$_2$Cl$_2$ and the reaction mixture was stirred. After 10 min, a solution of 6.7 g (29.15 mmol) of 1-t-butyloxycarbonyl-4-(hydroxyethyl)piperidine in 20 mL of CH$_2$Cl$_2$ was added. After stirring for 10 min. at −78° C., 15 mL (107 mmol) of triethylamine were added and the reaction was allowed to warm to rt. After 1 h the reaction mixture was poured into H$_2$O and extracted with ether. The combined organic fractions were washed with sat'd NaCl solution, dried over MgSO$_4$, filtered and the filtrate was concentrated to give the title compound which was used without further purification.
Step 2. 1-t-Butoxycarbonyl-4-(2-(RS)-hydroxypropyl)piperidine To a solution of 2.6 g (11.4 mmol) of 1-t-butyloxycarbonyl-4-(2-oxoethyl)piperidine in 50 mL of ether at −78° C. was added 5.7 mL (17.1 mmol) of 3 M solution of methylmagnesium iodide in ether. The mixture was allowed to warm to −20° C. and stirred for 2.5 h. The reaction mixture was poured into sat'd aqueous NH$_4$Cl solution and extracted with ethyl acetate. The combined organic fractions were washed with sat'd NaCl solution, dried over MgSO$_4$, filtered and the filtrate was concentrated. The residue was purified by chromatography (silica, hexanes:ethyl acetate, 4:1) to give the title compound.
Step 3. 4-(2-(RS)-hydroxypropyl)piperidine Removal of the BOC protecting group was achieved as described in Example 4, Step 2 to give the title compound.
The following Examples 27 to 33 were prepared from 3-(R)-formyl-4-(S)-(3-thienyl)pyrrolidine and the corresponding piperidine derivative according to procedures described in Example 4. The piperidine intermediates were prepared according to procedures described in Example 26

EXAMPLE 27

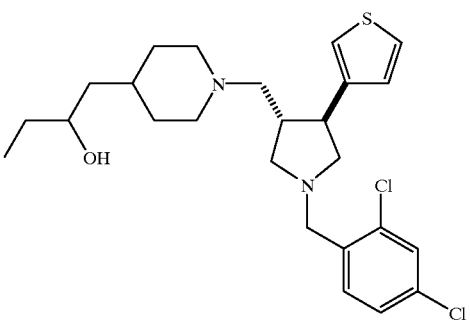

1-(2,4-Dichlorobenzyl)-3-(S)-(4-(2-(RS)-hydroxybutyl)piperidinylmethyl)-4-(S)-(3-thienyl)pyrrolidine Mass Spectrum (ESI) m/e=481 (M+1 $^{35}$Cl, 35Cl), 483 (M+1 $^{35}$Cl, $^{37}$Cl), and 485 (M+1 $^{37}$Cl, $^{37}$Cl).

EXAMPLE 28

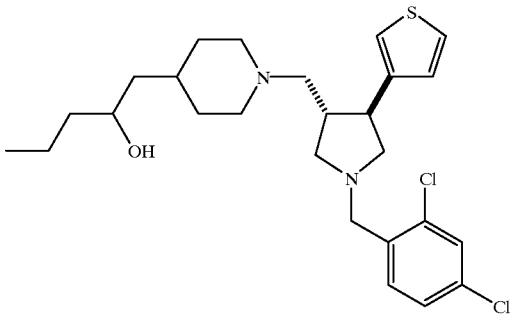

1-(2,4-Dichlorobenzyl)-3-(S)-(4-(2-(RS)-hydroxypentyl)piperidinylmethyl)-4-(S)-(3-thienyl)pyrrolidine Mass Spectrum (ESI) m/e 495 (M+1 $^{35}$Cl, $^{35}$Cl), 497 (M+1 $^{35}$Cl, $^{37}$Cl), and 499 (M+1 $^{37}$Cl, $^{37}$Cl).

EXAMPLE 29

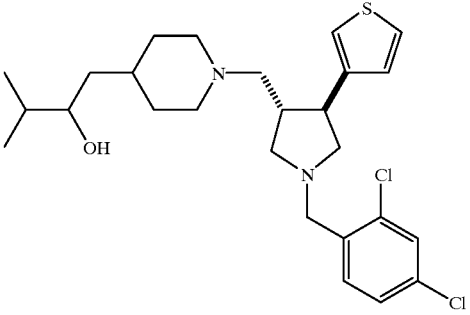

1-(2,4-Dichlorobenzyl)-3-(S)-(4-(2-(RS)-hydroxy-3-methylbutyl)piperidinylmethyl)-4-(S)-(3-thienyl)pyrrolidine Mass Spectrum (ESI) m/e=495 (M+1 $^{35}$Cl, $^{35}$Cl), 497 (M+1 $^{35}$Cl, $^{37}$C]), and 499 (M+1 $^{37}$Cl, $^{37}$Cl).

EXAMPLE 30

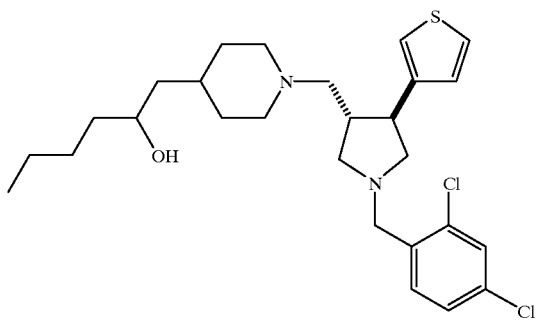

1-(2,4-Dichlorobenzyl)-3-(S)-(4-(2-(RS)-hydroxyhexyl)piperidinylmethyl)-4-(S)-(3-thienyl)pyrrolidine
Mass Spectrum (ESI) m/e=509 (M+1 $^{35}$Cl, $^{35}$Cl), 511 (M+1 $^{35}$Cl, $^{37}$Cl), and 513 (M+1 $^{37}$Cl, $^{37}$Cl).

EXAMPLE 31

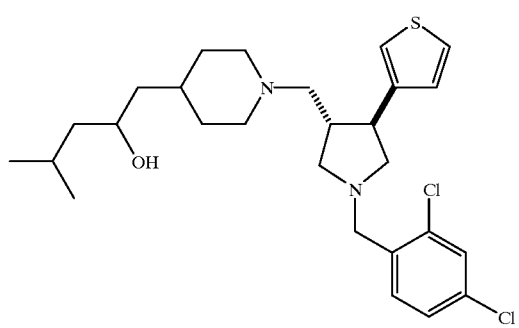

1-(2,4-Dichlorobenzyl)-3-(S)-(4-(2-(RS)-hydroxy-4-pentyl)piperidinylmethyl)-4-(S)-(3-thienyl)pyrrolidine
Mass Spectrum (ESI) m/e=509 (M+1 $^{35}$Cl, $^{35}$Cl), 511 (M+1 $^{35}$Cl, $^{37}$Cl), and 513 (M+1 $^{37}$Cl, $^{37}$Cl).

EXAMPLE 32

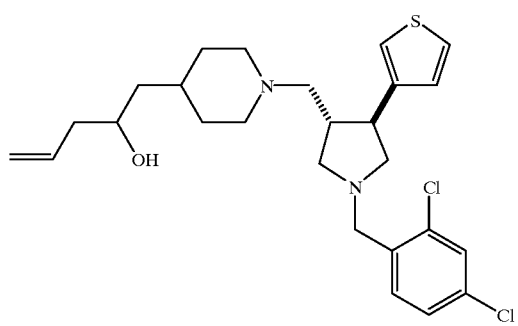

1-(2,4-Dichlorobenzyl)-3-(S)-(4-(2-(RS)-hydroxypent-4-enyl)piperidinylmethyl)-4-(S)-(3-thienyl)pyrrolidine Mass Spectrum (ESI) m/e=493 (M+1 $^{35}$Cl, $^{35}$Cl), 495 (M+1 $^{35}$Cl, $^{37}$Cl), and 497 (M+1 $^{37}$Cl, $^{37}$Cl).

EXAMPLE 33

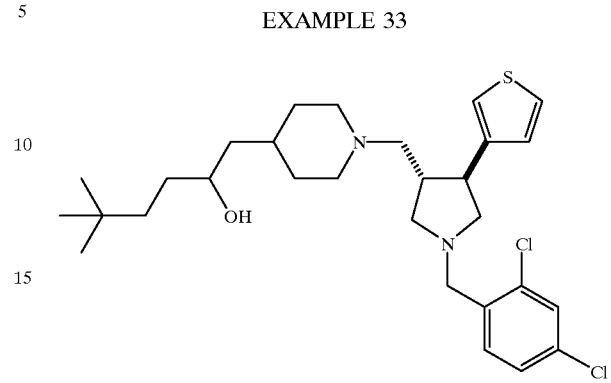

1-(2,4-Dichlorobenzyl)-3-(S)-(4-(2-(RS)-hydroxy-3,3-dimethylbutyl) piperidinylmethyl)-4-(S)-(3-thienyl) pyrrolidine Mass Spectrum (ESI) m/e=509 (m+1 $^{35}$Cl, $^{35}$Cl), 511 (M+1 $^{35}$Cl, $^{37}$Cl), and 513 (M+1 $^{37}$Cl, 37Cl).

EXAMPLE 34

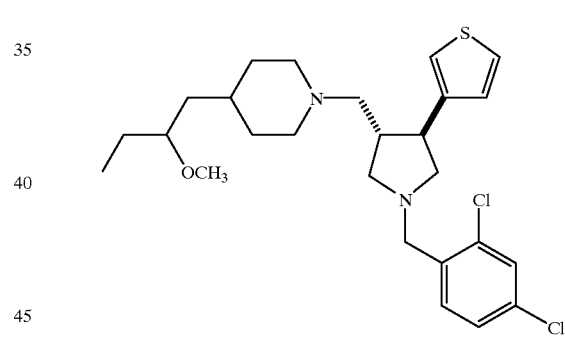

1-(2,4-Dichlorobenzyl)-3-(S)-(4-(2-(RS)-methoxybutyl)piperidinylmethyl)-4-(S)-(3-thienyl)pyrrolidine Mass Spectrum (ESI) m/e=495 (M+1 $^{35}$Cl, $^{35}$Cl), 497 (M+1 $^{35}$Cl, $^{37}$Cl), and 499 (M+1 $^{37}$Cl, $^{37}$Cl).

1-t-Butoxycarbonyl-4-(2-(RS)-methoxyoxybutyl)piperidine was prepared from 1-t-butoxycarbonyl-4-(2-(RS)-hydroxybutyl)piperidine (Example 27) according to procedures described in Example 25, Step 4).

The following Examples 35 to 39 were prepared from 3-(R)-formyl-4-(S)-(3-thienyl)pyrrolidine and the corresponding piperidine derivative according to procedures described in Example 4. The piperidine intermediates were prepared according to procedures described in Example 34.

EXAMPLE 35

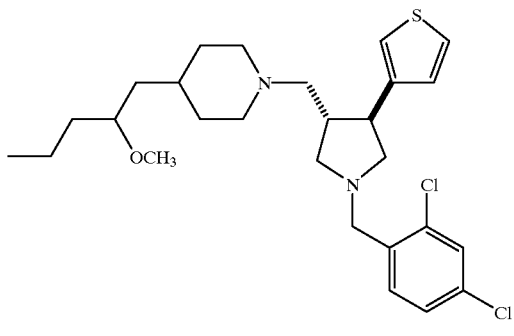

1-(2,4-Dichlorobenzyl)-3-(S)-(4-(2-(RS)-methoxypentyl)piperidinylmethyl)-4-(S)-(3-thienyl)pyrrolidine Mass Spectrum (ESI) m/e=509 (M+1 $^{35}$Cl, $^{35}$Cl), 511 (M+1 $^{35}$Cl, $^{37}$Cl), and 513 (M+1 $^{37}$Cl, $^{37}$Cl).

EXAMPLE 36

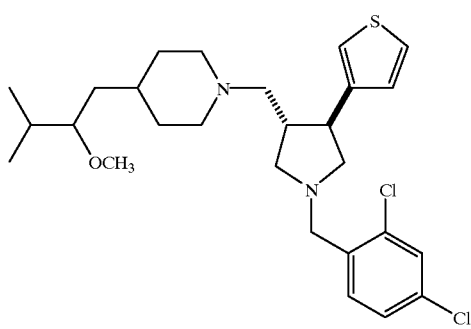

1-(2,4-Dichlorobenzyl)-3-(S)-(4-(2-(RS)-methoxy-3-methylbutyl)piperidinylmethyl)-4-(S)-(3-thienyl)pyrrolidine Mass Spectrum (ESI) m/e=509 (M+1 $^{35}$Cl, $^{35}$Cl), 511 (M+1 $^{35}$Cl, $^{37}$Cl), and 513 (M+1 $^{37}$Cl, $^{37}$Cl).

EXAMPLE 37

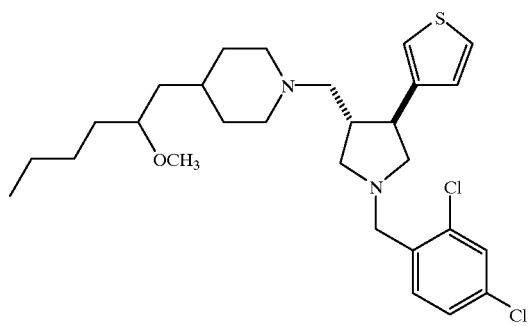

1-(2,4-Dichlorobenzyl)-3-(S)-(4-(2-(RS)-methoxyhexyl)piperidinylmethyl)-4-(S)-(3-thienyl)pyrrolidine Mass Spectrum (ESI) m/e=523 (M+1 $^{35}$Cl, $^{35}$Cl), 525 (M+1 $^{35}$Cl, $^{37}$Cl), and 527 (M+1 $^{37}$Cl, $^{37}$Cl).

EXAMPLE 38

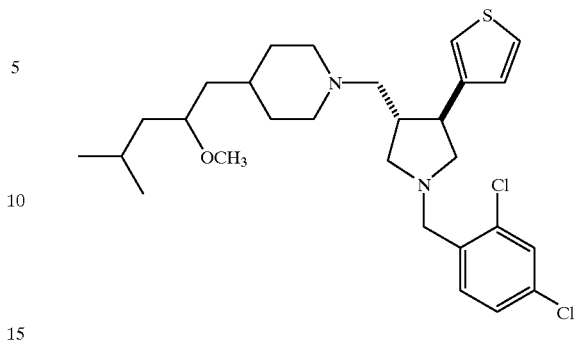

1-(2,4-Dichlorobenzyl)-3-(S)-(4-(2-(RS)-methoxy-4-methoxypentyl)piperidinylmethyl)-4-(S)-(3-thieny)pyrrolidine Mass Spectrum (ESI) m/e 523 (M+1 $^{35}$Cl, $^{35}$Cl), 525 (M+1 $^{35}$Cl, $^{37}$Cl), and 527 (M+1 $^{37}$Cl, $^{37}$Cl).

EXAMPLE 39

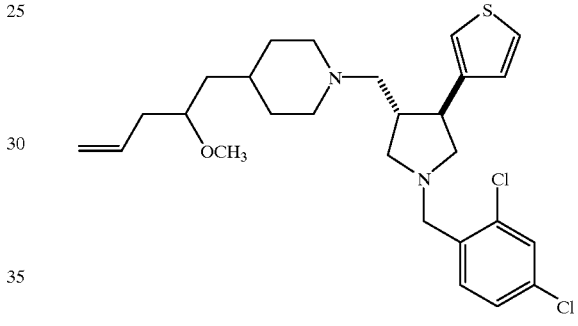

1-(2,4-Dichlorobenzyl)-3-(S)-(4-(2-(RS)-methoxypent-4-enyl)piperidinylmethyl)-4-(S)-(3-thienyl)pyrrolidine Mass Spectrum (ESI) m/e=507 (M+1 $^{35}$Cl, $^{35}$Cl), 509 (M+1 $^{35}$Cl, $^{37}$Cl), and 511 (M+1 $^{37}$Cl, $^{37}$Cl).

EXAMPLE 40

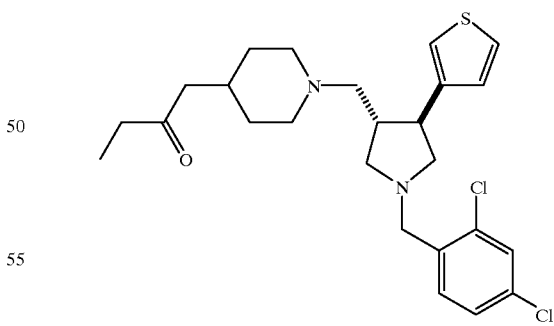

1-(2,4-Dichlorobenzyl)-3-(S)-(4-(2-ketobutyl)piperidinylmethyl)-4-(S)-(3-thienyl)pyrrolidine Mass Spectrum (ESI) m/e=479 (M+1 $^{35}$Cl, $^{35}$Cl), 481 (M+1 $^{35}$Cl, $^{37}$Cl), and 483 (M+1 $^{37}$Cl, $^{37}$Cl).

1-t-Butoxycarbonyl-4-(2-oxobutyl)piperidine was prepared from 1-t-butoxycarbonyl-4-(2-(RS)-hydroxybutyl)piperidine (Example 27) according to procedures described in Example 26, Step 1).

EXAMPLE 41

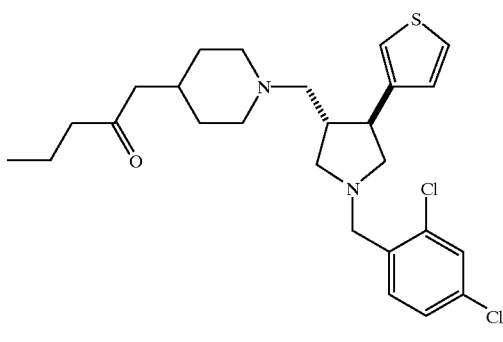

1-(2,4-Dichlorobenzyl)-3-(S)-(4-(2-ketopentyl)piperidinylmethyl)-4-(S)-(3-thienyl)pyrrolidine $^{13}$C NMR (75 MHz, CDCl3) δ 210.6, 145.9, 135.5, 134.3, 132.8, 131.1, 129.0, 127.2, 126.9, 125.4, 119.5, 63.7, 61.3, 59.6, 56.2, 54.1, 53.7, 49.4, 45.4, 44.2, 44.0, 32.2, 32.1, 31.8, 17.2, 13.7. Mass Spectrum (ESI) m/e=493 (M+1 $^{35}$Cl, $^{35}$Cl), 495 (M+1 $^{35}$Cl, $^{37}$Cl), and 497 (M+1 $^{37}$Cl, $^{37}$Cl).

1-t-Butoxycarbonyl-4-(2-oxopentyl)piperidine was prepared from 1-t-butoxycarbonyl-4-(2-(RS)-hydroxypentyl)piperidine (Example 28) according to procedures described in Example 26, Step 1 and Step 2).

EXAMPLE 42

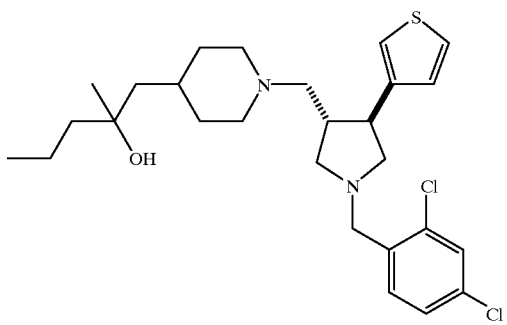

1-(2,4-Dichlorobenzyl)-3-(S)-(4-(2-(RS)-hydroxy-2-methylpentyl)piperidinylmethyl)-4-(S)-(3-thienyl)pyrrolidine Mass Spectrum (ESI) m/e=509 (M+1 $^{35}$Cl, $^{35}$Cl), 511 (M+1 $^{35}$Cl, $^{37}$Cl), and 513 (M+1 $^{37}$Cl, $^{37}$Cl).

1-t-Butoxycarbonyl-4-(2-(RS)-hydroxy-2-methylpentyl)piperidine was prepared from 1-t-butoxycarbonyl-4-(2-oxopentyl)piperidine (Example 41) according to procedures described in Example 26, Step 2).

EXAMPLE 43

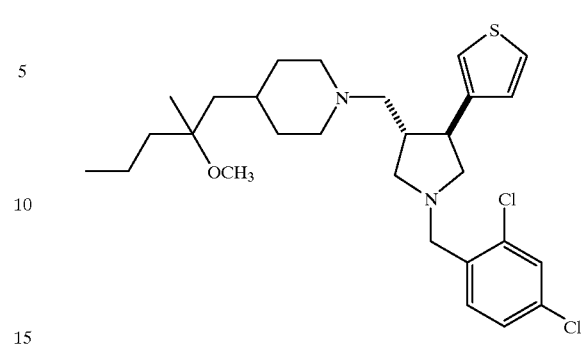

1-(2,4-Dichlorobenzyl)-3-( 2-(RS)-methoxy-2-methylpentyl)piperidinylmethyl)-4-(S)-(3-thienyl)pyrrolidine Mass Spectrum (ESI) m/e=523 (M+1 $^{35}$Cl, $^{35}$Cl), 525 (M+1 $^{35}$Cl, $^{37}$Cl), and 527 (M+1 $^{37}$Cl, $^{37}$Cl).

1-t-Butoxycarbonyl-4-(2-(RS)-methoxy-2-methylpentyl)piperidine was prepared from 1-t-butoxycarbonyl-4-(2-(RS)-hydroxy-2-methylpentyl)piperidine (Example 41) according to procedures described in Example 25, Step 4).

EXAMPLE 44

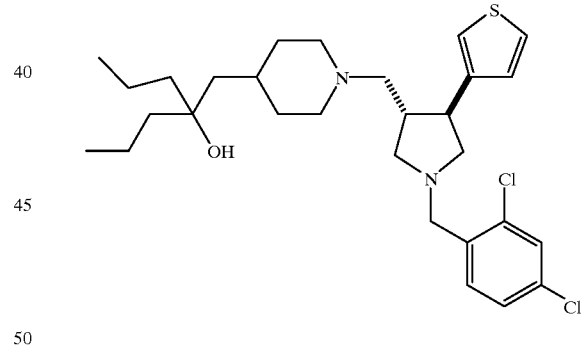

1-(2,4-Dichlorobenzyl)-3-(S)-(4-(2-hydroxy-2-propylpentyl)piperidinylmethyl)-4-(S)-(3-thienyl)pyrrolidine Mass Spectrum (ESI) m/e=537 (M+1 $^{35}$Cl, $^{35}$Cl), 539 (M+1 $^{35}$Cl, $^{37}$Cl), and 541 (M+1 $^{37}$Cl, $^{37}$Cl).

1-t-Butoxycarbonyl-4-(2-(RS)-hydroxy-2-propylpentyl)piperidine was prepared from 1-t-butoxycarbonyl-4-(2-oxopentyl)piperidine (Example 41) according to procedures described in Example 26, Step 2).

EXAMPLE 45

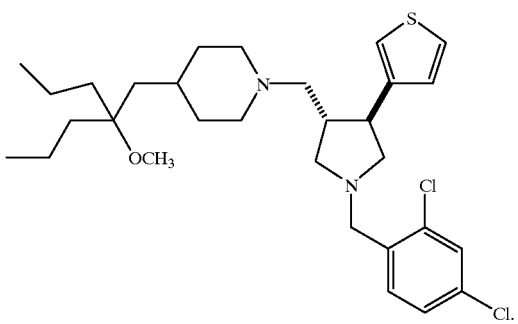

1-(2,4-Dichlorobenzyl)-3-(S)-(4-(2-methoxy-2-propylpentyl)piperidinylmethyl)-4-(S)-(3-thienyl)pyrrolidine Mass Spectrum (ESI) m/e=551 (M+1 $^{35}$Cl, $^{35}$Cl), 553 (M+1 $^{35}$Cl, $^{37}$Cl), and 555 (M+1 $^{37}$Cl, $^{37}$Cl).

1-t-Butoxycarbonyl-4-(2-(RS)-methoxy-2-propylpentyl)piperidine was prepared from 1-t-butoxycarbonyl-4-(2-(RS)-hydroxy-2-propylpentyl)piperidine (Example 44) according to procedures described in Example 25, Step 4).

EXAMPLE 46

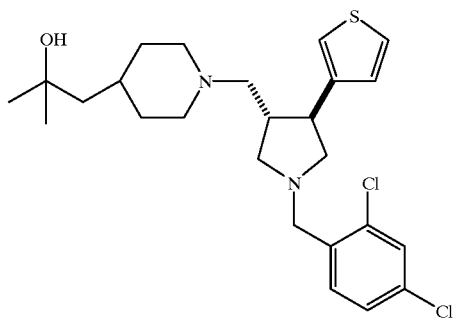

1-(2,4-Dichlorobenzyl)-3-(S)-(4-(2-hydroxy-2-methyl-1-propyl)piperidinylmethyl)-4-(S)-(3-thienyl)pyrrolidine Mass Spectrum (ESI) m/e=481 (M+1 $^{35}$Cl, $^{35}$Cl), 483 (M+1 $^{35}$Cl, $^{37}$Cl), and 485 (M+1 $^{37}$Cl, $^{37}$Cl).

Preparation of 4-(2-Hydroxy-2-methyl-1-propyl)piperidine

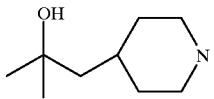

Step 1. 1-t-Butoxycarbonyl-4-(2-hydroxy-2-methyl-1-propyl)piperidine

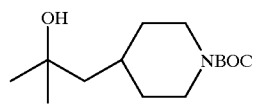

To a solution of 0.69 g (2.7 mmol) of 1-t-butoxycarbonyl-4-(methoxycarbonylethyl)piperidine (Example 22, Step 2) in 26 mL of ether at 0° C. was added dropwise 2.8 mL (8.4 mmol) of CH3MgBr (3 M in ether) and the reaction mixture was warmed slowly to rt. After stirring at rt for 6 h, the reaction was quenched by addition of 20 mL of sat'd NH4Cl solution and the mixture was stirred overnight. The mixture was extracted with ethyl acetate. The combined organic fractions were washed with sat'd NaCl solution, dried over MgSO$_4$, filtered and the filtrate was concentrated. The residue was purified by chromatography (silica, hexanes-:ethyl acetate, 3:1) to give 0.5 g of the title compound.

Step 2. 4-(2-Hydroxy-2-methyl-1-propyl)piperidine

The title compound was prepared from 1-t-butoxycarbonyl-4-(2-hydroxy-2-methyl-1-propyl)piperidine according to procedures described in Example 5, Step 3.

EXAMPLE 47

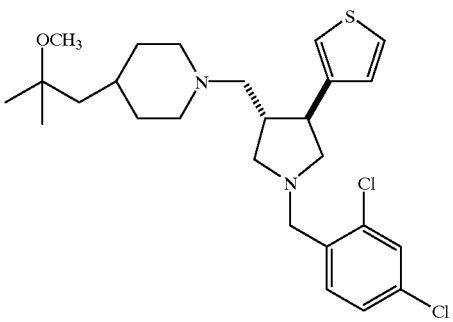

1-(2,4-Dichlorobenzyl)-3-(S)-(4-(2-methoxy-2-methyl-1-propyl)piperidinylmethyl)-4-(S)-(3-thienyl)pyrrolidine Mass Spectrum (ESI) m/e=495 (M+1 $^{35}$Cl, $^{35}$Cl), 497 (M+1 $^{35}$Cl, $^{37}$Cl), and 499 (M+1 $^{37}$Cl, $^{37}$Cl).

Preparation of 1-t-Butoxycarbonyl-4-(2-methoxy-2-methyl-1-propyl)piperidine

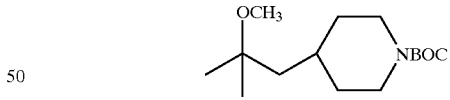

To a mixture of 0.06 g (2.5 mmol) of NaH in 5 mL of DMF at rt was added a solution of 0.1 g (0.39 mmol) of 1-t-butoxycarbonyl-4-(2-hydroxy-2-methyl-1-propyl)piperidine in 3 mL of DMF. After stirring for 20 min, 0.22 mL (3.5 mmol) of CH3I was added to the reaction mixture and the reaction mixture was stirred for 2 h. The reaction mixture was quenched with water and extracted with EtOAc. The combined organic fractions were washed with sat'd NaCl solution, dried over MgSO$_4$, filtered and the filtrate was concentrated. The residue was purified by chromatography (silica, hexanes:ethyl acetate, 9:1) to give 0.096 g of the title compound.

EXAMPLE 48

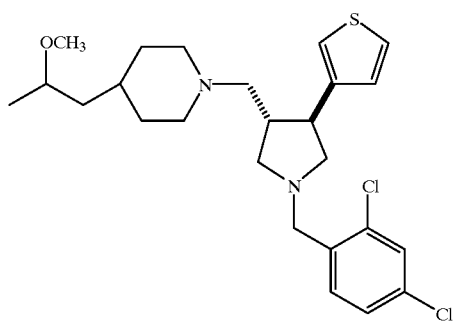

1-(2,4-Dichlorobenzyl)-3-(S)-(4-(2-methoxy-1-propyl)piperidinylmethyl)-4-(S)-(3-thienyl)pyrrolidine Mass Spectrum (ESI) m/e=481 (M+1 $^{35}$Cl, $^{35}$Cl), 483 (M+1 $^{35}$Cl, $^{37}$Cl), and 485 (M+1 $^{37}$Cl, $^{37}$Cl).

Preparation of 4-(2-methoxy-1-propyl)piperidine

The title compound was prepared from 1-t-butoxycarbonyl-4-(2-hydroxy-1-propyl)piperidine (Example 26) according to procedures described in Example 34.

The following Examples 49 to 53 were prepared from 1-(2,4-dichlorobenzyl)-3-(R)-formyl-4-(S)-(3-thienyl)pyrrolidine according to procedures described in Example 4. The piperidine sidechains were prepared as described in Examples 46 or 47.

EXAMPLE 49

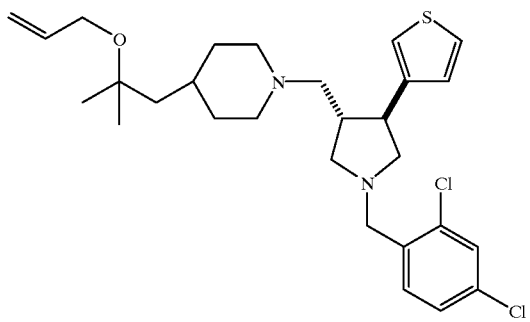

1-(2,4-Dichlorobenzyl)-3-(S)-(4-(2-allyloxy-2-methyl-1-propyl)piperidinylmethyl)-4-(S)-(3-thienyl)pyrrolidine Mass Spectrum (ESI) m/e=521 (M+1 $^{35}$Cl, $^{35}$Cl), 523 (M+1 $^{35}$Cl, $^{37}$Cl), and 525 (M+1 $^{37}$Cl, $^{37}$Cl).

EXAMPLE 50

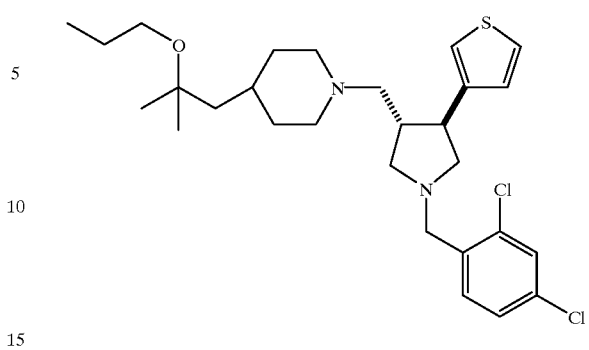

1-(2,4-Dichlorobenzyl)-3-(S)-(4-(2-n-propyloxy-2-methyl-1-propyl)piperidinylmethyl)-4-(S)-(3-thienyl)pyrrolidine Mass Spectrum (ESI) m/e=523 (M+1 $^{35}$Cl, $^{35}$Cl), 525 (M+1 $^{35}$Cl, $^{37}$Cl), and 527 (M+1 $^{37}$Cl, $^{37}$Cl).

Preparation of 4-(2-n-propyloxy-2-methyl-1-propyl)piperidine

A mixture of 0.09 g (0.3 mmol) of 1-t-butoxycarbonyl-4-(2-allyloxy-2-methyl-1-propyl)piperidine and 0.0058 g of Pd/C (10%) in 2 mL of CH$_3$OH was stirred under H$_2$ (1 atm) for 24 h. The reaction mixture was filtered through a thin pad of Celite and the filtrate was concentrated. The residue was purified by chromatography (silica, hexanes:ether, 6:1) to give 0.06 g of the title compound.

EXAMPLE 51

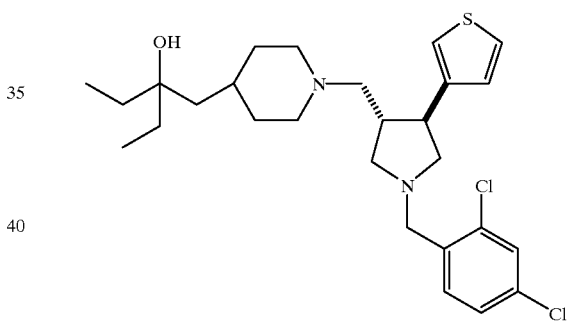

1-(2,4-Dichlorobenzyl)-3-(S)-(4-(2-hydroxy-2-ethyl-1-butyl)piperidinylmethyl)-4-(S)-(3-thienyl)pyrrolidine Mass Spectrum (ESI) m/e=509 (M+1 $^{35}$Cl, $^{35}$Cl), 511 (M+1 $^{35}$Cl, $^{37}$Cl), and 513 (M+1 $^{37}$Cl, $^{37}$Cl)

EXAMPLE 52

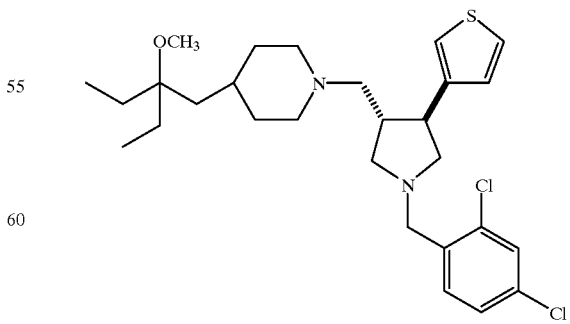

1-(2,4-Dichlorobenzyl)-3-(S)-(4-(2-methoxy-2-ethyl-1-butyl)piperidinylmethyl)-4-(S)-(3-thienyl)pyrrolidine Mass Spectrum (ESI) m/e=509 (M+1 $^{35}$Cl, $^{35}$Cl), 511 (M+1 $^{35}$Cl, $^{37}$Cl), and 513 (M+1 $^{37}$Cl,$^{37}$Cl).

EXAMPLE 53

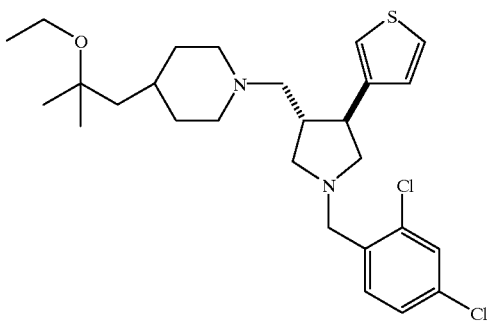

1-(2,4-Dichlorobenzyl)-3-(S)-(4-(2-ethoxy-2-methyl-1-propyl)piperidinylmethyl)-4-(S)-(3-thienyl)pyrrolidine Mass Spectrum (ESI) m/e=509 (M+1 $^{35}$Cl, $^{35}$Cl), 511 (M+1 $^{35}$Cl, $^{37}$Cl), and 513 (M+1 $^{37}$Cl, $^{37}$Cl).

The following Examples 54 to 55 were prepared from 1-(2,4-dichlorobenzyl)-3-(R)-formyl-4-(S)-(3-thienyl)pyrrolidine according to procedures described in Example 4. The piperidine sidechains were prepared from 1-t-butoxycarbonyl-4-(2-hydroxy-1-propyl)piperidine (Example 26) according to procedures described in Example 34.

EXAMPLE 54

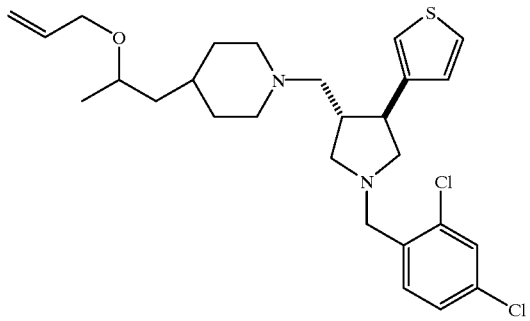

1-(2,4-Dichlorobenzyl)-3-(S)-(4-(2-allyloxy-1-propyl)piperidinylmethyl)-4-(S)-(3-thienyl)pyrrolidine Mass Spectrum (ESI) m/e=507 (M+1 $^{35}$Cl, $^{35}$Cl), 509 (M+1 $^{35}$Cl, $^{37}$Cl), and 513 (M+1 $^{37}$Cl, $^{37}$Cl).

EXAMPLE 55

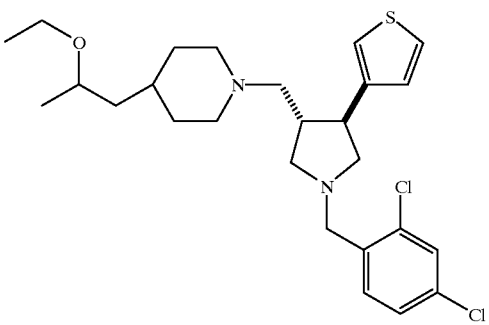

1-(2,4-Dichlorobenzyl)-3-(S)-(4-(2-ethoxy 1-propyl)piperidinylmethyl)-4-(S)-(3-thienyl)pyrrolidine Mass Spectrum (ESI) m/e=495 (M+1 $^{35}$Cl, $^{35}$Cl), 497 (M+1 $^{35}$Cl, $^{37}$Cl), and 499 (M+1 $^{37}$Cl, $^{37}$Cl).

The following Examples 56 to 58 were prepared from 1-(2,4-dichlorobenzyl)-3-(R)-formyl-4-(S)-(3-thienyl)pyrrolidine according to procedures described in Example 4. The piperidine sidechains were prepared as described.

EXAMPLE 56

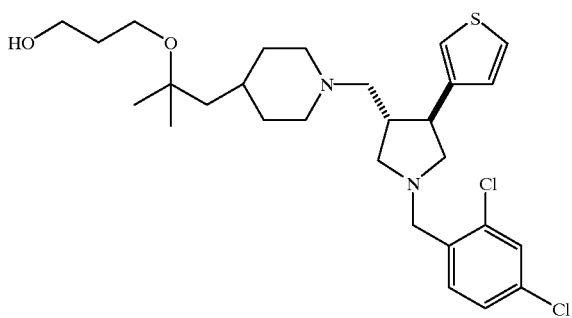

1-(2,4-Dichlorobenzyl)-3-(S)-(4-(2-(3-hydroxy1-propyl)oxy-2-methyl-1-propyl)piperidinylmethyl)-4-(S)-(3-thienyl)pyrrolidine Mass Spectrum (ESI) m/e=539 (M+1 $^{35}$Cl, $^{35}$Cl), 541 (M+1 $^{35}$Cl, $^{37}$Cl), and 543 (M+1 $^{37}$Cl, $^{37}$Cl).

Preparation of 1-t-butoxycarbonyl-4-(2-(3-hydroxy1-propyl)oxy-2-methyl-1-propyl)piperidine Step 1. 3-(Triisopropylsilyloxy)-1-propylbromide To a solution of 20 mL (20 mmol) of 3-bromopropanol in 50 mL of CH$_2$Cl$_2$ at 0° C. was added dropwise 5 mL (23.3 mmol) of triisopropylsilyl chloride. After stirring for 5 min, was then added dropwise a solution of 3.4 g (50 mmol) of imidazole in 25 mL of CH$_2$Cl$_2$ followed by 0.126 g (1 mmol) of dimethylaminopyridine (DMAP). The reaction mixture was warmed slowly to rt and stirred 18 h. The reaction mixture was diluted with ether and washed successively with water, dilute NH$_4$Cl solution, and sat'd NH$_4$Cl solution. The combined organic fractions were dried over Na$_2$SO$_4$, filtered and the filtrate was concentrated to give 6.5 g of the title compound which was used as is.

Step 2. 1-t-Butoxycarbonyl-4-(2-( 3-triisopropylsilyloxy-1-propyl)oxy-2-methyl-1-propyl)piperidine The title compound was prepared from 4-(2-hydroxy-2-methyl-1-propyl)piperidine and 3-(triisopropylsilyloxy)-1-propylbromide according to procedures described in Example 25. The crude product was purified by chromatography (silica, hexanes:acetone, 9:1) to give 0.245 g of the title compound.

Step 3. 1-t-Butoxycarbonyl-4-(2-(3-hydroxy-1-propyl)oxy-2-methyl-1-propyl)piperidine A solution of 0.245 g (0.52 mmol) of 1-t-butoxycarbonyl-4-(2-(3-triisopropylsilyloxy-1-propyl)oxy-2-methyl-1-propyl)piperidine and 0.53 mL (0.53 mmol) of tetrabutylammonium fluoride (TBAF) in 2 mL of THF was stirred at rt for 2 h. The reaction mixture was partitioned between ether and water. The combined organic fractions were washed with sat'd NaCl solution, dried over MgSO$_4$, filtered and the filtrate was concentrated. The residue was purified by chromatography (silica, hexanes:acetone, 9:1) to give the title compound.

EXAMPLE 57

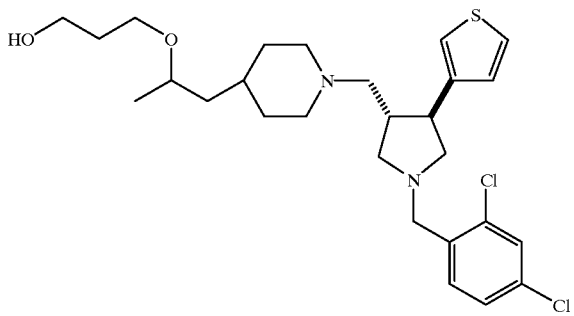

1-(2,4-Dichlorobenzyl)-3-(S)-(4-(2-(3-hydroxy-1-propyl)oxy-1-propyl)piperidinylmethyl)-4-(S)-(3-thienyl)pyrrolidine Mass Spectrum (ESI) m/e=525 (M+1 $^{35}$Cl, $^{35}$Cl), 527 (M+1 $^{35}$Cl, $^{37}$Cl), and 529 (M+1 $^{37}$Cl, $^{37}$Cl).

Preparation of 1-t-butoxycarbonyl-4-(2-(3-hydroxy-1-propyl)oxy-1-propyl)piperidine The title compound was prepared from 1-t-butoxycarbonyl-4-(2-hydroxy-1-propyl)piperidine according to procedures described in Example 56.

EXAMPLE 58

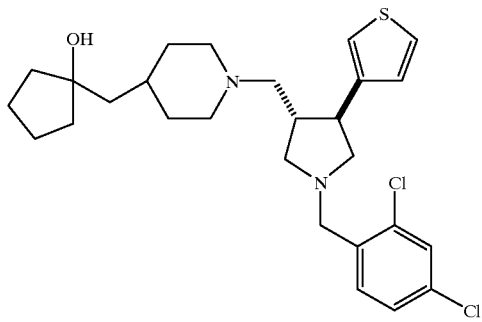

1-(2,4-Dichlorobenzyl)-3-(S)-(4-(2-cyclopentyl-2-hydroxyethyl) piperidinylmethyl)-4-(S)-(3-thienyl)pyrrolidine Mass Spectrum (ESI) m/e=507 (M+1 $^{35}$Cl, $^{35}$Cl), 509 (M+1 $^{35}$Cl, $^{37}$Cl), and 511 (M+1 $^{37}$Cl, $^{37}$Cl).

Preparation of 1-t-butoxycarbonyl-4-(2-cyclopentyl-2-hydroxyethyl)piperidine

Step 1. 1-t-Butoxycarbonyl-4-methanesulfonyloxymethylpiperidine

To a solution of 5 g (23.4 mmol) of 1-t-butoxycarbonyl-4-hydroxymethylpiperidine (Example 8) and 6.5 mL (46.6 mmol) of triethylamine in 50 mL of CH$_2$Cl$_2$ at 0° C. was added dropwise a solution of 6.1 g (35 mmol) of methanesulfonic anhydride in 10 mL of CH$_2$Cl$_2$. After 5 min, 0.137 g (1.12 mmol) of DMAP was added and the reaction mixture was warmed to rt and stirred for 18 h. The reaction mixture was concentrated, then partitioned in a mixture of 100 mL of ether, 15 mL of CH$_2$Cl$_2$ and 100 mL of water. The aqueous fraction was extracted with ether and the combined organic fractions were washed with sat'd NaCl solution, dried over MgSO$_4$, filtered and the filtrate was concentrated to give 7.23 g of the title compound that was used without further purification.

Step 2. 1-t-Butoxycarbonyl-4-iodomethylpiperidine

To solution of 7.23 g (23.42 mmol) of 1-t-butoxycarbonyl-4-methanesulfonyloxymethylpiperidine in 70 mL of DMF at 0° C. was added portionwise 9.25 g (69.1 mmol) of LiI. The reaction mixture was heated at 50° C. for 36 h. The reaction mixture was partitioned between ether and water. The aqueous fraction was extracted with ether and the combined organic fractions were washed with sat'd NaCl solution, dried over MgSO$_4$, filtered and the filtrate was concentrated. The residue was purified by chromatography (silica, hexanes ether, 4:1) to give 6 g of the title compound.

Step 3. 1-t-Butoxycarbonyl-4-(2-cyclopentyl-2-hydroxyethyl)piperidine

To a solution of 1.36 g (4.2 mmol) of 1-t-butoxycarbonyl-4-iodomethylpiperidine in 40 mL of ether at −78° C. was carefully added 5.8 mL (9.35 mmol) of t-butyl lithium (1.7 N on pentane). After stirring for 30 min, to the reaction mixture was added dropwise 0.95 mL (10.73 mmol) of cyclopentanone and the reaction mixture was stirred at −78° C. for 2 h. To the reaction mixture was added 5 mL of sat'd NH$_4$Cl solution and the reaction mixture was warmed to rt. The reaction mixture was partitioned between sat'd NH$_4$Cl solution and ether. The aqueous fraction was extracted with ether and the combined organic fractions were washed with sat'd NaCl solution, dried over MgSO$_4$, filtered and the filtrate was concentrated. The residue was purified by chromatography (silica, hexanes:ether, 4:1) to give 0.36 g of the title compound.

The following Examples 59 to 63 were prepared from 1-(2,4-dichlorobenzyl)-3-(R)-formyl-4-(S)-(3-thienyl)pyrrolidine according to procedures described in Example 4. The piperidine sidechains were prepared as described in Example 58.

EXAMPLE 59

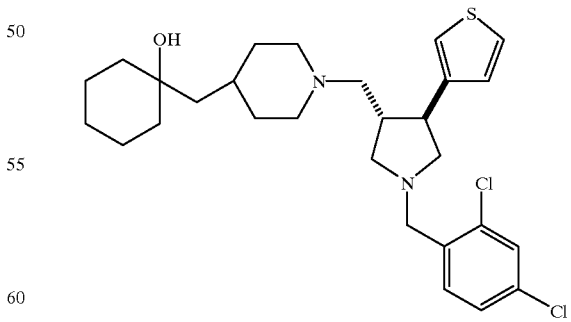

1-(2,4-Dichlorobenzyl)-3-(S)-(4-(2-cyclohexyl-2-hydroxyethyl)piperidinylmethyl)-4-(S)-(3-thienyl)pyrrolidine Mass Spectrum (ESI) m/e=521 (M+1 $^{35}$Cl, $^{35}$Cl), 523 (M+1 $^{35}$Cl, $^{37}$Cl), and 525 (M+1 $^{37}$Cl, $^{37}$Cl).

EXAMPLE 60

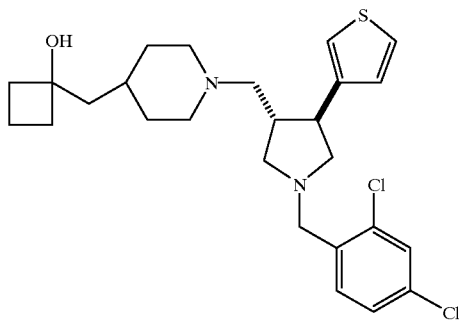

1-(2,4-Dichlorobenzyl)-3-(S)-(4-(2-cyclobutyl-2-hydroxyethyl) piperidinylmethyl)-4-(S)-(3-thienyl)pyrrolidine Mass Spectrum (ESI) m/e=493 (M+1 $^{35}$Cl, $^{35}$Cl), 495 (M+1 $^{35}$Cl, $^{37}$Cl), and 497 (M+1 $^{37}$Cl, $^{37}$Cl).

EXAMPLE 61

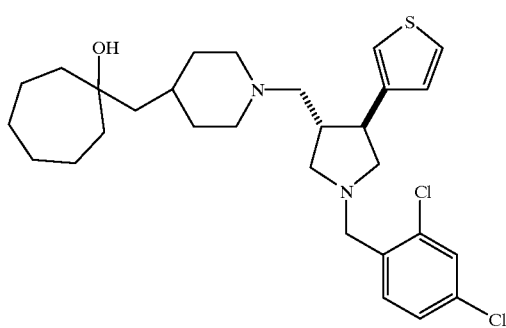

1-(2,4-Dichlorobenzyl)-3-(S)-(4-(2-cycloheptyl-2-hydroxyethyl)piperidinylmethyl)-4-(S)-(3-thienyl)pyrrolidine Mass Spectrum (ESI) m/e=535 (M+1 $^{35}$Cl, $^{35}$Cl), 537 (M+1 $^{35}$Cl, $^{37}$Cl), and 539S (M+1 $^{37}$Cl, $^{37}$Cl).

EXAMPLE 62

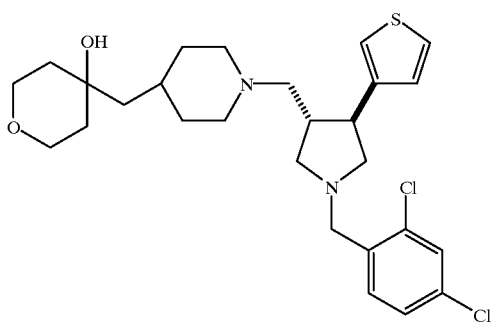

1-(2,4-Dichlorobenzyl)-3-(S)-(4-(2-(4-tetrahydropyranyl)-2-hydroxyethyl) piperidinylmethyl)-4-(S)-(3-thienyl)pyrrolidine Mass Spectrum (ESI) m/e=523 (M+1 $^{35}$Cl, $^{35}$Cl), 525 (M+1 $^{35}$Cl, $^{37}$Cl), and 527 (M+1 $^{37}$Cl, $^{37}$Cl).

EXAMPLE 63

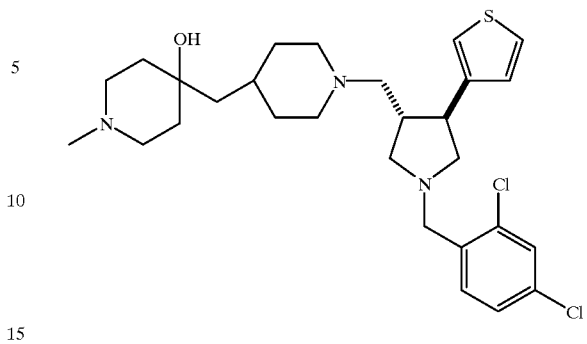

1-(2,4-Dichlorobenzyl)-3-(S)-(4-(2-(N-methyl-4-piperidinyl)-2-hydroxyethyl) piperidinylmethyl)-4-(S)-(3-thienyl)pyrrolidine Mass Spectrum (ESI) m/e=536 (M+1 $^{35}$Cl, $^{35}$Cl), 539 (M+1 $^{35}$Cl, $^{37}$Cl), and 541S

EXAMPLE 64

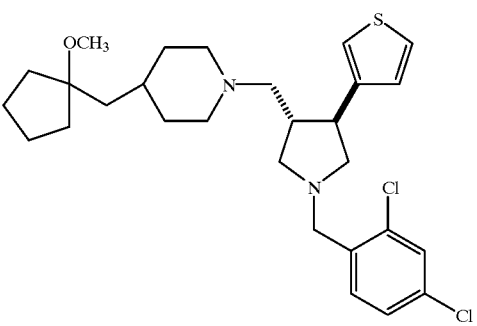

1-(2,4-Dichlorobenzyl)-3-(S )-(4-(2-cyclopentyl-2-methoxyethyl)piperidinylmethyl)-4-(S)-(3-thienyl)pyrrolidine Mass Spectrum (ESI) m/e=521 (M+1 $^{35}$Cl, $^{35}$Cl), 523 (M+1 $^{35}$Cl, $^{37}$Cl), and 525 (m+1 $^{37}$Cl, $^{37}$Cl).

The title compound was prepared from 1-(2,4-dichlorobenzyl)-3-(R)-formyl-4-(S)-(3-thienyl)pyrrolidine according to procedures described in Example 4. The piperidine sidechain was prepared from 1-t-butoxycarbonyl-4-(2-cyclopentyl-2-hydroxyethyl) piperidine as described in Example 48.

The following Examples 65 to cd were prepared from 1-(2,4-dichlorobenzyl)-3-(R)-formyl-4-(S)-(3-thienyl)pyrrolidine according to procedures described in Example 4. The piperidine sidechains were prepared according to procedures referenced in Example 64.

EXAMPLE 65

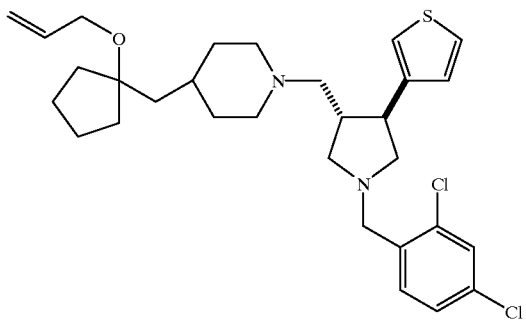

1-(2,4-Dichlorobenzyl)-3-(S)-(4-(2-cyclopentyl-2-allyloxyethyl)piperidinylmethyl)-4-(S)-(3-thienyl) pyrrolidine
Mass Spectrum (ESI) m/e=547 (M+1 $^{35}$Cl, $^{35}$Cl), 549 (M+1 $^{35}$Cl, $^{37}$Cl), and 551 (M+1 $^{37}$Cl, $^{37}$Cl).

EXAMPLE 66

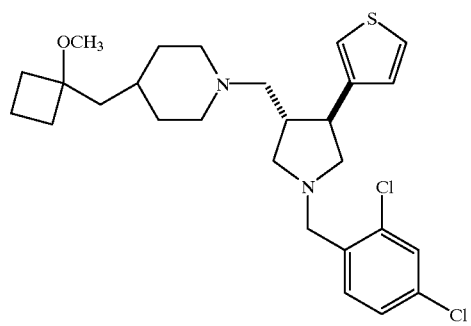

1-(2,4-Dichlorobenzyl)-3-(S)-(4-(2-cyclobutyl-2-methoxyethyl) piperidinylmethyl)-4-(S)-(3-thienyl) pyrrolidine
Mass Spectrum (ESI) m/e=507 (M+1 $^{35}$Cl, $^{35}$Cl), 509 (M+1 $^{35}$Cl, $^{37}$Cl), and 511 (M+1 $^{37}$Cl, $^{37}$Cl).

EXAMPLE 67

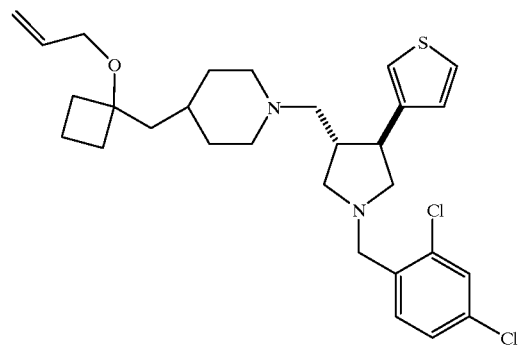

1-(2,4-Dichlorobenzyl)-3-(S)-(4-(2-cyclobutyl-2-allyloxyethyl) piperidinylmethyl)-4-(S)-(3-thienyl) pyrrolidine
Mass Spectrum (ESI) m/e=533 (M+1 $^{35}$Cl, $^{35}$Cl), 535 (M+1 $^{35}$Cl, $^{37}$Cl), and 537 (M+1 $^{37}$Cl, $^{37}$Cl).

EXAMPLE 68

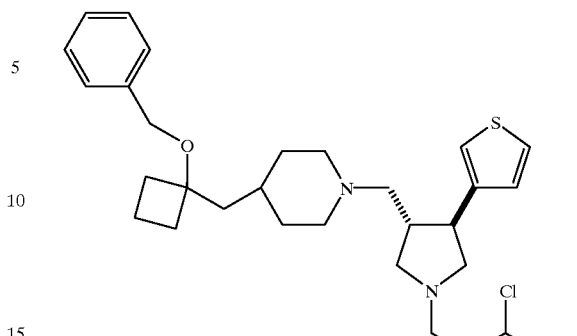

1-(2,4-Dichlorobenzyl)-3-(S)-(4-(2-cyclobutyl-2-benzyloxyethyl) piperidinylmethyl)-4-(S)-(3-thienyl) pyrrolidine
Mass Spectrum (ESI) m/e=583 (M+1 $^{35}$Cl, $^{35}$Cl), 585 (M+1 $^{35}$Cl, $^{37}$Cl), and 587 (M+1 $^{37}$Cl, $^{37}$Cl).

EXAMPLE 69

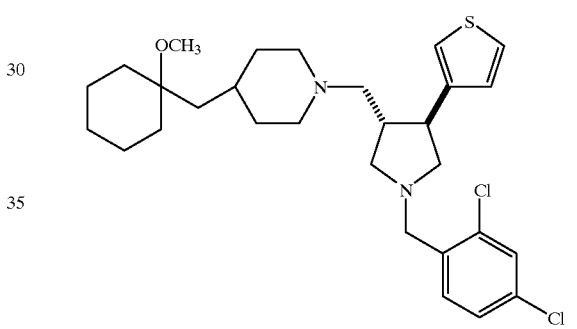

1-(2,4-Dichlorobenzyl)-3-(S)-(4-(2-cyclohexyl-2-methoxyethyl)piperidinylmethyl)-4-(S)-(3-thienyl) pyrrolidine
Mass Spectrum (ESI) m/e=535 (M+1 $^{35}$Cl, $^{35}$Cl), 537 (M+1 $^{35}$Cl, $^{37}$Cl), and 539 (M+1 $^{37}$Cl, $^{37}$Cl).

EXAMPLE 70

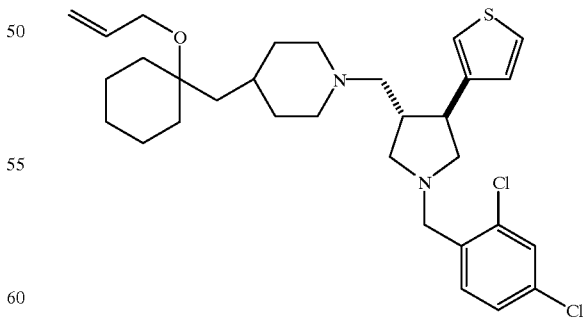

1-(2,4-Dichlorobenzyl)-3-(S)-(4-(2-cyclohexyl-2-allyloxyethyl)piperidinylmethyl)-4-(S)-(3-thienyl) pyrrolidine
Mass Spectrum (ESI) m/e=561 (M+1 $^{35}$Cl, $^{35}$Cl), 563 (M+1 $^{35}$Cl, $^{37}$Cl), and 565 (M+1 $^{37}$Cl, $^{37}$Cl).

EXAMPLE 71

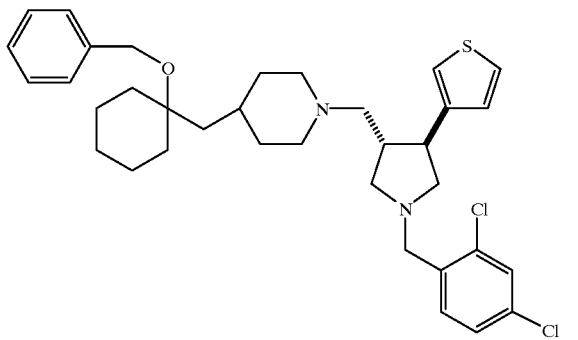

1-(2,4-Dichlorobenzyl)-3-(S)-(4-(2-cyclohexyl-2-benzyloxyethyl)piperidinylmethyl)-4-(S)-(3-thienyl)pyrrolidine Mass Spectrum (ESI) m/e=611 (M+1 $^{35}$Cl, $^{35}$Cl), 613 (M+1 $^{35}$Cl, $^{37}$Cl), and 615 (M+1 $^{37}$Cl, $^{37}$Cl).

EXAMPLE 72

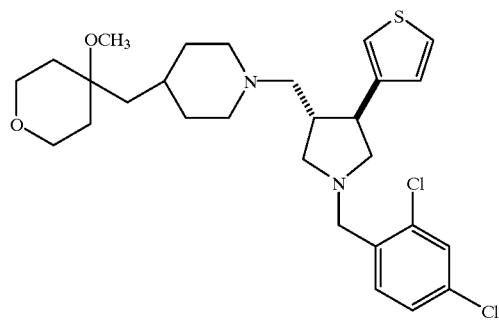

1-(2,4-Dichlorobenzyl)-3-(S)-(4-(2-(4-tetrahydropyranyl)-2-methoxyethyl) piperidinylmethyl)-4-(S)-(3-thienyl)pyrrolidine Mass Spectrum (ESI) m/e=537 (M+1 $^{35}$Cl, $^{35}$Cl), 539 (M+1 $^{35}$Cl, $^{37}$Cl), and 541 (M+1 $^{37}$Cl, $^{37}$Cl).

EXAMPLE 73

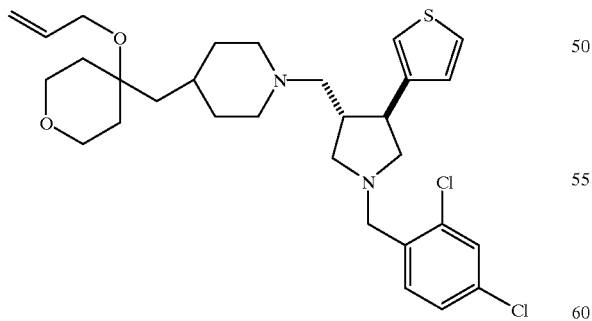

1-(2,4-Dichlorobenzyl)-3-(S)-(4-(2-(4-tetrahydropyranyl)-2-allyloxyethyl) piperidinylmethyl)-4-(S)-(3-thienyl)pyrrolidine Mass Spectrum (ESI) m/e=563 (M+1 $^{35}$Cl, $^{35}$Cl), 565 (M+1 $^{35}$Cl, $^{37}$Cl), and 567 (M+1 $^{37}$Cl, $^{37}$Cl)

EXAMPLE 74

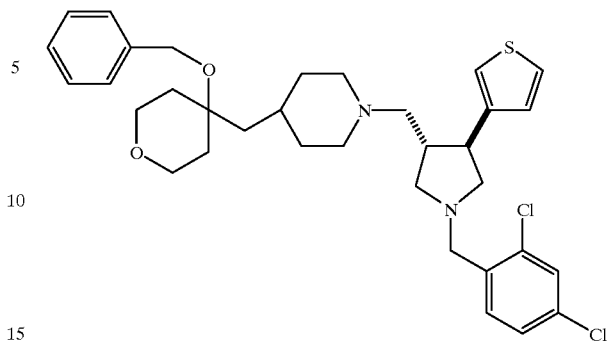

1-(2,4-Dichlorobenzyl)-3-(S)-(4-(2-(4-tetrahydropyranyl)-2-benzyloxyethyl) piperidinylmethyl)-4-(S)-(3-thienyl)pyrrolidine Mass Spectrum (ESI) m/e=613 (M+1 $^{35}$Cl, $^{35}$Cl), 615 (M+1 $^{35}$Cl, $^{37}$Cl), and 617 (M+1 $^{37}$Cl, $^{37}$Cl).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

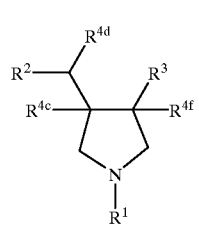

wherein:

$R^1$ is selected from the group consisting of:

(1) —CH$_2$-phenyl, and (2) —CH$_2$-(2,4-dicholorophenyl)

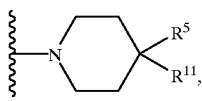

wherein R$^5$ is C$_{1-8}$alkyl, which is substituted, where the substituents are independently selected from:
(a) hydroxy,
(b) C$_{1-3}$alkoxy,
(c) —O—C$_{1-3}$alkyl—O—C$_{1-3}$alkyl,
(d) —O—C$_{1-3}$alkyl-hydroxy,
(e) —O—C$_{1-3}$alkyl-cyclopropyl,
(f) —O—C$_{1-3}$alkyl-cyclobutyl,
(g) —O—C$_{3-4}$alkenyl
(h) —OC(C$_{1-6}$alkyl),
(i) —NH$_2$,
(j) —NHCO(C$_{1-6}$alkyl),
(k) —NHSO$_2$(C$_{1-6}$alkyl),
(l) cyclobutyl,
(m) cyclopentyl,
(n) cyclohexyl,
(o) cycloheptyl,
(p) tetrahydropranyl,
(q) piperidinyl, and
(r) N—(C$_{1-6}$alkyl)piperidinyl; and
wherein R$^{11}$ is selected from:
(1) —hydrogen,
(2) —OH,
(3) —C$_{1-6}$alkyl, and
(4) —halogen;
R$^3$ is 3—thienyl;
R$^{4c}$, R$^{4d}$, and R$^{4f}$ are independently selected from the group consisting of:
(1) hydrogen, and
(2) C$_{1-6}$ alkyl;
and pharmaceutically acceptable salts thereof and individual diastereomers thereof.

2. The compound of claim 1 which is of the stereochemical comfiguration:

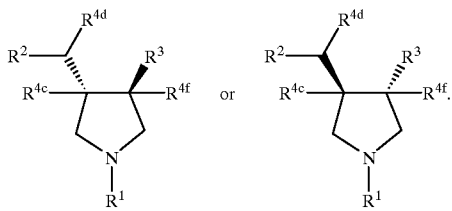

3. A compound which is selected from the group consisting of:
1-(2,4-Dichlorobenzyl)-3-(S)-(4-pentylpiperidinylmethyl)-4-(S)- (3-thienyl)-pyrrolidine;
1-(2,4-Dichlorobenzyl)-3-(S)-(4-butyloxy)piperidinylmethyl-4-(S)-(3-thienyl)-pyrrolidine;
1-(2,4-Dichlorobenzyl)-3-(S)-(4-(hydroxymethyl)piperidinylmethyl)-4-(S)-(3-thienyl)-pyrrolidine;
1-(2,4-Dichlorobenzyl)-3-(S)-(4-(methoxymethyl)piperidinylmethyl)-4-(S)-(3-thienyl)-pyrrolidine;
1-(2,4-Dichlorobenzyl)-3-(S)-(4-(ethoxymethyl)piperidinylmethyl)-4-(S)-(3-thienyl)-pyrrolidine;
1-(2,4-Dichlorobenzyl)-3-(S)-(4-(propoxymethyl)piperidinylmethyl)-4-(S)-(3-thienyl)pyrrolidine;
1-(2,4-Dichlorobenzyl)-3-(S)-(4-(allyloxymethyl)piperidinylmethyl)-4-(S)-(3-thienyl)pyrrolidine;
1-(2,4-Dichlorobenzyl)-3-(S)-(4-(isopropoxymethyl)piperidinylmethyl)-4-(S)-(3-thienyl)pyrrolidine;
1-(2,4-Dichlorobenzyl)-3-(S)-(4-(cyclopropylmethyloxymethyl)piperidinylmethyl)-4-(S)-(3-thienyl)pyrrolidine;
1-(2,4-Dichlorobenzyl)-3-(S)-(4-(cyclobutylmethyloxymethyl)piperidinylmethyl)-4-(S)-(3-thienyl)pyrrolidine;
1-(2,4-dichlorobenzyl)-3-(S)-(4-(methoxyethyloxymethyl)piperidinylmethyl)-4-(S)-(3-thienyl)pyrrolidine;
1-(2,4-Dichlorobenzyl)-3-(S)-(4-(3-hydroxypropyloxymethyl)piperidinylmethyl)-4-(S)-(3-thienyl)pyrrolidine;
1-(2,4-Dichlorobenzyl)-3-(S)-(4-(3-methoxypropyloxymethyl) piperidinylmethyl)-4-(S)-(3-thienyl)pyrrolidine;
1(2,4-Dichlorobenzyl)-3-(S)-(4-(3-aminopropyloxymethyl)piperidinylmethyl)-4-(S)-(3-thienyl)pyrrolidine;
1-(2,4-Dichlorobenzyl)-3-(S)-(4-(3-(acetylamino)propyloxymethyl) piperidinylmethyl)-4-(S)-(3-thienyl)pyrrolidine;
1-(2,4-Dichlorobenzyl)-3-(S)-(4-(3-(methylsulfonylamino)propyloxymethyl) piperidinylmethyl)-4-(S)-(3-thienyl)pyrrolidine;
1-(2,4-Dichlorobenzyl)-3-(S)-(4-(hydroxyethyl)piperidinylmethyl)-4-(S)-(3-thienyl)pyrrolidine;
1-(2,4-Dichlorobenzyl)-3-(S)-(4-(methoxyethyl)piperidinylmethyl)-4-(S)-(3-thienyl)pyrrolidine;
1-(2,4-Dichlorobenzyl)-3-(S)-(4-(2-(RS)-hydroxypropyl)piperidinylmethyl)-4-(S)-(3-thienyl)pyrrolidine;
1-(2,4-Dichlorobenzyl)-3-(S)-(4-(2-(RS)-hydroxybutyl)piperidinylmethyl)-4-(S)-(3-thienyl)pyrrolidine;
1-(2,4-Dichlorobenzyl)-3-(S)-(4-(2-(RS)-hydroxypentyl)piperidinylmethyl)-4-(S)-(3-thienyl)pyrrolidine;
1-(2,4-Dichlorobenzyl)-3-(S)-(4-(2-(RS)-hydroxy-3-methylbutyl)piperidinylmethyl)-4-(S)-(3-thienyl)pyrrolidine;
1-(2,4-Dichlorobenzyl)-3-(S)-(4-(2-(RS)-hydroxyhexyl)piperidinylmethyl)-4-(S)-(3-thienyl)pyrrolidine;
1-(2,4-Dichlorobenzyl)-3-(S)-(4-(2-(RS)-hydroxy-4-pentyl)piperidinylmethyl)-4-(S)-(3-thienyl)pyrrolidine;
1-(2,4-Dichlorobenzyl)-3-(S)-(4-(2-(RS)-hydroxypent-4-enyl)piperidinylmethyl)-4-(S)-(3-thienyl)pyrrolidine;
1-(2,4-Dichlorobenzyl)-3-(S)-(4-(2-(RS)-hydroxy-3,3-dimethylbutyl)piperidinylmethyl)-4-(S)-(3-thienyl)pyrrolidine;
1-(2,4-Dichlorobenzyl)-3-(S)-(4-(2-(RS)-methoxybutyl)piperidinylmethyl)-4-(S)-(3-thienyl)pyrrolidine;
1-(2,4-Dichlorobenzyl)-3-(S)-(4-(2-(RS)-methoxypentyl)piperidinylmethyl)-4-(S)-(3-thienyl)pyrrolidine;
1-(2,4-Dichlorobenzyl)-3-(S)-(4-(2-(RS)-methoxy-3-methylbutyl)piperidinylmethyl)-4-(S)-(3-thienyl)pyrrolidine;
1-(2,4-Dichlorobenzyl)-3-(S)-(4-(2-(RS)-methoxyhexyl)piperidinylmethyl)-4-(S)-(3-thienyl)pyrrolidine;
1-(2,4-Dichlorobenzyl)-3-(S)-(4-(2-(RS)-methoxy-4-methylpentyl)piperidinylmethyl)-4-(S)-(3-thienyl)pyrrolidine;
1-(2,4-Dichlorobenzyl)-3-(S)-(4-(2-(RS)-methoxypent-4-enyl)piperidinylmethyl)-4-(S)-(3-thienyl)pyrrolidine;
1-(2,4-Dichlorobenzyl)-3-(S)-(4-(2-ketobutyl)piperidinylmethyl)-4-(S)-(3-thienyl)pyrrolidine;
1-(2,4-Dichlorobenzyl)-3-(S)-(4-(2-ketopentyl)piperidinylmethyl)-4-(S)-(3-thienyl)pyrrolidine;
1-(2,4-Dichlorobenzyl)-3-(S)-(4-(2-(RS)-hydroxy-2-methylpentyl)piperidinylmethyl)-4-(S)-(3-thienyl)pyrrolidine;

1-(2,4-Dichlorobenzyl)-3-(S)-(4-(2-(RS)-methoxy-2-methylpentyl)piperidinylmethyl)-4-(S)-(3-thienyl)pyrrolidine;
1-(2,4-Dichlorobenzyl)-3-(S)-(4-(2-(2-hydroxy-2-propylpentyl)piperidinylmethyl)-4-(S)-(3-thienyl)pyrrolidine;
1-(2,4-Dichlorobenzyl)-3-(S)-(4-(2-(2-methoxy-2-propylpentyl)piperidinylmethyl)-4-(S)-(3-thienyl)pyrrolidine;
1-(2,4-Dichlorobenzyl)-3-(S)-(4-(2-hydroxy-2-methyl-1-propyl)piperidinylmethyl)-4-(S)-(3-thienyl)pyrrolidine;
1-(2,4-Dichlorobenzyl)-3-(S)-(4-(2-methoxy-2-methyl-1-propyl)piperidinylmethyl)-4-(S)-(3-thienyl)pyrrolidine;
1-(2,4-Dichlorobenzyl)-3-(S)-(4-( 2-methoxy- 1-propyl)piperidinylmethyl)-4-(S)-(3-thienyl)pyrrolidine;
1-(2,4-Dichlorobenzyl)-3-(S)-(4-(2-allyloxy-2-methyl-1-propyl)piperidinylmethyl)-4-(S)-(3-thienyl)pyrrolidine;
1-(2,4-Dichlorobenzyl)-3-(S)-(4-(2-n-propyloxy-2-methyl-1-propyl)piperidinylmethyl)-0, 1 and 2, 4-(S)-(3-thienyl)pyrrolidine;
1-(2,4-Dichlorobenzyl)-3-(S)-(4-(2-hydroxy-2-ethyl-1-butyl)piperidinylmethyl)-4-(S)-(3-thienyl)pyrrolidine;
1-(2,4-Dichlorobenzyl)-3-(S)-(4-(2-methoxy-2-ethyl-1-butyl)piperidinylmethyl)-4-(S)-(3-thienyl)pyrrolidine;
1-(2,4-Dichlorobenzyl)-3-(S)-(4-(2-ethoxy-2-methyl-1-propyl)piperidinylmethyl)-4-(S)-(3-thienyl)pyrrolidine;
1-(2,4-Dichlorobenzyl)-3-(S)-(4-(2-allyloxy-1-propyl)piperidinylmethyl)-4-(S)-(3-thienyl)pyrrolidine;
1-(2,4-Dichlorobenzyl)-3-(S)-(4-(2-ethoxy-1-propyl)piperidinylmethyl)-4-(S)-(3-thienyl)pyrrolidine;
1-(2,4-Dichlorobenzyl)-3-(S)-(4-(2-(3-hydroxy-1-propyl)oxy-2-methyl-1-propyl)piperidinylmethyl)-4-(S)-(3-thienyl)pyrrolidine;
1-(2,4-Dichlorobenzyl)-3-(S)-(4-(2-(3-hydroxy-1-propyl)oxy-1-propyl)piperidinylmethyl)-4-(S)-(3-thienyl)pyrrolidine;
1-(2,4-Dichlorobenzyl)-3-(S)-(4-(2-cyclopentyl-2-hydroxyethyl) piperidinylmethyl)-4-(S)-(3-thienyl)pyrrolidine;
1-(2,4-Dichlorobenzyl)-3-(S)-(4-(2-cyclohexyl-2-hydroxyethyl) piperidinylmethyl)-4-(S)-(3-thienyl)pyrrolidine;
1-(2,4-Dichlorobenzyl)-3-(S)-(4-(2-cyclobutyl-2-hydroxyethyl) piperidinylmethyl)-4-(S)-(3-thienyl)pyrrolidine;
1-(2,4-Dichlorobenzyl)-3-(S)-(4-(2-cycloheptyl-2-hydroxyethyl) piperidinylmethyl)-4-(S)-(3-thienyl)pyrrolidine;
1-(2,4-Dichlorobenzyl)-3-(S)-(4-(2-(4-tetrahydropyranyl)-2-hydroxyethyl) piperidinylmethyl)-4-(S)-(3-thienyl)pyrrolidine;
1-(2,4-Dichlorobenzyl)-3-(S)-(4-(2- piperidinylmethyl)-4-(S)-(3-thienyl)pyrrolidine;
1-(2,4-Dichlorobenzyl)-3-(S)-(4-(2-cyclopentyl-2-methoxyethyl) piperidinylmethyl)-4-(S)-(3-thienyl)pyrrolidine;
1-(2,4-Dichlorobenzyl)-3-(S)-(4-(2-cyclopentyl-2-allyloxyethyl) piperidinylmethyl)-4-(S)-(3-thienyl)pyrrolidine;
1-(2,4-Dichlorobenzyl)-3-(S)-(4-(2-cyclobutyl-2-methoxyethyl) piperidinylmethyl)-4-(S)-(3-thienyl)pyrrolidine;
1-(2,4-Dichlorobenzyl)-3-(S)-(4-(2-cyclobutyl-2-allyoxyethyl) piperidinylmethyl)-4-(S)-(3-thienyl)pyrrolidine;
1-(2,4-Dichlorobenzyl)-3-(S)-(4-(2-cyclobutyl-2-benzyloxyethyl) piperidinylmethyl)-4-(S)-(3-thienyl)pyrrolidine;
1-(2,4-Dichlorobenzyl)-3-(S)-(4-(2-cyclobutyl-2-methyloxyethyl) piperidinylmethyl)-4-(S)-(3-thienyl)pyrrolidine;
1-(2,4-Dichlorobenzyl)-3-(S)-(4-(2-cyclohexyl-2-allyloxyethyl) piperidinylmethyl)-4-(S)-(3-thienyl)pyrrolidine;
1-(2,4-Dichlorobenzyl)-3-(S)-(4-(2-cyclohexyl-2-benyoxyethyl) piperidinylmethyl)-4(S)-(3-thienyl)pyrrolidine;
1-(2,4-Dichlorobenzyl)-3-(S)-(4-(2-(4tetrhydropyranyl)-2-methoxyethyl) piperidinylmethyl)-4-(S)-(3-thienyl)pyrrolidine;
1-(2,4-Dichlorobenzyl)-3-(S)-(4-(2-(4-tetrahydropyranyl)-2-allyloxyethyl) piperidinylmethyl)-4-(S)-(3-thienyl)pyrrolidine;
1-(2,4-Dichlorobenzyl)-3-(S)-(4-(2-(4-tetrahydropyranyl)-2-benzyloxyethyl) piperidinylmethyl)-4-(S)-(3-thienyl)pyrrolidine;
and pharmaceutically acceptable salts thereof and individual diastereomers thereof.

4. A pharmaceutical composition which comprises an inert carrier and a compound of claim 1.

5. A method for antagonizing chemokine CCR-3 or CCR-5 receptor activity in a mammal comprising the administration of an effective amount of the compound of claim 1.

6. A method for treating infection by HIV, delaying of the onset of AIDS, or treating AIDS comprising the administration to a patient of an effective amount of the compound of claim 1.

7. A method for the treatment of an inflammatory and immunoregulatory disorder or disease which comprises the administration to a patient of an effective amount of the compound of claim 1.

8. A method for treatment of asthma, allergic rhinitis, dermatitis, conjunctivitis, atherosclerosis or rheumatoid arthritis which comprises the administration to a patient of an effective amount of the compound of claim 1.

* * * * *

UNITED STATES PATENT AND TRADEMARK OFFICE
CERTIFICATE OF CORRECTION

PATENT NO.     : 6,455,548 B2
DATED          : September 24, 2002
INVENTOR(S)    : Jennifer Chee et al.

It is certified that error appears in the above-identified patent and that said Letters Patent is hereby corrected as shown below:

Column 91,
Lines 18 through 20, should read -- 1-(2,4-Dichlorobenzyl)-3-(S)-(4-(2-n-propyloxy-2-methyl-1-propyl)piperidinyl-methyl)-4-(S)-(3-thienyl)pyrrolidine; --.
Lines 52 and 53, should read -- 1-(2,4-Dichlorobenzyl)-3-(S)-(4-(2-(N-methyl-4-piperidinyl)-2-hydroxyethyl)piperidinylmethyl)-4-(S)-(3-thienyl)pyrrolidine; --.

Column 92,
Lines 16 through 18, should read -- 1-(2,4-Dichlorobenzyl)-3-(S)-(4-(2-cyclohexyl-2-methoxyethyl)piperidinylmethyl)-4-(S)-(3-thienyl)pyrrolidine; --.

Signed and Sealed this

Eleventh Day of February, 2003

JAMES E. ROGAN
*Director of the United States Patent and Trademark Office*